United States Patent
Murphy

(10) Patent No.: US 9,232,776 B2
(45) Date of Patent: *Jan. 12, 2016

(54) HUMANIZED IL-7 RODENTS

(71) Applicant: Regeneron Pharmaceuticals, Inc., Tarrytown, NY (US)

(72) Inventor: Andrew J. Murphy, Croton-on-Hudson, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/551,538

(22) Filed: Nov. 24, 2014

(65) Prior Publication Data

US 2015/0082469 A1 Mar. 19, 2015

Related U.S. Application Data

(63) Continuation of application No. 13/795,765, filed on Mar. 12, 2013, now Pat. No. 8,962,913.

(60) Provisional application No. 61/660,976, filed on Jun. 18, 2012, provisional application No. 61/740,074, filed on Dec. 20, 2012.

(51) Int. Cl.
*A01K 67/027* (2006.01)
*A01K 67/02* (2006.01)
*C07K 14/54* (2006.01)

(52) U.S. Cl.
CPC ......... *A01K 67/0278* (2013.01); *C07K 14/5418* (2013.01); *A01K 2207/15* (2013.01); *A01K 2217/052* (2013.01); *A01K 2217/07* (2013.01); *A01K 2217/072* (2013.01); *A01K 2227/105* (2013.01); *A01K 2267/01* (2013.01); *A01K 2267/0331* (2013.01); *A01K 2267/0387* (2013.01); *A01K 2267/0393* (2013.01)

(58) Field of Classification Search
CPC ................ A01K 2227/105; A01K 2267/0331; A01K 2267/0387; A01K 2217/07; A01K 2217/072; A01K 67/0278; C12N 15/8509; A61K 38/19
USPC ............................................. 800/13, 18, 21
See application file for complete search history.

(56) References Cited

U.S. PATENT DOCUMENTS 7,759,541 B2 7/2010 Wolf et al.

FOREIGN PATENT DOCUMENTS

CN 101302517 A 11/2008
GB 2434578 A 8/2007

OTHER PUBLICATIONS

Silva et al. (2011) Cancer Res., vol. 71, 4780-4789.*
Lupton et al. (1990) J. Immunol., vol. 144, 3592-3601.*
Willinger et al. (2011) Trends in Immunology, vol. 32(7), 321-327.*
Clark et al. (2003) Nature Reviews: Genetics. vol. 4, 825-833.*
Niemann et al (2005) Rev. Sci, Tech. Off. Int. Spiz. vol. (24), 285-298.*
Wheeler (2001) Theriogenology. vol. 56, 1345-1369, p. 1351.*
Prelle et al. (2002) Anat. Histol. Embryol., vol. 31, 169-186.*
Munoz et al. (2009) Stem Cell Rev. and Rep., vol. 5, 6-9.*
Freeden-Jeffry et al., "Lymphopenia in Interleukin (IL)-7 Gene-deleted Mice Identifies IL-7 as a Nonredundant Cytokine," J. Exp. Med., 181: 1519-1526, 1995.
Fry et al., "A potential role for interleukin-7 in T-cell homeostasis," Blood, 97: 2983-2990, 2001.
Fry et al., "IL-7 comes of age," Blood, 107(1): 2587-2588, 2006.
Fry et al., "The Many Faces of IL-7: From Lymphopoiesis to Peripheral T Cell Maintenance," Journal of Immunology, 174: 6571-6576, 2005.
Fry, et al., "Interleukin-7: from bench to clinic," Blood, 99(11): 3892-3904, 2002.
Geiselhart et al., "IL-7 Administration Alters the CD4: CD8 Ratio, Increases T Cell Numbers, and Increases T Cell Function in the Absence of Activation," The Journal of Immunology, 166: 3019-3027, 2001.
Goodwin et al., "Human interleukin 7: Molecular cloning and growth factor activity on human and murine B-lineage cells," Proc. Natl. Acad. Sci. USA, 86: 302-306, 1989.
Guimond et al., "Cytokine Signals in T-Cell Homeostasis," J. Immunother, 28: 289-294, 2005.
Jacobs et al., "IL-7 Is Essential for Homeostatic Control of T Cell Metabolism In Vivo," The Journal of Immunology, 184: 3461-3469, 2010.
Kang et al., "Defective Development of •7β Cells in Interleukin 7 Receptor-deficient Mice Is Due to Impaired Expression of T Cell Receptor •Genes," J. Exp. Med., 190(7): 973-982, 1999.
Kieper et al., "Overexpression of Interleukin (IL)-7 Leads to IL-15-independent Generation of Memory Phenotype CD8 +T Cells," J. Exp. Med., 195(12): 1533-1539, 2002.
Lent et al., "IL-7 Enhances Thymic Human T Cell Development in "Human Immune System" Rag2-/-IL-2Ryc-/-Mice without Affecting Peripheral T Cell Homeostasis," The Journal of Immunology, 183: 7645-7655, 2009.
Lombard-Platet et al., "Expression of Functional MHC Class II Molecules by a Mouse Pro-B Cell Clone," Developmental Immunology, 4: 85-92, 1995.
Lupton et al., "Characterization of the Human and Murine IL-7 Genes," The Journal of Immunology, 144(9): 3592-3601, 1990.
Mahajan et al., "Homeostasis of T Cell Diversity," Cellular & Molecular Immunology, 2(1): 1-10, 2005.
Mazzucchelli et al., "Interleukin-7 receptor expression: intelligent design," Nature, 7: 144-154, 2007.
Mertsching et al., "IL-7 transgenic mice: analysis of the role of IL-7 in the differentiation of thymocytes in vivo and in vitro," International Immunology, 7(3): 401-414, 1995.
Munitic et al., "Dynamic regulation of IL-7 receptor expression is required for normal thymopoiesis," Blood, 104: 4165-4172, 2004.

(Continued)

*Primary Examiner* — Anne Marie S Wehbe
(74) *Attorney, Agent, or Firm* — Scully, Scott, Murphy & Presser, P.C.; Neil Miyamoto

(57) ABSTRACT

Genetically modified non-human animals comprising a human or humanized interleukin-7 (IL-7) gene. Cells, embryos, and non-human animals comprising a human or humanized IL-7 gene. Rodents that express human or humanized IL-7 protein. Genetically modified mice that comprise a human or humanized IL-7-encoding gene in their germline, wherein the human or humanized IL-7-encoding gene is under control of endogenous mouse IL-7 regulatory sequences.

26 Claims, 2 Drawing Sheets

(56) References Cited

OTHER PUBLICATIONS

Murphy et al., "Antitumor Effects of Interleukin-7 and Adoptive Immunotherapy on Human Colon Carcinoma Xenografts," J. Clin. Invest, 92: 1918-1924, 1993.
O'Connell et al., "Lentiviral Vector Delivery of Human Interleukin-7 (hIL-7) to Human Immune System (HIS) Mice Expands T Lymphocyte Populations," PLoS ONE, 5(8): 1-11, 2010.
Pleiman et al., "Organization of the Murine and Human Interleukin-7 Receptor Genes: Two mRNAs Generated by Differential Splicing and Presence of a Type I-Interferon-Inducible Promoter," Molecular and Cellular Biology, 11(6): 3052-3059, 1991.
Repass et al., "IL7-hCD25 and IL7-Cre BAC Transgenic Mouse Lines: New Tools for Analysis of IL-7 Expressing Cells," Genesis 47: 281-287, 2009.
Rich et al., "Cutaneous Lymphoproliferation and Lymphomas in Interleukin 7 Transgenic Mice," J. Exp. Med., 177: 305-316, 1993.
Samaridis et al., "Development of lymphocytes in intereleukin 7-transgenic mice," Eur. J. Immunol., 21: 453-460, 1991.
Schluns et al., "Interleukin-7 mediates the homeostasis of naive and memory CD8T cells in vivo," Nature Immunology, 1(5): 426-432, 2000.
Silva et al., "IL-7 Contributes to the Progression of Human T-cell Acute Lymphoblastic Leukemias," Cancer Research, 71(14): 4780-4789, 2011.
Tan et al., "IL-7 is critical for homeostatic proliferation and survival of naïve T cells," PNAS, 98(15): 8732-8737, 2001.
Uehira et al., "Immunologic Abnormalities Exhibited in IL-7 Transgenic Mice with Dermatitis," J. Invest Dermatol 110: 740-745, 1998.
Uehira et al., The development of dermatitis infiltrated by ∓ cells in IL-7 transgenic mice, International Immunology, 5 (12): 1619-1627, 1993.
Van De Wiele et al., "Impaired thymopoiesis in interleukin-7 receptor transgenic mice is not corrected by Bcl-2," Cellular Immunology, 250: 31-39, 2007.
Watanabe et al., "Interleukin 7 Transgenic Mice Develop Chronic Colitis with Decreased Interleukin 7 Protein Accumulation in the Colonic Mucosa," J. Exp. Med., 187(3): 389-402, 1998.
Williams, et al., "IL-7 Overexpression in Transgenic Mouse Keratinocytes Causes a Lymphoproliferative Skin Disease Dominated by Intermediate TCR Cells," The Journal of Immunology, 159: 3044-3056, 1997.
Rich et al., "Cuta,eous Lymphoproliferation and Lymphomas in Interleukin 7 Transgenic Mice" J. Exp. Med., vol. 177, pp. 305-316 (1993).
Fisher et al., "Lymphoproliferative disorders in an IL-7 transgenic mouse line" Leukemia, vol. 7(2), pp. 566-568, 1993.
Watanabe et al., "Interleukin 7 Transgeneic Mice Develop Chronic Colitis with Decreased Interleukin 7 Protein Accumulation in the Colonic Mucose" J. Exp. Med., vol. 187, pp. 389-402, 1998.
Rongvaux et al., "Human thrombopoietin knockin mice efficiently support human hematopoiesis in vivo" PNAS, vol. 108(6), pp. 2378-2383, 2011.
Willinger et al., "Human IL3/GM-CCF knock-in mice support human alveolar macrophage development and human immune responses in the lung" PNAS, vol. 108, pp. 2390-2395, 2011.
Anderson, "Post-transcriptional control of cytokine production" Nat. Immunol., vol. 9(4), pp. 353-359, 2008.
Carpenter et al., "Post-transcriptional regulation of gene expression in innate immunity" Nat. Reviews, vol. 14, pp. 361-376, 2014.
Silva et al., "IL-7 contributes to the pregression of human T-cell acute Lymphoblastic leukemias" Cancer Res., vol. 71, pp. 4780-4789, 2011.
Willinger et al., "Improving human hemato-lymphoid system mice in cytokine knock-in gene replacement" Trends in Immunobiology, vol. 32(7), pp. 321-327, 2011.
Lupton et al., "Characterixation of the human and murine IL-7 genes" J. Immunol., vol. 144, p. 3592-3601, 1990.
Clark et al., "A future for transgenic livestock" Nature Reviews: Genetics, vol. 4, pp. 825-833, 2003.
Munoz et al., "Constraints to Progress in Embryonic Stem Cells from Domestic Species" Stem Cell Rev. and Rep., vol. 5, pp. 6-9, 2009.
Wheeler et al., "Transgenic technology and Application in Swine" Theriogeneology, vol. 56, pp. 1345-1369, 2001.
Prelle et al., "Pluripotent Stem Cells—Model of Embryonic Development, tool for gene targeting, and basis of cell therapy" Anat. Histol. Embryol., vol. 31, pp. 169-186, 2002.
Niemann et al., "Transgenic farm animals: present and future" Rev. Sci. Tech. Off. Int. Spiz., vol. 24, pp. 285-298, 2005).
Van Lent, A.U. et al., "IL-7 enhances thymic human T cell development in "human immune system" Rag2-/-IL-2Rgammac-/-mice without affecting peripheral T cell homeostasis" The Journal of Immunology (Dec. 15, 2009) pp. 7645-7655, vol. 183, No. 12.
Anderson, P., "Post-transcriptional control of cytokine production" Nature Immunology (Apr. 2008) pp. 353-359, vol. 9, No. 4.
Carpenter, S. et al., "Post-transcriptional regulation of gene expression in innate immunity" Nature Reviews, Immunology (Jun. 2014) pp. 361-376, vol. 14.
Genebank Report, "Homo sapiens interleukin 7 (IL7), transcript variant 1, mRNA" NCBI Reference Sequence: NM_000880.3, dated May 4, 2014, 5 pages.
Genebank Report, "Mus musculus interleukin 7 (IL7), mRNA" NCBI Reference Sequence: NM_008371.4, dated May 4, 2014, 5 pages.
Campbell et al., "Neurologic disease induced in transgenic mice by cerebral overexpression of interleukin 6," Proc. Natl. Acad. Sci. USA, 90:10061-10065, 1993.
Dimitris et al., "The Pathophysiologic Roles of Interleukin-6 in Human Disease," Ann Intern Med., 128: 127-137, 1998.
Eisenbarth et al., "Development and Characterization of a Human IL-7 Transgenic Humanized Mouse Model," iwhm2, 2nd International Workshop on Humanized Mice, Program & Abstract Book, Sint Olofskapel, Amsterdam, The Netherlands, Apr. 3-6, 2009, Abstract #19.
Fattori et al., "IL-6 Expression in Neurons of Transgenic Mice Causes Reactive Astrocytosis and Increase in Ramified Microglial Cells but no Neuronal Damage," European Journal of Neuroscience, 7: 2441-2449, 1995.
Fattori, et al., "Development of Progressive Kidney Damage and Myeloma Kidney in Interleukin-6 Transgenic Mice," Blood, 83(9): 2570-2579, 1994.
Goya et al., "Sustained interleukin-6 signalling leads to the development of lymphoid organ-like structures in the lung," Journal of Pathology, 200: 82-87, 2003.
Heinrich et al., "Interleukin-6 and the acute phase response," Biochem. J., 265: 621-636,1990.
Hirano et al., "Biological and clinical aspects of interleukin 6," Immunology, 11: 443-449, 1990.
Hirano et al., "Complementary DNA for a novel human interleukin (BSF-2) that induces B lymphocytes to produce immunoglobulin," Nature, 324: 73-76, 1986.
Hirano et al., Purification to homogeneity and characterization of human B-cell differentiation factor (BCDF or BSFp-2), Proc. Natl. Acad. Sci. USA, 82: 5490-5494, 1985.
Hirota et al., "Continuous activation of gp130, a signal-transducing receptor component for interleukin 6-related cytokines, causes myocardial hypertrophy in mice," Proc. Natl. Acad. Sci. USA, 92: 4862-4866, 1995.
International Search Report for PCT/US2012/062379 (5 pages), May 3, 2013.
Keller et al., "Molecular and Cellular Biology of Interleukin-6 and its Receptor," Frontiers in Bioscience, 1: 340-357, 1996.
Kishimoto, Tadamitsu, "IL-6: from its discovery to clinical applications," International Immunology, 22(5): 347-352, 2010.
Kishimoto, Tadamitsu, "The Biology of Interleukin-6," Blood, 74(1): 1-10, 1989.
Kovalchuk et al., "IL-6 transgenic mouse model for extraosseous plasmacytoma," PNAS, 99(3): 1509-1514, 2002.
Maione et al., "Coexpression of IL-6 and soluble IL-6R causes nodular regenerative hyperplasia and adenomas of the liver," The EMBO Journal, 17(19): 5588-5597, 1998.
Naka et al., "The paradigm of IL-6: from basic science to medicine," Arthritis Research, 4(3): S233-S242, 2002.

(56) References Cited

OTHER PUBLICATIONS

Peters et al., "The Function of the Soluble Interleukin 6 (IL-6) Receptor In Vivo: Sensitization of Human Soluble IL-6 Receptor Transgenic Mice Towards IL-6 and Prolongation of the Plasma Half-life of IL-6," J. Exp. Med., 183: 1399-1406, 1996.
Rongvaux et al., "Human thrombopoietin knockin mice efficiently support human hematopoiesis in vivo," PNAS, 108 (6):2378-2383, 2011.
Suematsu et al., "Generation of plasmacytomas with the chromosomal translocation t(12;15) in interleukin 6 transgenic mice," Proc. Natl. Acad. Sci. USA, 89: 232-235, 1992.
Suematsu et al., "IgG1 plasmacytosis in interleukin 6 transgenic mice," Proc. Natl. Acad. Sci. USA, 86: 7547-7551, 1989.
Sugita et al., "Functional Murine Interleukin 6 Receptor with the Intracisternal a Particle Gene Product at its Cytoplasmic Domain," J. Exp. Med., 171: 2001-2009, 1990.
Tanabe et al., "Genomic Structure of the Murine IL-6 Gene—High Degree Conservation of Potential Regulatory Sequences between Mouse and Human," The Journal of Immunology, 141: 3875-3881, 1988.
Tsantikos et al., "Autoimmune Disease in Lyn-Deficient Mice is Dependent on an Inflammatory Environment Established by IL-6," The Journal of Immunology, 184: 1348-1360, 2010.
Tsujinaka et al., "Interleukin 6 Receptor Antibody Inhibits Muscle Atrophy and Modulates Proteolytic Systems in Interleukin 6 Transgenic Mice," J. Clin. Invest., 97(1): 244-249, 1996.
Tsujinaka et al., "Muscle Undergoes Atrophy in Associate with Increase of Lysosomal Cathepsin Activity in Interleukin-6 Transgenic Mouse," Biochemical and Biophysical Research Communication, 207(1): 168-174, 1995.
Ueda et al., "Novel genetically-humanized mouse model established to evaluate efficacy of therapeutic agents to human interleukin-6 receptor," Scientific Reports, 3(1196): 1-8, 2013.
Weissenbach et al., "Two interferon mRNAs in human fibroblasts: In vitro translation and *Escherichia coli* cloning studies," Proc. Natl. Acad. Sci. USA, 77(12): 7152-7156, 1980.
Willinger et al., "Human IL-3/GM-CSF knock-in mice support human alveolar macrophage development and human immune responses in the lung," PNAS, 108(6):2390-2395, 2011.
Woodroofe et al., "Long-Term Consequences of Interleukin-6 Overexpression in Transgenic Mice," DNA and Cell Biology, 11(8): 587-592, 1992.
Written Opinion for PCT/US2012/062379 (7 pages), mailed May 3, 2013.
Yamasaki et al., "Cloning and Expression of the Human Interleukin-6 (BSF-2/IFNBeta2)) Receptor," Science, 241: 825-828, 1988.
Yasukawa et al., "Structure and expression of human B cell stimulatory factor-2 (BSF-2/IL-6) gene," The EMBO Journal, 6(10): 2939-2945, 1987.
Zilberstein et al., "Structure and expression of cDNA and genes for human interferon-beta-2, a distinct species inducible by growth-stimulatory cytokines," The EMBO Journal, 5(10): 2529-2537, 1986.
Alves et al., "Characterization of the thymic IL-7 niche in vivo," Proceedings of the National Academy of Sciences, 106 (5): 1512-1517, 2009.
Fisher et al., "Lymphoprolierative Disorders in an IL-7 Transgenic Mouse Line," Leukemia, 7(02): 566-568, 1993.
International Search Report for PCT/US2013/045788 (6 pages), mailed Jul. 10, 2013.
Kim et al., "Seeing is Believing: Illuminating the Source of In Vivo Interleukin-7," Immune Network, 11(1): 1-7, 2011.
Mazzucchelli et al., "Visualization and Identification of IL-7 Producing Cells in Reporter Mice," PLOS ONE, 4(11): p. e7637, 2009.
O'Connell et al., "Lentiviral Vector Delivery of Human Interleukin-7 (hIL-7) to Human Immune System (HIS) Mice Expands T Lymphocyte Populations," PLOS ONE, 5(8): 1-10, 2010.
Repass et al., "IL7-hCD25 and IL7-Cre BAC transgenic mouse lines: New tools for analysis of IL-7 expressing cells," Genesis, 47(4): 281-287, 2009.
Shalapour et al., "Commensal microflora and interferon-[gamma] promote steady-state interleukin-7 production in vivo," European Journal of Immunology, 40(9): 2391-2399, 2010.
Written Opinion for PCT/US2013/045788 (9 pages), mailed Jul. 10, 2013.
Foss et al., "Frequent Expression of IL-7 Gene Transcripts in Tumor Cells of Classical Hodgkin's Disease," American Journal of Pathology, 146(1): 33-39, 1995.
"Rattus norvegicus interleukin 7 (IL7), mRNA" NCBI Reference Sequence: NM_013110.2 (Aug. 10, 2014) 2 pages.
"Interleukin-7 precursor [Rattus norvegicus]" NCBI Reference Sequence: NP_037242.2 (Aug. 10, 2014) 2 pages.
Kwitek, A.E. et al., "High-Density Rat Radiation Hybrid Maps Containing Over 24,000 SSLPs, Genes, and ESTs Provide a Direct Link to the Rat Genome Sequence" Genome Research (2004) pp. 750-757, vol. 14.
Visse, E. et al., "Regression of intracerebral rat glioma isografts by therapeutic subcutaneous immunization with interferon-gamma, interleukin-7, or B7-1-transfected tumor cells" Cancer Gene Therapy (1999) pp. 37-44, vol. 6, No. 1.
Zhou, Q. et al., "Generation of Fertile Cloned Rats by Regulating Oocyte Activation" Science (Nov. 14, 2003) pp. 1179, vol. 302.
Tong, C. et al., "Production of p53 gene knockout rats by homologous recombination in embryonic stem cells" Nature (Sep. 9, 2010) pp. 211-215, vol. 467.
Kim, G.V., et al., "Seeing Is Believing: Illuminating the Source of In Vivo Interleukin-7" Immune Network 11 (1):1-10 (2011).
European Search Report mailed Mar. 18, 2015, issued in Application No. EP 14 19 5502.
Chinese Office Action dated Aug. 28, 2015 received from Application No. 201380031333.4, together with an English-language translation.

* cited by examiner

HUMANIZED IL-7 RODENTS

CROSS-REFERENCE TO RELATED APPLICATIONS

This application is a continuation of U.S. patent application Ser. No. 13/795,765, filed Mar. 12, 2013, which claims the benefit under 35 USC §119(e) of U.S. Provisional Application No. 61/660,976 filed 18 Jun. 2012, and U.S. Provisional Application No. 61/740,074 filed on 20 Dec. 2012, all of which are hereby incorporated by reference.

FIELD

Non-human animals (e.g., mammals, e.g., rodents such as mice, rats, and hamsters) that comprise a genetic modification comprising a replacement, at an endogenous locus, of a non-human IL-7 gene sequence with a human IL-7 gene sequence. Rodents and other non-human animals that express human IL-7 or humanized IL-7 from a locus under control of endogenous non-human regulatory sequences, or from an endogenous non-human IL-7 locus that comprises endogenous non-human regulatory sequences.

BACKGROUND

Transgenic mice that have randomly inserted transgenes that contain a human IL-7 sequence are known in the art. However, most if not all of these transgenic mice are not optimal in one aspect or another. For example, most mice transgenic for human IL-7 exhibit abnormal levels and/or ratios of certain cells, including T cells, that are likely due to a dysregulation of immune cell development, e.g., T cell development.

There remains a need in the art for non-human animals that comprise human IL-7-encoding sequences, wherein the human IL-7 encoding sequences are at an endogenous non-human IL-7 locus, and for non-human animals that express human IL-7 under the control of endogenous non-human regulatory elements. There is a need in the art for non-human animals that express human IL-7 in a manner that is as physiologically relevant in the non-human animal as possible. There is a need in the art for non-human animals that express a human IL-7, wherein the non-human animals lack a significant abnormality in peripheral T cells, and/or in ratios of T cell subtypes.

SUMMARY

Genetically modified non-human animals, cells, tissues, and nucleic acids are provided that comprise a human IL-7 genomic sequence at an endogenous non-human IL-7 locus. The non-human animals express a humanized IL-7 protein from a modified locus regulated by one or more endogenous non-human regulatory sequences of the modified endogenous IL-7 locus. In various embodiments, the non-human animals are rodents, e.g., mice, rats, hamsters, etc. In a specific embodiment, the rodent is a mouse or a rat.

In various embodiments and aspects, the non-human animals comprise a modified IL-7 gene in the germline of the non-human animal at a modified endogenous IL-7 locus, wherein the modified endogenous IL-7 locus comprises a humanization of at least a portion of the endogenous IL-7 gene. In various embodiments, the mice are heterozygous or homozygous with respect to the modified IL-7 locus. In one embodiment, a non-human animal is provided that comprises a lack of a first endogenous IL-7 allele and a humanization of a second endogenous IL-7 allele. In various embodiments and aspects, the humanization is of one or more exons and/or introns. In various embodiments and aspects, non-human animals having a modified IL-7 locus are provided wherein one or both of an endogenous non-human 5'-untranslated region and an endogenous non-human 3'-untranslated region are retained in the modified animal.

In one aspect, a genetically modified rodent is provided that comprises a replacement at an endogenous rodent IL-7 locus of an endogenous rodent IL-7 genomic sequence with a human IL-7 genomic sequence.

In one embodiment, the genetically modified rodent comprises a first rodent regulatory sequence upstream (with respect to the direction of transcription of the IL-7 gene) of the human IL-7 genomic sequence and a second rodent regulatory sequence downstream of the human IL-7 genomic sequence. In one embodiment, the first rodent regulatory sequence comprises a rodent promoter and/or enhancer, and the second rodent regulatory sequence comprises a 3'-UTR.

In one embodiment, the rodent is a mouse and comprises an endogenous mouse IL-7 gene locus having a mouse exon 1 and human exons 2, 3, 4, 5, and 6. In one embodiment, the endogenous mouse IL-7 gene locus comprises, from upstream to downstream with respect to the direction of transcription, mouse exon 1, at least a portion of a first mouse intron, and a contiguous human genomic fragment comprising human exon 2 through human exon 6. In one embodiment, the mouse further comprises a contiguous sequence of endogenous mouse DNA comprising an complete endogenous mouse IL-7 upstream (with respect to the direction of transcription of the IL-7 gene) promoter and regulatory region, wherein the contiguous mouse DNA is upstream of the human genomic fragment; and further comprises a contiguous sequence of endogenous mouse DNA 3'-UTR downstream of the human genomic fragment.

In one embodiment, the mouse comprises a mouse sequence that is at least 90%, at least 95%, at least 96%, at least 97%, at least 98%, or at least 99% identical with a sequence selected from SEQ ID NO:1, SEQ ID NO:2, and a combination thereof. In a specific embodiment, the mouse comprises a mouse sequence selected from SEQ ID NO:1 and SEQ ID NO:2.

In one aspect, a genetically modified mouse is provided that comprises a replacement at an endogenous mouse IL-7 locus of an endogenous mouse IL-7 genomic sequence with a human IL-7 genomic sequence to form a modified locus, wherein the human IL-7 genomic sequence comprises at least one human exon, and the modified locus comprises a mouse sequence selected from a sequence of SEQ ID NO:1, SEQ ID NO:2, and a combination thereof.

In one embodiment, the replacement comprises a human genomic fragment comprising exons 2 through 6, and the human genomic fragment is linked to mouse exon 1 to form a modified endogenous mouse IL-7 locus, wherein the modified mouse IL-7 locus comprises a mouse sequence selected from SEQ ID NO:1, SEQ ID NO:2, and a combination thereof.

In one aspect, a genetically modified rodent is provided that comprises an IL-7 gene that comprises a rodent exon 1 and at least a portion of a rodent intron 1, and a human IL-7 gene sequence of human IL-7 exons 2, 3, 4, 5, and 6, wherein the rodent comprises a sequence selected from a rodent upstream IL-7 regulatory sequence, a rodent IL-7 3'-UTR, and a combination thereof.

In one aspect, a genetically modified mouse is provided that comprises a sequence selected from SEQ ID NO:1, SEQ ID NO:2, and a combination thereof; wherein the mouse lacks an endogenous sequence encoding exons 2 through 5 of a mouse IL-7 protein, and the mouse comprises a nucleic acid sequence at an endogenous mouse IL-7 locus wherein the nucleic acid sequence encodes human IL-7 exons 2, 3, 4, 5, and 6.

In one aspect, a genetically modified rodent is provided that expresses a human or humanized IL-7 protein from an endogenous rodent IL-7 locus that is modified to express at least one human IL-7 exon. In one embodiment, the rodent IL-7 locus is modified to express a human or humanized iL7 protein encoded by a sequence comprising at least two human IL-7 exons. In one embodiment, the rodent IL-7 locus is modified to express a human or humanized IL-7 protein encoded by a sequence comprising at least three human IL-7 exons. In on embodiment, the rodent IL-7 locus is modified to express a human or humanized IL-7 protein encoded by a sequence comprising at least human IL-7 exons 2, 3, 4, 5, and 6 (i.e., 2 through 6). In one embodiment, the rodent IL-7 locus is modified to express a human IL-7 protein.

In one aspect, a genetically modified rodent is provided that expresses a human or humanized IL-7 protein from an endogenous mouse IL-7 locus that is modified to comprise at least human IL-7 exons 2 through 6 in place of mouse IL-7 exons 2 through 5.

In one aspect, a genetically modified rodent is provided that expresses a human or humanized IL-7 protein from a humanized endogenous rodent IL-7 locus comprising a humanized endogenous rodent IL-7 coding region, wherein the humanized endogenous rodent IL-7 locus comprises all endogenous rodent regulatory elements that are present in a wild-type rodent upstream of a wild-type rodent IL-7 coding region and that are downstream of the wild-type rodent IL-7 coding region.

In one aspect, a genetically modified rodent is provided that expresses a human or humanized IL-7 protein from a humanized rodent IL-7 locus that comprises rodent regulatory regions upstream and downstream of a nucleic acid sequence encoding the human or humanized IL-7 protein, wherein the human or humanized IL-7 protein is expressed in an expression pattern that is about the same as the expression pattern of a rodent IL-7 protein in a wild-type rodent. In one embodiment, the level of serum expression of the human or humanized IL-7 is about the same as the level of serum expression of a rodent IL-7 protein in a wild-type rodent.

In one aspect, a genetically modified rodent is provided that expresses a humanized IL-7 protein, wherein the lymphocyte population of the rodent is characterized by its B cell population that is about the same in number as a population of B cells in an age-matched wild-type mouse. In one embodiment, the modified rodent is characterized by a population of mature B cells that is about the same in number as a population of mature B cells in an age-matched wild-type mouse. In one embodiment, the humanized IL-7 protein is identical to a human IL-7 protein. In one embodiment, the humanized IL-7 protein comprises human sequence encoded by at least exons 2 through 6 of a human IL-7 gene.

In one aspect, a genetically modified rodent is provided that expresses a humanized IL-7 protein, wherein the lymphocyte population of the rodent is characterized by a population of T cells that is about the same in number as a population of T cells in an age-matched wild-type mouse. In one embodiment, the modified rodent exhibits a population of mature T cells that is about the same in number as a population of mature T cells in an age-matched wild-type mouse. In one embodiment, the modified rodent exhibits a population of peripheral T cells that is about the same in number as the population of peripheral T cells in an age-matched wild-type mouse. In one embodiment, the humanized IL-7 protein is identical to a human IL-7 protein. In one embodiment, the humanized IL-7 protein comprises human sequence encoded by at least exons 2 through 6 of a human IL-7 gene.

In one aspect, a genetically modified rodent is provided that expresses a humanized IL-7 protein, wherein the lymphocyte population of the rodent is characterized by a T cell population that exhibits a CD4:CD8 ratio that is about the same as the CD4:CD8 ratio in the T cell population of an age-matched wild-type mouse. In one embodiment, the humanized IL-7 protein is identical to a human IL-7 protein. In one embodiment, the humanized IL-7 protein comprises human sequence encoded by at least exons 2 through 6 of a human IL-7 gene.

In one aspect, a genetically modified rodent is provided that expresses a humanized IL-7 protein, wherein the rodent comprises a characteristic selected from a lack of a propensity to develop a chronic colitis; lack of over-expression of IL-7 in colonic mucosal lymphocytes; normal, or wild-type, expression of IL-7 in colonic mucosal lymphocytes; lacks a severe dermatitis; lacks a dermatitis characterized by a massive dermal infiltration of mononuclear cells; exhibits a CD4:CD8 ratio in its T cell population that is about the same as the CD4:CD8 ratio of an age-matched wild-type mouse; exhibits an expression pattern of human IL-7 that is about the same as an expression pattern of mouse IL-7 in a wild-type mouse; and a combination thereof.

In one aspect, a genetically modified rodent is provided that expresses a humanized IL-7 protein, wherein the rodent lacks a propensity to develop a chronic colitis.

In one aspect, a genetically modified rodent is provided that expresses a humanized IL-7 protein, wherein the rodent does not exhibit over-expression of IL-7 in colonic mucosal lymphocytes.

In one aspect, a genetically modified rodent is provided that expresses a humanize IL-7 protein, wherein the rodent does not exhibit a dermatitis characterized by a massive dermal infiltration of mononuclear cells.

In one aspect, a genetically modified rodent is provided that expresses a humanized IL-7 protein, wherein the rodent does not exhibit a lymphoproliferation into dermis.

In one aspect, a genetically modified rodent is provided that expresses a humanized IL-7 protein, wherein the rodent does not exhibit B and/or T cell lymphomas at a higher frequency than an age-matched wild-type mouse.

In one aspect, a genetically modified mouse is provided that expresses a humanized IL-7 protein, or a human IL-7 protein, wherein the mouse is no more prone than a wild-type mouse to developing a pathology selected from colitis, chronic colitis, severe dermatitis, pathological and/or massive infiltration of the dermis by mononuclear cells, lymphoproliferation of the dermis, B cell lymphomas, T cell lymphomas, reduction in the number of mature B and/or T cells, reduction in the number of peripheral B and/or T cells, abnormal numbers of CD4+ T cells, abnormal numbers of CD8+ T cells, and a combination thereof.

In one aspect, a genetically modified non-human animal is provided, comprising in its germline a replacement of at least one non-human IL-7 exon with at least one human IL-7 exon to form a human or humanized IL-7-encoding gene, wherein the replacement is at an endogenous non-human IL-7 locus, wherein the human or humanized IL-7-encoding gene is under control of endogenous non-human regulatory elements.

In one embodiment, the genetically modified non-human animal is a rodent. In one embodiment, the rodent is selected from a rat and a mouse.

In on embodiment, the human or humanized IL-7-encoding gene comprises human exons selected from the group consisting of human exon 1, human exon 2, human exon 3, human exon 4, human exon 5, human exon 6, and a combination thereof. In one embodiment, the human or humanized IL-7-enconding gene comprises no more than five human exons.

In one embodiment, the genetically modified non-human animal is a rodent that is a mouse and the modified locus comprises a replacement of mouse exons 2, 3, 4, and 5 with a human genomic segment comprising human IL-7 exons 2, 3, 4, 5, and 6.

In one embodiment, the human or humanized IL-7-encoding gene comprises a cDNA encoding a human or humanized IL-7 protein.

In one aspect, a genetically modified non-human animal is provided, comprising in its germline a transgene comprising a nucleic acid sequence encoding a human or humanized IL-7 gene, wherein the human or humanized IL-7 gene is flanked upstream and downstream with endogenous non-human regulatory sequences.

In one embodiment, the genetically modified non-human animal is a rodent. In one embodiment, the rodent is selected from the group consisting of a mouse, a rat, and a hamster.

In one embodiment, the genetically modified non-human animal comprises a human exon selected from the group consisting of human exon 1, human exon 2, human exon 3, human exon 4, human exon 5, human exon 6, and a combination thereof. In one embodiment, the human or humanized IL-7 gene comprises at least five human exons.

In one aspect, a method is provided for making a non-human animal with a human or humanized IL-7-encoding gene, comprising modifying the germline of the non-human animal to comprise a human or humanized IL-7-encoding gene flanked upstream and downstream with endogenous non-human IL-7 regulatory sequences.

In one embodiment of the method, the modification is at an endogenous non-human IL-7 locus.

In one embodiment of the method, the non-human animal is a rodent. In one embodiment, the rodent is selected from the group consisting of a mouse, a rat, and a hamster.

In one aspect, a genetically modified non-human animal is provided that is genetically modified to express human IL-7 in an expression pattern that is the same expression pattern as observed for a wild-type non-human animal of the same genus and species. In one embodiment, the non-human animal is a rodent. In a specific embodiment, the rodent is selected from a mouse and a rat.

In one embodiment, the genetically modified non-human animal of claim 17, wherein the level of human IL-7 expressed in the non-human animal is about the same as the level of non-human IL-7 in a corresponding wild-type mouse. In one embodiment, the non-human animal is a rodent. In a specific embodiment, the rodent is selected from a mouse and a rat.

In one aspect, a DNA construct is provided, comprising from 5' to 3' with respect to direction of transcription, a nucleic acid sequence homologous to a mouse IL-7 5' noncoding sequence, a human genomic fragment encoding a human IL-7 protein but not comprising a human regulatory sequence upstream or downstream of sequence encoding the human IL-7 protein, and a nucleic acid sequence homologous to a mouse IL-7 3' noncoding sequence.

In one aspect, a DNA construct is provided, comprising from 5' to 3' with respect to direction of transcription, a nucleic acid sequence that comprises a region of homology to a mouse IL-7 exon 1 sequence, a human genomic fragment encoding a human IL-7 protein but not comprising a human regulatory sequence upstream or downstream of sequence encoding the human IL-7 protein, and a nucleic acid sequence homologous to a mouse IL-7 3' noncoding sequence.

In one aspect, a genetically modified rodent cell is provided, wherein the rodent cell comprises a replacement at an endogenous rodent IL-7 locus of a gene sequence encoding a rodent IL-7 with a human genomic sequence encoding a human IL-7.

In one embodiment, the human genomic sequence comprises a contiguous human nucleic acid sequence spanning human IL-7 exons 2 through human IL-7 exon 6.

In one embodiment, the genetically modified rodent comprises a mouse IL-7 promoter at the endogenous rodent IL-7 locus.

In one embodiment, the cell is selected from a pluripotent cell, an induced pluripotent cell, a totipotent cell, an ES cell, and an ovum.

In one embodiment, the cell secretes human IL-7. In one embodiment, the cell that secretes human IL-7 is selected from an epithelial cell (e.g., an intestinal epithelial cell), a hepatocyte, a keratinocyte, a dendritic cell, and a follicular dendritic cell. In one embodiment, the rodent cell is a bone marrow dendritic cell. In one embodiment, the cell that secretes human IL-7 is a thymic stromal cell; in a specific embodiment, the thymic stromal cell is a cortical epithelial cell.

In one aspect, a rodent embryo is provided, wherein the embryo comprises at least one rodent donor cell (e.g., an ES cell, a pluripotent cell, a totipotent cell, etc.) comprising a replacement of an endogenous rodent IL-7-encoding nucleic acid sequence with a nucleic acid sequence encoding a human IL-7 at the endogenous rodent IL-7 locus. In one embodiment, the donor cell is a mouse ES cell and the embryo is a host mouse embryo that is a pre-morula, a morula, or a blastocyst.

In one aspect, a rodent tissue that comprises a humanized IL-7 gene at an endogenous rodent IL-7 locus is provided, wherein the rodent tissue is selected from thymic, splenic, epidermal, and intestinal.

In one aspect, a genetically modified mouse is provided that comprises a DNA sequence that encodes a human IL-7, wherein the mouse does not express a mouse IL-7, and wherein the mouse exhibits a T cell population that is about the same size as the T cell population of a wild-type mouse.

In one embodiment, the mouse exhibits a peripheral T cell population that is about the same size as a peripheral T cell population of a wild-type mouse.

In one embodiment, the T cell population is a mouse T cell population.

In one embodiment, the mouse is not more prone than a wild-type mouse to develop a B cell tumor comprising a pro-B or a pre-B cell.

In one embodiment, the mouse is not more prone than a wild-type mouse to develop a lymphoid tumor.

In one embodiment, the mouse does not exhibit a lymphoproliferative disorder in the absence of a known lymphoproliferative causative agent.

In one embodiment, the mouse does not exhibit a pathologic infiltration of T cell in a skin layer. In one embodiment, the mouse does not exhibit a symptom of alopecia.

In one embodiment, the majority of T cells of the genetically modified mouse are about the same in size distribution as in an age-matched wild-type mouse. In a specific embodiment, the genetically modified mouse does not exhibit an enlargement of T cell In one aspect, a rodent is provided that expresses a humanized or human IL-7 protein from an endogenous modified rodent IL-7 locus, wherein the serum concentration of human IL-7 in the rodent is physiologically normal.

In one aspect, a humanized rodent is provided that expresses a humanized IL-7 gene in the serum of the rodent at a physiologically normal concentration.

In one embodiment, the rodent is selected from a mouse and a rat.

In one embodiment, the physiologically normal serum concentration of human IL-7 is less than 10 picograms/mL. In one embodiment, the physiologically normal serum concentration of human IL-7 is less than 5 picograms/mL. In one embodiment, the physiologically normal serum concentration of human IL-7 in the rodent is about 2 picograms/mL to about 4 picograms/mL. In one embodiment, the physiologically normal serum concentration of human IL-7 in the rodent serum is about 2.4 picograms/mL to about 3.2 picograms/mL.

In one aspect, a method for making a human IL-7 protein is provided, comprising inserting into the germline of the non-human animal a human or humanized IL-7 coding gene under control of endogenous non-human regulatory elements, allowing the non-human animal to make the human or humanized IL-7, and isolating from the non-human animal (e.g., a mammal, e.g., a rodent such as, e.g., a mouse or rat or hamster) human or humanized IL-7.

In one aspect, a method for making a human IL-7 protein is provided, comprising isolating from a non-human animal as described herein (e.g., a mammal, e.g., a rodent such as, e.g., a mouse or rat or hamster).

In one aspect, a method is provided for making a non-human animal that comprises a human or humanized IL-7 gene in its germline, comprising inserting into the germline of the non-human animal a human or humanized IL-7-encoding nucleic acid sequence or fragment thereof, wherein the human or humanized IL-7-coding nucleic acid sequence or fragment thereof is under regulatory control of endogenous non-human regulatory elements. In one embodiment, the human or humanized IL-7 gene is at an endogenous non-human IL-7 locus (i.e., inserted between upstream and downstream non-human regulatory elements at the endogenous non-human IL-7 locus, wherein the human or humanized IL-7-coding nucleic acid sequence replaces the wild-type existing non-human IL-7 coding sequence in whole or in part). In one embodiment, the non-human animal is a mammal, e.g., rodent. In one embodiment, the rodent is selected from a mouse, a rat, and a hamster.

In one aspect, a method is provided for isolating from a non-human animal a T cell that has been exposed to a human or humanized IL-7 protein, comprising a step of isolating a T cell from a non-human animal as described herein. In one embodiment, the non-human animal is a mouse or a rat. In one embodiment, the T cell is a non-human T cell, e.g., a rodent T cell, e.g., a T cell of a mouse or a rat. In one embodiment, the T cell is selected from a T cell in the thymus and a peripheral T cell.

In one aspect, a method for identifying an agent that is an antagonist of human IL-7 is provided, comprising a step of administering an agent to a genetically modified rodent as described herein, determining an effect of the agent on a human IL-7 mediated function in the rodent, and identifying the agent as an IL-7 antagonist if it antagonizes the function of human IL-7 in the genetically modified rodent.

In one embodiment, the agent comprises an immunoglobulin variable domain that binds IL-7. In one embodiment, the agent specifically binds human IL-7 but not rodent IL-7. In one embodiment, the agent is an antibody.

In one aspect, a method for determining whether an agent reduces IL-7-mediated peripheral T cell population is provided, comprising a step of administering to a genetically modified rodent as described herein an IL-7 antagonist for a period of time, measuring peripheral T cell population number of the rodent at one or more time periods following administration, and determining whether the IL-7 antagonist reduces the peripheral T cell population.

In one aspect, the genetically modified non-human animal is heterozygous for a human or humanized IL-7-encoding gene. In one embodiment, the non-human animal is unable to express an endogenous IL-7 protein. In a specific embodiment, the non-human animal comprises a knockout of both endogenous IL-7 alleles.

Each of the aspects and embodiments described above and below may be used together, unless otherwise stated and unless otherwise clear from the context.

DETAILED DESCRIPTION

Figure 1:
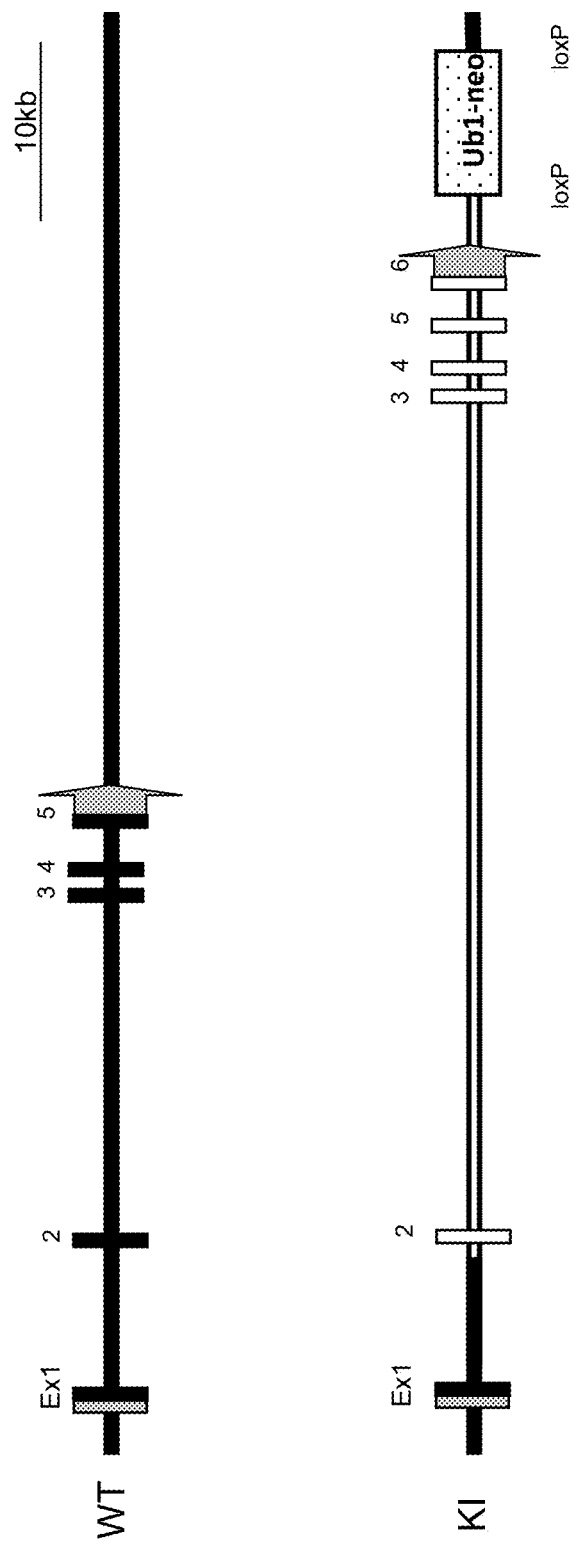
FIG. 1 depicts (not to scale) a schematic of a wild-type mouse IL7 gene locus (top) and a humanized endogenous mouse IL-7 locus (bottom). Open symbols indicate human sequence; closed symbols indicate mouse sequence; shaded items indicate untranslated regions; stippled region indicates other sequence.

In various embodiments, non-human animals are described that comprise the genetic modification(s) described herein. The genetically modified non-human animal may be selected from a group consisting of a mouse, rat, rabbit, pig, bovine (e.g., cow, bull, buffalo), deer, sheep, goat, chicken, cat, dog, ferret, primate (e.g., marmoset, rhesus monkey). For the non-human animals where suitable genetically modifiable ES cells are not readily available, other methods are employed to make a non-human animal comprising the genetic modification. Such methods include, e.g., modifying a non-ES cell genome (e.g., a fibroblast or an induced pluripotent cell) and employing nuclear transfer to transfer the modified genome to a suitable cell, e.g., an oocyte, and gestating the modified cell (e.g., the modified oocyte) in a non-human animal under suitable conditions to form an embryo.

In one aspect, the non-human animal is a mammal. In one aspect, the non-human animal is a small mammal, e.g., of the superfamily Dipodoidea or Muroidea. In one embodiment, the genetically modified animal is a rodent. In one embodiment, the rodent is selected from a mouse, a rat, and a hamster. In one embodiment, the rodent is selected from the superfamily Muroidea. In one embodiment, the genetically modified animal is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, Malagasy rats and mice), Platacanthomyidae (e.g., spiny dormice), and Spalacidae (e.g., mole rates, bamboo rats, and zokors). In a specific embodiment, the genetically modified rodent is selected from a true mouse or rat (family Muridae), a gerbil, a spiny mouse, and a crested rat. In one embodiment, the genetically modified mouse is from a member of the family Muridae. In one embodiment, the animal is a rodent. In a specific embodiment, the rodent is selected from a mouse and a rat. In one embodiment, the non-human animal is a mouse.

In various embodiments, the non-human animal is a rodent that is a mouse of a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/Ola. In another embodiment, the mouse is a 129 strain selected from the group consisting of a strain that is 129P1, 129P2, 129P3,129X1, 129S1 (e.g., 129I/SV, 129I/SvIm), 129S2, 129S4, 129S5, 129S9/SvEvH, 129S6 (129/SvEvTac), 129S7, 129S8, 129T1, 129T2 (see, e.g., Festing et al. (1999) Revised nomenclature for strain 129 mice, Mammalian Genome 10:836, see also, Auerbach et al (2000) Establishment and Chimera Analysis of 129/SvEv- and C57BL/6-Derived Mouse Embryonic Stem Cell Lines). In a specific embodiment, the genetically modified mouse is a mix of an aforementioned 129 strain and an aforementioned C57BL/6 strain. In another specific embodiment, the mouse is a mix of aforementioned 129 strains, or a mix of aforementioned BL/6 strains. In a specific embodiment, the 129 strain of the mix is a 129S6 (129/SvEvTac) strain. In another embodiment, the mouse is a BALB strain, e.g., BALB/c strain. In one embodiment, the mouse is a mix of a BALB strain and another aforementioned strain.

In one embodiment, the non-human animal is a rat. In one embodiment, the rat is selected from a Wistar rat, an LEA strain, a Sprague Dawley strain, a Fischer strain, F344, F6, and Dark Agouti. In one embodiment, the rat strain is a mix of two or more strains selected from the group consisting of Wistar, LEA, Sprague Dawley, Fischer, F344, F6, and Dark Agouti.

Genetically modified non-human animals that comprise a replacement of a non-human IL-7 gene sequence with a human IL-7 gene sequence are provided. Rodents that comprise a humanization of an IL-7 gene, at an endogenous rodent IL-7 locus, are provided. Methods for making rodents, e.g., mice, that comprise a replacement of an endogenous IL-7 gene or fragment thereof (e.g., a fragment comprising one or more exons) with a humanized IL-7 gene, or fragment thereof (e.g., a fragment comprising one or more exons), at the endogenous IL-7 locus. Cells, tissues, and mice are provided that comprise the humanized gene are provided, as well as cells, tissues, and mice that express human IL-7 from an endogenous non-human IL-7 locus.

IL-7 is a cytokine that is essential for development of immature B and T cells and, to some degree, mature T cells; IL-7 knockout mice display a severe depletion of mature B and T cells (von Freeden-Jeffry U. et al. (1995) Lymphopenia in interleukin (IL)-7 gene-deleted mice identifies IL-7 as a nonredundant cytokine, J. Exp. Med. 181:1519-1526). The depletion is apparently due to a block between pro-B and pre-B cells, and a block in T cell proliferation (rather than a block in T cell differentiation; ratios of T cell types in IL-7 KO mice are about normal) that results in a depressed population of T cells and mature B cells (Id.). IL-7 is produced by epithelial cells in the thymus and intestine, in keratinocytes, liver, and dendritic cells—but not by normal lymphocytes (reviewed, e.g., in Fry T. J. and Mackall, C. L. (2002) Interleukin-7: from bench to clinic, Blood 99(11):3892-3904).

Simply put, IL-7 increases T cell number and enhances T cell function (see, e.g., Morrissey, J. J. (1991) Administration of IL-7 to normal mice stimulates B-lymphopoiesis and peripheral lymphadenopathy, J. Immunol. 147:561-568; Faltynek, C. R. et al. (1992) Administration of human recombinant IL-7 to normal and irradiated mice increases the numbers of lymphocytes and some immature cells of the myeloid lineage, J. Immunol. 149:1276-1282; Risdon, G. J. et al. (1994) Proliferative and cytotoxic responses of human cord blood T lymphocytes following allegenic stimulation, Cell. Immunol. 154:14-24). Functional enhancement of T cells can be achieved by a short duration of IL-7 exposure, whereas increases in T cell number reflect a proliferative effect that is achieved with a longer duration exposure (Geiselhart, L. A. et al. (2001) IL-7 Administration Alters the CD4:CD8 Ratio Increases T Cell Numbers, and Increases T Cell Function in the Absence of Activation, J. Immunol. 166:3019-3027; see also, Tan J. T. et al. (2001) IL-7 is critical for homeostatic proliferation and survival of naïve T cells, Proc. Natl. Acad. Sci. USA 98(15):8732-8737).

IL-7 is necessary for both early and late stage T cell regulation. IL-7 is not expressed by T cells, which must encounter IL-7 that is released by non-thymic cells in the periphery and that is believed to be responsible for peripheral T cell proliferation and maintenance (reviewed, e.g., in Guimond, M (2005) Cytokine SIgnals in T-Cell Homeostasis, J. Immunother. 28(4):289-294). IL-7 starvation results in severely impaired T cell development and survival of naïve T cells. IL-7 also appears to be necessary for the survival of mature T cells; mature T cells acquired through adoptive transfer into IL-7-deficient mice enter apoptosis where the mice lack an IL-7 gene, but not in mice that express IL-7 that lack an IL-7R gene (Schluns, K. S. et al. (2000) Interleukin-7 mediates the homeostasis of naïve and memory CD8 T cells in vivo, Nat. Immunol. 1(5):426-432. Loss of IL-7 function results in a SCID-like phenotype in mice (Puel, A. and Leonard, W. J. (2000) Mutations in the gene for the IL-7 receptor result in T(−)B(+)NK(+) severe combined immunodeficiency disease, Curr. Opin. Immunol. 12:468-473), presumably due to T cell atrophy and death caused by diminished growth rate likely mediated by glycolytic insufficiency in the absence of IL-7 stimulus (Jacobs, S. R. et al. (2010) IL-7 Is Essential for Homeostatic Control of T Cell Metabolism In Vivo, J. Immunol. 184:3461-3469).

The human IL-7 gene comprises 6 exons that extend over 33 kb and is located on chromosome 8 at 8q12-13. Mouse IL-7 comprises 5 exons (there is no counterpart in mouse to human exon 5) and is about 80% homologous to the human gene; analysis of non-coding sequences of the human and the mouse genes revealed a paucity of recognizable regulatory motifs responsible for transcription and regulation of gene expression (Lupton, S. D. et al. (1990) Characterization of the Human and Murine IL-7 Genes, J. Immunol. 144(9):3592-3601), suggesting that regulation of IL-7 expression may be complex. However, mouse BAC fragments comprising a reporter gene at the hIL-7 locus have been expressed in mice to successfully ascertain expression patterns of IL-7 in mice (see, e.g., Avles, N. L. et al. (2009) Characterization of the thymic IL-7 niche in vivo, Proc. Natl. Acad. Sci. USA 106 (5):1512-1517; Mazzucchelli, R. I. (2009) Visualization and Identification of IL-7 Producing Cells in Reporter Mice, PLoS ONE 4(11):e7637; Repas, J. F. et al. (2009) IL7-hCD25 and IL7-Cre BAC transgenic mouse lines: new tools for analysis of IL-7 expressing cells, Genesis 47:281-287). In at least one case, a BAC-based replacement of an IL-7 exon with a reporter required the entire 43 kb IL-7 locus as well as 96 kb of 5' flanking sequence and 17 kb of 3' flanking sequence in the hope of faithfully recapitulating IL-7 expression of wild-type mice (Repass, J. F. et al. (2009)). In any case, data from the different studies on reporter expression driven by putative IL-7 regulatory elements vary somewhat from one another and from earlier observations, supporting an inference that IL-7 regulation might not have been faithfully recapitulated in these reporter mice (IL-7 reporter transgenic mice are reviewed in Kim, G. Y. et al. (2011) Seeing Is Believing: Illuminating the Source of In Vivo Interleukin-7, Immune Network 11(1):1-10). Human IL-7 is functional on mouse cells, but mouse IL-7 is not functional on human cells.

Transgenic mice that express abnormally or poorly regulated human IL-7 exhibit a panoply of pathologies or syndromes. Mice transgenic for a murine IL-7 cDNA under control of mouse Ig heavy chain enhancer, x light chain enhancer, and light chain promoter) to target expression in the lymphoid compartment) exhibit significantly enhanced numbers of B cell precursors and an overall expansion of all subsets of thymocytes in the thymus and peripheral T cells (Samaridis, J. et al. (1991) Development of lymphocytes in interleukin 7-transgenic mice, Eur. J. Immunol. 21:453-460).

Transgenic mice that express IL-7 from a mouse cDNA under control of an SRα promoter develop a panoply of pathologies, including a chronic colitis that histopathologically mimics chronic colitis in humans, and is characterized by at least a transient over-expression of IL-7 in colonic mucosal lymphocytes (but not colonic epithelial cells) and its apparent accumulation in mucus of goblet cells of the colonic mucosa (Watanabe, M. et al. (1998) Interleukin 7 Transgenic Mice Develop Chronic Colitis with Decreased Interleukin 7 Protein Accumulation in the Colonic Mucosa, J. Exp Med. 187(3):389-402; Takebe, Y. et al. (1988) sR alpha promoter: an efficient and versatile mammalian cDNA expression system composed of the simian virus 40 early promoter and the R-U5 segment of human T-cell leukemia virus type 1 long terminal repeat, Mol. Cell Biol. 8(1):466-472). Constitutive expression of mouse IL-7 driven by the same promoter in transgenic mice also develop a severe dermatitis characterized by gross deformities and a massive dermal infiltration of mononuclear cells that are mostly TCRγẟ cells (Uehira, M. et al. The development of dermatitis infiltrated by γẟ T cells in IL-7 transgenic mice, Intl. Immunol. 5(12):1619-1627). Transgenic mice expressing a murine IL-7 cDNA driven by a murine heavy chain promoter and enhancer also exhibited dermatitis and lymphoproliferation into the dermis, but reportedly of TCRαβ cells and cells that express Thy-1, CD3, and CD5 but lack CD4 and CD8 (CD4+/CD8+ thymocytes are virtually absent from these transgenic mice); these mice also developed B and T cell lymphomas, presumably associated with a prolonged lymphoproliferation observed in these mice (see, Rich, B. E. et al. (1993) Cutaneous lymphoproliferation and lymphomas in interleukin 7 transgenic mice, J. Exp. Med. 177:305-316).

Dysregulation of the IL-7 gene is associated with a variety of pathological states. Mice expressing transgenic mouse IL-7 under control of the MHC class II Eα promoter are highly prone to lympoid tumors (see, e.g., Fisher, A. G. et al. (1995) Lymphoproliferative disorders in IL-7 transgenic mice: expansion of immature B cells which retain macrophage potential, Int. Immunol. 7(3):414-423; see, also, Ceredig, R. et al. (1999) Effect of deregulated IL-7 transgene expression on B lymphocyte development in mice expressing mutated pre-B cell receptors, Eur. J. Immunol. 29(9):2797-2807). T cell sizes are also larger in the transgenic mice, and a polyclonal T cell expansion is observed (predominantly CD8+, indicating a perturbed regulation in these mice) (Mertsching, E. et al. IL-7 transgenic mice: analysis of the role of IL-7 in the differentiation of thymocytes in vivo and in vitro, Intl. Immunol. 7(3):401-414). Other transgenic mice that over-express mIL-7 (by about 25-50-fold) through the MHC class II Eα promoter appear grossly healthy (but for a low incidence of B cell tumors) and exhibit a 10-20-fold increase in T cell number over wild-type mice, characterized by large numbers of CD8+ cells that are also CD44$^{hi}$ and CD122$^{hi}$ (Kieper W. C. et al. (2002) Overexpression of Interleukin (IL)-7 Leads to IL-15-independent Generation of Memory Phenotype CD8+ T Cells, J. Exp. Med. 195(12): 1533-1539).

Mice that constitutively express mouse IL-7 from a cDNA under control of the MHC class II Eα promoter selectively expand IL-7-responsive early B cells, and are a good source of tumors comprising pro-B and pre-B cells. Mice that express IL-7 driven by a human K14 promoter develop a lymphoproliferative response that results in T cell infiltrates of skin that resemble alopecia.

Mice transgenic for IL-7R display large reductions in double negative (CD4-CD8-) precursor cells in thymus, presumably due to depletion of IL-7 by the large number of double positive thymocytes in the transgenic mice, suggesting that IL-7 levels must be exquisitely controlled to promote normal thymocyte development (see, e.g., Malek, T. R. (2004) IL-7: a limited resource during thymopoiesis, Blood, 104(13):2842).

As early as the cloning of human IL-7, it has been known that human IL-7 can induce proliferation of murine pre-B cells (Goodwin, R. G. et al. (1989) Human interleukin 7: Molecular cloning and growth factor activity on human and murine B-lineage lines, Proc. Natl. Acad. Sci. USA 86:302-306). Although expressed in certain chronic lymphocytic leukemia cells, expression of mouse IL-7 in tumor cells implanted in mice induce inflammation and reduced tumorigenicity, yet paradoxically mice transgenic for IL-7 are prone to lymphomas (reviewed in Foss, H.-D. et al. (1995) Frequent Expression of IL-7 Gene Transcripts in Tumor Cells of Classical Hodgkin's Disease, Am. J. Pathol. 146(1):33-39). Thus, it is desirable to obtain mice that express human IL-7 (but not mouse IL-7) from endogenous mouse IL-7 loci in a physiologically relevant fashion, in particular but not limited to mice that comprise human or mouse tumors, e.g., lymphocytic tumors.

Mice that express human IL-7 in a physiologically relevant manner are also useful for evaluating anti-tumor properties of putative therapeutics (including human IL-7 and analogs thereof) in xenograft models of human solid tumors in mice. For example, SCID mice implanted with HT29 human colon adenocarcinoma and tested under a variety of conditions (e.g., ablation of native T cells and addition of human T cells; addition of recombinant human IL-7, etc.) (see, Murphy, W. J. et al. (1993) Antitumor Effects of Interleukin-7 and Adoptive Immunotherapy on Human Colon Carcinoma Xenografts, J. Clin. Invest. 92:1918-1924). That study found that human IL-7 when administered with human T cells resulted in a significantly prolonged survival than in the absence of human IL-7 (Id.).

Thus, mice that express human IL-7, in particular mice that are capable of supporting a xenograft (e.g., a human tumor), such as, e.g., immunodeficient mice, have a specific and a well-established utility. IL-7 signaling has been shown to be necessary for development and survival of human T-cell acute lymphoblastic leukemias (T-ALL) in vitro and in vivo. (Touw, I. et al. (1990) Interleukin-7 is a growth factor of precursor B and T acute lymphoblastic leukemia. Blood 75, 2097-2101) T-ALL is an aggressive hematological cancer with poor prognosis; the understanding of mechanisms driving proliferation and survival of T-ALL cells remains relatively poor due to lack of xenograft models that can support the growth of patient derived tumors in vivo. Thus, an immunodeficient animal expressing human IL-7 can serve as an invaluable in vivo system for testing pharmaceutical compositions against such T-cell related malignancies, e.g., testing the efficacy of a pharmaceutical composition to target IL-7-mediated signaling in a mouse that expresses human IL-7 and has an implanted T-cell derived tumor, wherein the tumor requires IL-7 signaling for development and survival.

EXAMPLES

Example 1

Humanizing the Mouse IL-7 Locus

Mouse ES cells were modified to replace mouse IL-7 gene sequences with human IL-7 gene sequences at the endogenous mouse IL-7 locus, under control of mouse IL-7 regulatory elements, using VELOCIGENE® genetic engineering technology, to produce a humanized locus as shown in FIG. 1.

Targeting Construct.

Bacterial homologous recombination (BHR) is performed to construct a large targeting vector (LTVEC) containing the human IL-7 gene for targeting to the mouse IL-7 locus using standard BHR techniques (see, e.g., Valenzuela et al. (2003) High-throughput engineering of the mouse genome coupled with high-resolution expression analysis, Nature Biotech. 21(6):652-659). Linear fragments are generated by ligating PCR-generated homology boxes to cloned cassettes followed by gel isolation of ligation products and electroporation into BHR-competent bacteria harboring the target bacterial artificial chromosome (BAC). Mouse BAC bMQ-271g18 is used as the source of mouse sequence; human BAC RP11-625K1 is used as the source of human sequence. Following a selection step, correctly recombined clones are identified by PCR across novel junctions, and by restriction analysis. A large targeting vector (LTVEC) containing the homology arms and human IL-7 gene sequences was made. Mouse ES cells were electroporated with the LTVEC constructs, grown on selection medium, and used as donor ES cells to make humanized IL-7 mice.

The mouse IL-7 gene (mouse GeneID: 96561; RefSeq transcript: NM_008371.4) is modified by deleting exons 2 through 5 (deletion coordinates NCBIM37:ch3:7604650-7573021; minus strand) and replacing them with human IL-7 (EntrezGeneID:6023; RefSeq transcript NM_000880.3) exons 2 through 6 (replacement coordinates GRCh37Lch*: 79711168-79644608; minus strand). The human genomic IL-7 sequence is provided in SEQ ID NO:3 (NC#166E2F2).

The mouse genomic IL-7 locus is known and reported as a 41,351 nt sequence under accession number NC0000696 (hereby incorporated by reference); relevant 5' and 3' sequences of the mouse IL-7 genomic locus are provided in SEQ ID NO:1 (5' flanking) and SEQ ID NO:2 (3' flanking).

The LTVEC comprising the humanized IL-7 gene had a 48 kb upstream mouse targeting arm flanked upstream with a NotI site, and a 77 kb downstream mouse targeting arm flanked downstream with a NotI site. The LTVEC was linearized with NotI for electroporation.

Following construction of the LTVEC, nucleotide sequence of the LTVEC was obtained across the mouse/human 5' junction, which included, from 5' (mouse) to 3' (human), the following sequence with the mouse/human junction nucleotides in uppercase: 5'-tgcaagcacc aaaaaggtga ccacacttca cattggcgat cgcGGgtttc tatctgagga tgtgaattta ttta-caga-3' (SED ID NO:4).

Nucleotide sequence of the LTVEC across the junction of the human insertion and the 5' end of the cassette (see FIG. 1) was determined and included the following sequence having, from 5' to 3', human sequence/restriction site/loxp/cassette sequence with the human sequence/restriction site junction nucleotides in uppercase: 5'-gttatgtgct gatgggcttt atttgatcta cagaagatgc tctggtgaca ccctcagtgt gtgttggtaa caccttcctg CCtc-gagata acttcgtata atgtatgcta tacgaagtta tatgcatggc ctccgcgccg ggttttggcg cc-3' (SEQ ID NO:5).

Nucleotide sequence of the LTVEC across the junction of the end of the cassette and the beginning of mouse sequence was determined and included the following sequence having, from 5' to 3', cassette sequence/restriction site/mouse sequence with the junction nucleotides in uppercase:

5'-gtatgctata cgaagttatg ctagtaacta taacggtcct aaggtagcga gctagCCcaa ttgcgtactt tggatagtgt ctcttttaa cctaaatgac ctttat-taac actgtcaggt tcccttactc tcgagagtgt tcattgctgc act-3' (SEQ ID NO:6).

Following electroporation of the ES cell, a loss of native allele assay (see, e.g., Valenzuela et al. (2003)) is performed to detect loss of endogenous IL-7 sequence due to the targeting. Primer pairs, fragment sizes, and TAQMAN™ probes are as shown in Table 1. The C1 probe binds the mouse IL-7 genomic sequence (NC0000696) at nts 9,635-9,664; the C2 probe binds the mouse IL-7 genomic sequence (NC0000696) at nts 39,793-39,825. For a gain of allele assay, the C3 probe binds the human IL-7 genomic sequence (NC#166E2F2) at nts 29,214-29,242.

TABLE 1

LTVEC Primers and Probes

| Primer | Position | Sequence (5' to 3') | SEQ ID | Size (bp) |
|---|---|---|---|---|
| Primer Pair C1 | Forward | ttgcattctt ttccaaataa gtgg | 7 | 81 |
| | Reverse | ttccaggatg aataggataa acagg | 8 | |
| C1 TAQMAN™ probe | | atccatcatc actccctgtg tttgtttccc | 9 | |
| Primer Pair C2 | Forward | agctgactgc tgccgtcag | 10 | 125 |
| | Reverse | tagactttgt agtgttagaa acatttggaa c | 11 | |
| C2 TAQMAN™ probe | | atttttgtaa tgcaatcatg tcaactgcaa tgc | 12 | |

TABLE 1-continued

LTVEC Primers and Probes

| Primer | Position | Sequence (5' to 3') | SEQ ID | Size (bp) |
|---|---|---|---|---|
| Primer Pair C3 | Forward | ctcactctat cccatccaag gg | 13 | 74 |
| C3 | Reverse | atgggcaggt agcatccaca g | 14 | |
| C3 TAQMAN ™ probe | | tgaatcatcc ctttgtctag cagaaccgg | 15 | |

Example 2

Humanized IL-7 Mice

Generating Humanized IL-7 Mice.

Donor mouse ES cells comprising a humanized IL-7 locus are introduced into early stage mouse embryos by the VELOCIMOUSE® method (Poueymirou et al. (2007) F0 generation mice fully derived from gene-targeted embryonic stem cells allowing immediate phenotypic analyses, *Nat Biotechnol* 25:91-99). Four F0 mice fully derived from donor ES cells were obtained that were heterozygous for humanization of the endogenous mouse IL-7 locus. F0 mice are bred to homozygosity with respect to the humanization. Homozygous mice are genotyped to confirm homozygosity. All mouse studies were overseen and approved by Regeneron's Institutional Animal Care and Use Committee (IACUC).

Example 3

Expression of Human IL-7 in a Mouse

Figure 2:
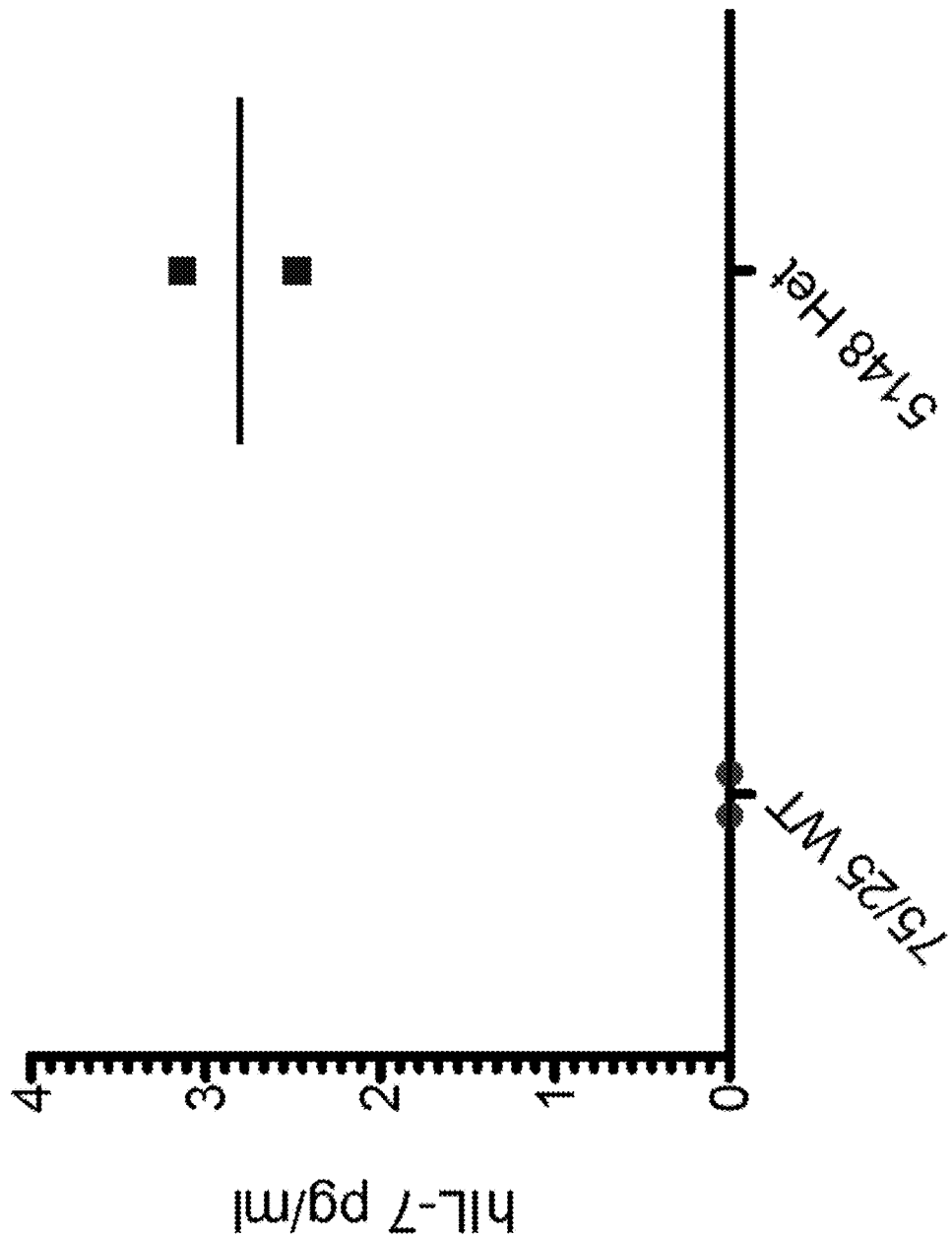
FIG. 2 depicts human IL-7 concentration in serum of wild-type mice that has a genetic background of 75% C57B6 and 25% 129/svJ (75/25 WT) and mice heterozygous for a humanized endogenous IL-7 locus as described herein (5148 Het).

Mice humanized for the IL-7 gene and their non-humanized littermate controls were bled and serum concentrations of human IL-7 were measured using QuantikineHS Human IL-7 Immunoassay kit from R&D Systems, Inc. Data was analyzed using Microsoft Excel and plotted using Prism statistical analysis software. Mice heterozygous for the humanized IL-7 locus (designated MAID 5148 het) expressed human IL-7 in serum at a physiologically relevant concentration. This is in contrast to transgenic human IL-7 mice bearing lentivirally transduced human IL-7 in double knockout mice, which mice exhibit unphysiologically and potentially seriously detrimental high levels of human IL-7 in serum (10 to 100 pg/mL) (O'Connell, R. M. et al. (2010) Lentiviral Vector Delivery of Human Interleukin-7 (hIL-7) to Human Immune System (HIS) Mice Expands T Lymphocyte Populations, PLoS ONE 5(8):e12009). In contrast, mice heterozygous for a humanized endogenous IL-7 locus exhibited about 2.4 to about 3.2 pg/mL in serum (FIG. 2), reflecting normal, or physiologically appropriate, levels of IL-7.

I claim:

1. A genetically modified non-human animal comprising in its germline a replacement of non-human animal IL-7 exons with a nucleic acid comprising at least human IL-7 exons 2, 3, 4, 5 and 6 to form a humanized IL-7 gene, wherein the replacement is at an endogenous non-human animal IL-7 locus and the resulting modified non-human animal IL-7 locus lacks non-human animal IL-7 exons 2, 3, 4 and 5, wherein the humanized IL-7 gene is under control of endogenous non-human animal IL-7 5' regulatory elements, and the IL-7 protein encoded by the humanized IL-7 gene is expressed in the serum of the non-human animal, and wherein the non-human animal is a rodent selected from a rat and a mouse.

2. The genetically modified non-human animal of claim 1, wherein the rodent is a rat.

3. The genetically modified non-human animal of claim 1, wherein the rodent is a mouse.

4. The genetically modified non-human animal of claim 1, wherein the rodent does not express an endogenous rodent IL-7.

5. The genetically modified non-human animal of claim 1, wherein the humanized IL-7 gene comprises a cDNA encoding a human or humanized IL-7 protein.

6. A genetically modified non-human animal comprising in its germline a humanized IL-7 gene, wherein the humanized IL-7 gene comprises at least human IL-7 exons 2, 3, 4, 5, and 6, and is operably linked to endogenous non-human animal IL-7 5' regulatory sequences, wherein the IL-7 protein encoded by the humanized IL-7 gene is expressed in the serum of the non-human animal, and wherein the non-human animal is a rodent selected from a rat and a mouse.

7. The genetically modified non-human animal of claim 6, wherein the rodent is a rat.

8. The genetically modified non-human animal of claim 6, wherein the rodent is a mouse.

9. The genetically modified non-human animal of claim 8, wherein the humanized IL-7 gene comprises mouse IL-7 exon 1, and human IL-7 exons 2, 3, 4, 5, and 6.

10. The genetically modified non-human animal of claim 6, wherein the rodent does not express an endogenous rodent IL-7.

11. A method for making a genetically modified non-human animal, comprising modifying the germline of a non-human animal to comprise a humanized IL-7 gene, wherein the humanized IL-7 gene comprises at least human IL-7 exons 2, 3, 4, 5, and 6, and is operably linked to endogenous non-human animal IL-7 5' regulatory sequences, wherein the IL-7 protein encoded by the humanized IL-7 gene is expressed in the serum of the non-human animal, and wherein the non-human animal is a rodent selected from a rat and a mouse.

12. The method of claim 11, wherein the modification is at an endogenous non-human animal IL-7 locus, and the modified non-human animal IL-7 locus lacks non-human animal IL-7 exons 2, 3, 4 and 5, and comprises human IL-7 exons 2, 3, 4, 5 and 6.

13. The method of claim 11, wherein the rodent is a rat.

14. The method of claim 11, wherein the rodent is a mouse.

15. The genetically modified non-human animal of claim 1, which expresses the IL-7 protein encoded b the humanized IL-7 gene in an expression pattern that is the same expression pattern as observed for non-human animal IL-7 in a wild-type non-human animal of the same genus and species.

16. The genetically modified non-human animal of claim 15, wherein the level of the IL-7 protein encoded b the humanized IL-7 gene expressed in the non-human animal is about the same as the level of non-human animal IL-7 in a corresponding wild-type non-human animal.

17. The genetically modified non-human animal of claim 3, wherein said mouse is heterozygous with respect to said replacement.

18. The genetically modified non-human animal of claim 3, wherein said mouse is homozygous with respect to said replacement.

19. The genetically modified non-human animal of claim 3, wherein the humanized IL-7 gene comprises mouse IL-7 exon 1 and human IL-7 exons 2, 3, 4, 5 and 6.

20. The genetically modified non-human animal of claim 8, wherein said mouse is heterozygous with respect to said humanized IL-7 gene.

21. The genetically modified non-human animal of claim 8, wherein said mouse is homozygous with respect to said humanized IL-7 gene.

22. The method of claim 14, wherein said mouse is heterozygous with respect to said humanized IL-7 gene.

23. The method of claim 14, wherein said mouse is homozygous with respect to said humanized IL-7 gene.

24. The method of claim 14, wherein the modified mouse IL-7 locus lacks mouse IL-7 exons 2, 3, 4 and 5, and wherein the humanized IL-7 gene comprises mouse IL-7 exon 1 and human IL-7 exons 2, 3, 4, 5 and 6.

25. The genetically modified non-human animal of claim 19, wherein the mouse nucleic acid downstream to said humanized IL-7 gene at the modified IL-7 locus comprises nucleotides 57-153 of SEQ ID NO: 6.

26. The method of claim 24, wherein the mouse nucleic acid downstream to said humanized IL-7 gene at the modified IL-7 locus comprises nucleotides 57-153 of SEQ ID NO: 6.

* * * * *

SEQUENCE LISTING

```
<160> NUMBER OF SEQ ID NOS: 15

<210> SEQ ID NO 1
<211> LENGTH: 8777
<212> TYPE: DNA
<213> ORGANISM: Mus musculus
<220> FEATURE:
<221> NAME/KEY: MISC
<222> LOCATION: (1)..(8777)
<223> OTHER INFORMATION: Mouse 5' genomic sequence present in humanized
      IL-7 mouse (from NC0000696)

<400> SEQUENCE: 1
ggcagatcct acggaagtta tggcaaagcc agagcgcctg ggtggccggt gatgcatgcg      60
gcccctcttg ggatggatgg accaggcgtg gcgtgggtga gaggagtcag ctgcctgaac     120
tgccctgccc agcaccggtt tgcggccacc cggtggatga ccggggtcct gggagtgatt     180
atgggtggtg agagccggct cctgctgcag tcccagtcat catgactaca cccacctccc     240
gcagaccatg ttccatggta agcgctgctc tctggtgcgc acaagtaggt gcgcctagcg     300
cgccggggac tctgggacag tccgggaggt gccacccgcc cccgcgcctc cgcacgtccg     360
ggaatagccc ggccttgcac tttggacagg ctgagagctt ggcctctccc atggtcagcc     420
actacccgcg ctgagctcgg ttgcccagaa ccattggcac ctgggcgtac aaccctggcg     480
```

```
ggcggggagg aacagttccc gaggcggttt tcagatcccc agacccagag cttcagtgcg   540
ggagccgcga cgcggtggcc ccctgcagtc aagactcagt agtcagtggt tttcagccac   600
tttgtcccta gccagtacct cttcaatgca gcccttcctg gcttcctggc tgtgcagtta   660
ctcacaggct gcctgggttc agggcgttgc tgggctctcg cagctcagaa cttcatggag   720
aatgaaagag tcgctcccag gatgcgcttt taaaccctaa aggacagatc attggaaaac   780
cccctcttct ccccgcagta agtctgggag tttccgatcc aggctgtaag ttgacttgtt   840
tgctgggaac ccaagtcctg cggctgagat tgcaaaaggc cagattttat tttccttcta   900
tatatttgct acttaaggga ggcagaactt aagtaccca tgagtacaaa ttcttagctc    960
cctgatcaaa tctaataggc ttgcattagt tttaaataag taaggattta aagtggacaa  1020
gaacagaatt gacagaggct ggaatccatt tgtagctaga actaatagag atgagaacag  1080
aatggagtgt gaggaggtct acctaaggga atgcaggtgt tttaaatact tcctcaagca  1140
agagaaccta tggaggtgca ggatctagcc taaggctctt tccttttgca accccattgc  1200
aaaccattgt attggtttcc ggcccactgt tttaggtaca attacttccc ctctcttagg  1260
tactagcgaa ccaaaaacat ttgagggagt acttatcaga aaccaaataa agatgtgga   1320 gacctgagag actgcccaag aaaatgatgg aaggctgcca aggtgcccct gcaggagctc  1380
actgtacagc tagagacacc gcatccctgt cttctttgca atgccctggg ttctgaaatt  1440
gcctttcact ttaacccttg gattacctac aacctggaga gataaaagga caaggaaaa   1500 gcaaggtgt  aatttaaacg aggaggcttt tcccattgag atacatccat atcggacatg  1560
ccttattttc ttagtaaaga aaatatgaaa atattaaact cacggagtt aaagtaagtg    1620 gcttttttt  tttctttcat tttcggtcca aaatttacta gaggcgtggg taaactccat   1680
caaggctgtg tgctgtgttt ccactttgtt atgtcgggac accaagtaaa caaggattca  1740
ctcgctgacg ctcaattgtg ctgcctcatt atgaatcagc atacatttta tttgtatact  1800
aataaaagga aacaatgaga aacatagagc cttgggaata tggaggaagc ctgaagatct  1860
atctgtaaag gagaattaga aatttcatct cagtgtgtat acttcttgaa caaaaatgga  1920
aagttctttt ataaaaccaa tctcatggcc catgggtatg aagtactgtt atcctgactc  1980
ttgacagata attttgtttt ttaattaatt tatttttatt ccttaatctt ttttttaca   2040 gtacagactt tatacctctc ctgttctgcc ccccccact  gctctcctcc ccatacctcc   2100
tccccagccc ccaccccacc cctgactcca agagaatgcc ctcatccccc atgccactag  2160
gcctccccac tccctgggc  ttcaagtttc tcaacagtta ggtgcctctt ctctcactga  2220
ggccagacca ggcagtcctc tgctctatat gtgttgggga cagacaactt tataatatgt  2280
agaaatattt acttttccc  ttgaaatagg agcatacgct gtagtttcag agcttggcca  2340
agaagcccct tcatgtagaa gacaatgaat atttgtactt cctctcacta tctgtgcatg  2400
cagttatgtt gtaggaagtg taattcagta gctaatagcg gattccctag acacctcaac  2460
ccgaacatca aatgcagctc ctgaatccct agaaaaattg ttttggagaa ttgttctttg  2520
ggctccagat tctctactgt aaactgctag tgacctgtat atatatatat atatatatat  2580 atatgtcatca tgaaatggct ataaaattga attatttgtt gaaatagact tgggaaagga  2640
cattgaaaga acacttctca aggaggatgg gaaagtcctc aaggtctcaa ccctagacaa  2700
actgttcagg ccacgaagaa atgctgactg acagtggaga aatagacatc cccagagagg  2760
agcatacaaa ttgtttatcc aaacagccag ccctgaagac atatgtgcaa gtaaggttat  2820
acagactggg caggttgact ttatgtattt agggagatag atggatgata gctagctagc  2880
```

```
tagctagagc acaacactta atgaaataaa aggtcatgaa tttgaaatag agcaagaaag   2940
gatatatatg agagtttagg ggaagaaatt gattgaggaa ataaaataat gatgttgtaa   3000
tctcaaaaac taaagaaac tgatagatga caggatatga tggactgagg aatccaattt    3060
tattatgtcc actttgacct cataacttaa gcagttgaag attgtatgta ttatttggct   3120
tacatttaaa accaacaaga attttagac agctatcatt ctggtttaac caaattcccc    3180
actgaaaaca aattctccag tttcaaaccc tgtaagcgat ttaaagacaa tactacaagc   3240
caacacttgt cttgtaatgc ttctacagtt tgttttatct gtgacctaat gaaaagttca   3300
gtggaggctg aggagtgagc tataaatcaa agtaacaaa atatggtaag tgctgaattc    3360
ggatgccatt gggacaaaag tgttaaataa actttcaaac cagaaaaata ttaacttgtt   3420
acggtgcttg tatgtggaag aaataactgt aaccacagaa caaaggtcac actcctgatg   3480
gtggagccag aaaccatgg gatcatacat tatcatacat atcatacatt agagagcctg     3540
gaaggttttc attttagaaa tcagggccag gaagctgaaa tgaaactcag ctatttagtc   3600
agttacacaa aatcctaaat tctctatgct ctaaatctcc ttgtttataa tatatatact   3660
atttatatgt attataaaat attaagtata tattataata tattaaaata tgtatggtac   3720
tgctctggtc tgtcagcagc tactttactt gattgaaata gtctacaaat gaagggctgt   3780
attgtaaaaa tagtatagaa ttgaaaattt cacgtaacac acacatgtat tatcaaagca   3840
agtgtgaagc aatgaaaaag tgctgcccgg tgaggtgtaa ggtcacatca ttctgggaag   3900
cacatatctc agaagaaaac tggcaatctt ggaaagtatg gcaaatgaac ttattgaaac   3960
aggaaatgga ctttgaaatg acttttagat ataggtgcga attaatctct tttcactaac   4020
catcataact ttctccttg agttcaagtc acattccctg tctctttcat ttgcctggtc     4080
cccccaaaaa cataattttt agggacctat aaggcaaaag atgaaataaa aagccagttt   4140
ctacaaaaaa tgtagatggc tataatccaa ttgagtagta attgatacct gtgtatccca   4200
gtgaagggca gtcataggag aaggctgatg aatggtatta tgagaaggtg cctttcaaac   4260
agaatagcag cagataagat gttatcaatt gattatgggt atttaaaagt gattgtcatt   4320
ttctccccct cttgaagcag atatagatca gattaggcca gattaaaagt agataaaggc   4380
agttttgtta ggaatcccct ctctggtggg ttcatccatc tcacaggtgg aagtcagtga   4440
agtcacacag ccaggctaaa gcatgggggt tttatagagc ttaagcaggg agtagtgatg   4500
tgccagaagg agctaggatg tgtccatac gtggtcaaaa actgagcccc tggtgggcac    4560 tctgggtgt gttgcaggaa cccagggatg agacatggcg acttattggc ctagagtttt    4620 ttgttttgt ttttgttttt cccaagcagg ggttccgggt gcaggcaggg ttggggaaag    4680
gagggtagct tccaagtggg gtttccctgc ttgttcagaa tatgagcagg agttccagcc   4740
taacaccccg acctcttggg gtatagatac agccacactc tgctgaagag ggacgggaga   4800
gttgggagcg ggtgggatca tactcatctg caggcatgct gtaggaccat tcggtggtgt   4860
gttacttaga aacttttatg aatccgttcc tggatgaaga gaaggtagca aggtgctagg   4920
aagatgtgca tgtgcaaggt gctaggaaga ctgaggctag ccatgtgaag agtaacactg   4980
ctagagagaa ttgaatgtgt cttggttgtg ttgtgggaac tctttagaca atttgcggag   5040
tgactctgtc caggtctcca caaggccaga ctcactgatg taagagtggc agggacatgc   5100
agatgccgcc cttaccagtc atgaggatac ttttagggcc attgaagcct ataagaatct   5160
tattaagttt acagagagag agagagagag agagagagag acagacagac agacagacag   5220
```

```
acagacacag agacagacag agacagagat tttagacatg ttagacagta gacttatacc    5280
tttttgtcat agtacaggct tcggaaacat taaaatttga ttattattaa agctttgaat    5340
tttgaattct taatataaca gaaacatagc taggggaaga atctgaagca ttttttttaaa   5400
aaaatatatt ttatgtcatt ttttctcttt tgtcttttaa cctttataac ttgcatttat    5460
taactttaaa catcttttat actatgaaag aactttctta catcctttga atttaaactt    5520
ttatatactc agaccaccta tgggtttttc tctcttttta tccagatatt gaccatgact    5580
cgtaggtagc tgatcattga gagcagttat tgcaaagtga gttcctttag ataaaggaat    5640
attgaaaatt ttatattgaa ttttttcagtc taataatgag ataaattgta tctagccaaa   5700
gtagtggcat gtcttggaga gtgtcgtttg aggactgatt tttacacatg aagaggactg    5760
ggaaggtagc tgaagtcttg gatcctgatg ttaaatgaat cctcaaaccc accagagtcc    5820
tgagaaggat caatttttatc tgagtaagga gggaactgca agagcaagca gtttctgagt   5880
ctattaaaaa tgacacagac ttacaggact ccctggacag tcagtcatcc aggaattctc    5940
tgtggtcagt ggggcatcca ttttggctat caggccaaga aaatctggca gactttgtgt    6000
gtgtgtgtga atcaagacta tgagaaaaag actgccctac cttgtctagg caagtgaatc    6060
agtcaacttc ccagtgtcct acctgtccac agtgtggccc atgtgctgtc aacagtcgca    6120
gcaaagggct ctttatagcg agcaagcttc aggcagaagt tcttctgggc tgtgttctttt   6180
ggaggagatc aggggtgctg tcaagagctg gtgtgtctct gttatgaaaa gcttttttcat  6240
tagccatttt aaatgccata tttttatagac ctctgaagcg tctgaggacc atttgtgtct   6300
ctacagtata tctaaataga caaacgtttg ttttttggct attcaattttt tatttaactt   6360
tgaaaatata gataggaggc taagtaaaac ttattttggt aattaatcat aattataagt    6420
gtagttatga acatattaaa gaatgtgatt attttttgagg taactgataa ctaacttgta   6480
tgttttaata atgtttaaca gcttataata aatgctgtat gttatatttta acctgaaggc   6540
agtgttagga cagaaaaggc ttaataagtt ggaaaaatgt ctcagtagcc cttcatgggc    6600
ctaaggaaaa agagtcgctg tggcccaggc ataggtttaa ggaagctgta gttactggag   6660
gaaatggagt gaccattaag ttaagggggtg tgggagaggc tgatgtgctc agtgtatgag   6720
caatgaggtc tcctcacagg acaggctgga ctgtgcagag tggatagggt ggacatggga   6780
gtgagtgtag ccttgcccca ttggcgagga gaaaagccag gttaccagga ggaagaggag    6840
gaggaggggg gggggaagtg gggggaggag gagggctgct gaagctttaa cagagtgcag    6900
gcgaactgaa aggaaggaat cctgcggggt tacaagaacc agagccatgt ggaacacata    6960
gcaggctaaa gaatcggact tcagaattta gaatcaaatt tccagacaag taagtgatcc    7020
atacacactt tgggaggatt agcatggttt ggagcaacca ttgcagttac aaaaggttga   7080
gtgtgtcaaa gagaagaagt gggaagagtc tgggctctgt caatacaggg gtttggggtt   7140
tgggatccag gtccttggag gcaagggggtc ttttggagtg aacatccttg ctagtaggac  7200
gtgagcctta gaacattggc tacagaggaa gggacagggt gtggttccca acaaacctgg   7260
ccagaaggga ttcaggccat ttgcccgcat accaaaagaa atgttaagct taagatccgt    7320
ggagaattttt aacatcaaga atgctctctt gtggccgttt actgaagcga ggccatagaa  7380
caaagtctga gacagtccta atttggacaa cttttgtagc agtcacccca ggaatgtctg    7440
aggatcaggt ttagactccg tgttgcccat ctcctagact tgtggcgacc tatgatacag    7500
tgtcccactt ggtagcctgg ggtaaaacag tgaggagtaa agaaaccttg taaaggatat   7560
ctcagaatcc aaatactagg ccatggcttg gcagaggatc ttggtaagtt caaagttgat   7620
```

```
ccttcagatg aagagagaaa gggagagaaa ggagcagacc ccatgcagcc atggtccctg      7680
cccgctgggc tgcaggctca acttctcccg cattttgaac caagatgata ggaattttct      7740
ctccatccat gaagcagatc tagggcagat tgatgagat aaaaagtaga tacaggcagg       7800
tttattagaa gacaactctc aagtgggttc accgatctta cacatggaag tcagtcaagt      7860
cctatatctg ggctaaaaag caagggaggt tttatagagt ttaggtgagg aatgatgcca     7920
tgccagctag gaactgggat ggtgtgcata catggtcaaa aatgagaaa aaaggagtga      7980 tagctctttc ctgtgcttag cacgatttag ttgcctgtag ttcttttgtc tatagttgta     8040
gctctgtgag attctgtaat ttcgaccaag catactttct ttacatatat atatatatac    8100
actcagctgc taatttatgg tggatttata aataaattta tttataaatt tataatttat     8160
tgccttttta ataccatgta taatagtatg atatattgca tcctatgata tccttacatt    8220
ctttaagttg tttccaatgt caattccttg ggtttagaga atattgttt agacttttaa      8280 atagagaaga tgcacataaa atgctgaaca ctgggatttt ataacgttaa tttgggaaaa     8340
tcatggtaag tatattttca acataactga gttcagggaa aaatgaaagc aagattcatg    8400 aagatataggg tggcttaacg ttttatgta ccagaagttt ccatcttaat tatttactcc    8460
aagtgatgat tccatttaaa atctccttcc ttttaattaa acagttcact ctgattggca     8520
tgacttactt gatgtagtca taaacaccag ctgagaggtc tcgagtctat tgtgtgaact      8580
ttgcctaaca gggaaggaat ttaaagagag ctatgcttga acagaatcta ggtctttggg    8640
aaaatagata cacaaaataa tgacataagg gaaagagttt gcgaacatga tttaggggc      8700 aaagtaaaac tctgtaaagt ccatcacaaa gaatcgccat agtgcaagca ccaaaaaggt    8760
gaccacactt cacattg                                                    8777

<210> SEQ ID NO 2
<211> LENGTH: 944
<212> TYPE: DNA
<213> ORGANISM: Mus musculus
<220> FEATURE:
<221> NAME/KEY: misc_feature
<222> LOCATION: (1)..(944)
<223> OTHER INFORMATION: Mouse IL-7 downstream (3') genomic sequence
      from the humanized IL_7 mouse (from NC00000696)

<400> SEQUENCE: 2
ccaattgcgt actttggata gtgtctcttt ttaacctaaa tgacctttat taacactgtc      60
aggttccctt actctcgaga gtgttcattg ctgcactgtc atttgatccc agttttattg    120
aacacatatc ctttaacaca ctcacgtcca gatttagcag gagactagga ccctataact    180
ttgttaagag agaaaacact aatttcttgt tttatagtag ggtcttattc gtatctaagg    240
caggctagga ttgcagacat gagccaatat gcttaattag aaacattctt tttatgttaa    300
actcatgtct tttacaagat gcctacatat atcctatgta tatgcctgtt taaatccttt    360
tttgtaaggt ctgctgtctt ccttcagttg taatggaaag aaacactatg ttgtagaggc    420
caaatttctg aaagtgataa gggtttgctt gtactgaatt ctcattctcc ttgctttttc    480
cagccacgtg agcatctagc tatctatacg ctggatgtat ttgaccgatg cctgctccac    540
tggcacattg catgtgtggt agccatgcct tcttgcttct ccttttcccc aaccctata    600 atgctctact cagtggtaca gatagctggg attatcacaa ttttgagaga aacaccaatt    660
gtttaaagtt tgtttcataa tcaccatttg cccagaaaac agttctctca acttgtttgc    720
aacatgtaat aatttaagaa actcaatttt gttaatggac tttcgataac ttccttagat    780
```

| | | | |
|---|---|---|---|
| atcccacatc | tcctacgtgt | cagtcctttg tcctgaggaa ctggtaaaat gggtaagccc | 840 |
| ttagctagcg | aactgaaggc | attcgcatgt gtaagataat ctctataccT gcaaggctgt | 900 |
| ctggatggct | ccctaccaat | attgaacaat attctgattt tggc | 944 |

<210> SEQ ID NO 3
<211> LENGTH: 72752
<212> TYPE: DNA
<213> ORGANISM: Homo sapiens
<220> FEATURE:
<221> NAME/KEY: misc_feature
<222> LOCATION: (1)..(72752)
<223> OTHER INFORMATION: The human genomic IL-7 sequence (NC#166E2F2)

<400> SEQUENCE: 3

| | | | |
|---|---|---|---|
| acatccgcgg | caacgcctcc | ttggtgtcgt ccgcttccaa taacccagct tgcgtcctgc | 60 |
| acacttgtgg | cttccgtgca | cacattaaca actcatggtt ctagctccca gtcgccaagc | 120 |
| gttgccaagg | cgttgagaga | tcatctggga agtcttttac ccagaattgc tttgattcag | 180 |
| gccagctggt | ttttcctgcg | gtgattcgga aattcgcgaa ttcctctggt cctcatccag | 240 |
| gtgcgcggga | agcaggtgcc | caggagagag gggataatga agattccatg ctgatgatcc | 300 |
| caaagattga | acctgcagac | caagcgcaaa gtagaaactg aaagtacact gctggcggat | 360 |
| cctacggaag | ttatggaaaa | ggcaaagcgc agagccacgc cgtagtgtgt gccgcccccc | 420 |
| ttgggatgga | tgaaactgca | gtcgcggcgt gggtaagagg aaccagctgc agagatcacc | 480 |
| ctgcccaaca | cagactcggc | aactccgcgg aagaccaggg tcctgggagt gactatgggc | 540 |
| ggtgagagct | tgctcctgct | ccagttgcgg tcatcatgac tacgcccgcc tcccgcagac | 600 |
| catgttccat | ggtaagcgct | cttctccctt cgcacaagt tcgcgcgccc gacgcgccgg | 660 |
| ggcaatccca | gacgcgctgg | gggcccctgc tcctaggcaa gtccgggaat agcccggcct | 720 |
| tgcactttgg | acctgcggag | agcactggct ctcccatggg cagccaacag ccgcgcctga | 780 |
| gtatcctggc | acatagccac | ttgaacctgg ggcggctgct gcccctggca ggctgcgagt | 840 |
| aacagtcccc | aacgcctgct | ttctgtcctg agagggaacg ctgcagcctc cgcgccgctc | 900 |
| agcggtggca | gcccacagcc | ggtctcagaa gcagccaaag gctctctgtc tggcgccctt | 960 |
| cccgtgctcc | tggccgcccc | aagttactca cgcaggcggc ccgggttcgg cgagtagctg | 1020 |
| ggctcttgca | gctcagaact | ccctagagaa gtgaaagcga agctcccacg ggacgcgctt | 1080 |
| ttaaaccctc | ggggaacagg | tctccggaaa accccatttt tcccccctga gtaagactgg | 1140 |
| gagtttccgg | caagggctgt | accttgcgcc tattgctggg aaaccagtcc tggggctggc | 1200 |
| gctgaggaag | gccagcttct | gggttttttt gttttgtttt ttgttttttgt tgttattttt | 1260 |
| tcctacgggc | gcttcttgat | ggaggcagaa tgaaataggc gtgactctaa cttccagacc | 1320 |
| agtattgaga | cctaatatat | cttatttgtg cagaatacgg atttagaatg gacagggaca | 1380 |
| gaattcagga | gggttggatt | cggatggcag tcatatatga ccaatgaaag agccaaaaaa | 1440 |
| cttactggaa | ttaaaaaaga | ggaaaaagga ttgtgagggg aaaagatctg cttaggaaaa | 1500 |
| ttggaatgct | ttacagtaag | tacttcctca agcaagaaga cagctggggg gagggtgcgg | 1560 |
| gaataggaaa | ctgactgctc | tttcttttga tggctactcc gttagatcaa gacttctttc | 1620 |
| cactctcgtg | ggtaaagaat | caagaattga cacaaccaag gagtgccagc tcagtaacaa | 1680 |
| aacaaagata | gagagagcgg | aaagaatagc caacgtaatt atggaggact tctaaggaat | 1740 |
| gtcctcccgg | agcttaatac | aaaactaaaa attgagcaca accctatttt ccttgcaatg | 1800 |

```
cccatagttc tgcagtttct tcttctggat caccccttggt tctaatcctt gcaacacctc    1860
tgctctaaag tagaaaggta aactgagaaa aggaagctag cgtgtgcatt tttcagaaaa    1920
agcctttact tcctgaagca cagttatatg aatcatgggc tataagtttt cattagcaga    1980
caaaatatta aaattctaat aataatgatt ataatgcatg gcttcctgaa gtttgtttca    2040
agaaatttca ctagaagctt gttccattaa gagtgcacat aatgttactc tttacccttt    2100
gtctttgcca tttcttttga gagttgaagt agttgaggat ctactatgtg gtctccaact    2160
gtcttatctg gtttgggtaa tttcatcata tttgaggacc aaaaagttga atagcaataa    2220
aaatagactc tactcgggag gctgaggcag gaggattgct tgagcctgga agtcaaggct    2280
gccgtgagcc atgatcttac cactgtcctc cagcctaggc aacagagtga tgccctgtct    2340
caaaaaataa taatagagaa ctaatattag aaaccctgaa caagcataaa ggagaattac    2400
aaactgcatc acgttagtgt tgaatatttt ttttaaaaaa tggaaaaggc catttcatag    2460
aacgaactta cgtgtcatat tcacactcat ctatgtgact ttttttttctg cttttaaccc    2520
tgacacataa cctactgtaa caagaacaaa tatttagtct cttttttctga aataaaagca    2580
tatgatgcag tttcacagtt tggccaggaa gtaccttagt gaggttcatg cacaggaaga    2640
tgggtttta tgcaatcccc ttgactacac atatatggtt attttttaag gaagcaatgt    2700
agttcagtgc ctaaaagctg aggttctaga ctcttcaatg tgacagtctt ggatttgaat    2760
tccatatcta tattatgtac aggaattttc tgactaggca tggtggctca agcctgtaat    2820
cccaacactt ggggaggctg aggtgggcag atcaccttag gtcaggagtt cgagaccagg    2880
ctggccaaca tggtgaaacc tcgtctcaac taaaaataca aaaaatttg ccaggcgttg    2940
tggtgggcac ctataatccc agctactcag gaggctgagg gaggagaatc acttgaacct    3000
gggaggctga ggttgcagtg agccgtgatc gcaccattgc actccagcct agatgataga    3060
atgagactcc atatcaaaaa aaaaaaaaag agagagaaaa atacgaaagg aattttccta    3120
catgactgtc tttgtgcccc agattctcca tctataaatg tgaataactt gtagtactta    3180
cctacttctt catgaagtgg ttatggaatt aaattatcag tgaaaatagg tctatgcaat    3240
ggacattcag taaacactgg ttttaaagac tgataaagac tggagttgat ggattgtaga    3300
aaactattta tgttaacttt gaccccccata acttaagcag ctgaggattg aatgtattat    3360
ttggcttaca ttaaaaacca acaagaattt ttagacagac ctccttctgg tttaaccaaa    3420
ttccctactg aaaacaaatt ctccaatttc agcctcttca ggggaagtaa gggcaatccc    3480
acaagccacg cttgccttgc gttattccta tggtttatct tttcggtaac ctaatgaaaa    3540
gttcaggatg gtgggagtg tgggtgtgac aacaatgcca aaagcactct caaaccagcc    3600
attcttaata tgttactctc tatgtgatgt aggagaaagg tcttcaatta tggaccaaac    3660
taccaagcta catcattaat gggagagctg ggaacctatg agatgtgggt ccaaggccct    3720
aggtatgttt gcagcattgt ccgtgaggca atttcgagatc taaagagttt ctgcatttgg    3780
aggaccaggt agattcttag aataaggtgt ctgcaagatg aaaaagatca tttagtctga    3840
agttttcatt ttagaaatca ggtaagtgac cttaagagat gctgtgtcat ttacacagtc    3900
acacaaacca ttgtcttggc aagtcaaaag tctcaagttt tgacttgact actcagccta    3960
ggctcagtag atcgtggctc acggccatgg cttacggcca tggctcacgg taagatcatg    4020
gctcatggca gccttgactt ccaggctcaa acaatcctcc tgcctcagcc tcccaagtag    4080
agtctgtttt tattgctatt caacttttg gtccctcaaat atgatgaaat tacccaaacc    4140
agataagaca gttggagacc acatagtaga tcctcaacta cttcaactct caaaagaaat    4200
```

```
ggcatagaca aagggtaaag agtaacatta tgtgcactct taatggaaca agcttctagt   4260
gaaatctctt gaaacaaact gcaggaagcc atgcattata attattatta tgagaatttt   4320
aattccaaaa cctctgtgct ttatattgcc atagtctgtc tggggctaat tattcaatga   4380
caacaatggc aacagaaaac actcttaaca ggcaaggcaa attatgtttt aaaattgaga   4440
aagtacgtgt aatatacaaa aagactgaat tttccagcaa ccctcattgg aaagaatgca   4500
caaaatgcca tccggtgaat aaataggttg atttaaattt gaggagcact taactactga   4560
aaattgaggt gaagaagaca gctaatgctc atagcaagta aaacaacctc atgtattaaa   4620
acaaaaggtg gacctttgga atatttatga taatggtaaa agtatccctt tcactctagc   4680
atttaattat tttattatat tctcctttaa gctcatttca agttatatgt tatataattt   4740
ttcctctatc atctactcct cccgaagtat accttttgga ccctgtaag atgacagaga    4800 aaataaaaag tatgatttca tacaatctat acaaatctga ttacaaggtc agaatctggt   4860
gaataattag caattgatca tccaaatgtc catcagcaga ggtttggata agaaaaatgt   4920
ggtatggccg ggcttgtaat tacagcttgt aattctgaca cttaaggagg ctgaggcagg   4980
aagattgctt gagcccagga gttcaagacc agtctgtaca aaagagtaag agccgtctgc   5040
taaaaacaaa ttttaaaaaa ttagctgggc atggtggggc accctgtagt cctagctact   5100
cagaacgctg aggtaggagg atcgcttgaa cctaggaatt tgaggcttca gtgagctatg   5160
atcatgccac tgcactccag cctgggcagc agagtgaaac cctgtctcaa aaagagaggg   5220
agaaaaaaag aaaatgtggt atatgtatac catggaatac tactcagcca taagagttaa   5280
gtcgtctttt gcagcaaaat ggatgaaact tgaggccatt atctaagtga aatgactcag   5340
aaagtcaaat gctgcatgtt tttacttata actgggagct aaacagtggt acagatggac   5400
atacagggtg gaataatagg cattggagac tttgaaaggt gggagagtag gaggggata    5460 aggattgaaa aattacctat tgggtaccat gttcactatt caggtgatag atacactaaa   5520
gcccagactt caccactgta cagtatatta aatatgtatt agtaagaaat ctgctctggt   5580 ccccettaaa tctatgagtg tacatttttt taattgccaa atatttttt ttaaattagc    5640 aattgatcac tgaggatctt taggttgaag gaacaggagt agaagagaga ggcaaaactt   5700
cattcagaag acaaatgtga ttacatgtta tcaatagatt atggccattt ctaatcgaat   5760
cctggtaaag caacaaattc aggttagcat ccaaacctgg cacctactat gtatgtgtta   5820
cagaaagact aacttgcaga acttttgga tatttataaa tcatatatat atatatgaga    5880
ttttatatat aaagttcctg acacatggta ggtactcaac taaaggtaac tagcatcatc   5940
atcattatct gtctcctaag ttaattcatg ctcatcatgc atataggcac ttagtggcag   6000
agttattaat atatttgtat aaataaaatt atcaattttt gtttctctta ctatgttgtc   6060
acatatgcag atgagaagtt agatttatgt ttgttttcat aattgctacc cagaaaattt   6120
tctctatttg taacaacatg ggtcacttga tttattggga ggtgttattg attgttttat   6180
atgacagatc atgatataat agatgacaat gttactggaa actttatgat atccctaaca   6240
gtcttcaggc tgtcacaata ttagttcctt gggtttgaag gagtgttgct tgtactctta   6300
atcagagaag gcacacaagt gaaatatctt gcattcaagt acaattgaag ttcatttggg   6360
aaattcacag gaaatacatt gtcaacatgc ctcagagttt acaaaaagat acaaataaga   6420
cactatggca ggtttatgaa gaaataggtc cctgtatgat cagatttaa tgtttgtggg     6480 aaccactggc tttccatctt tctgcctgaa ataataccat tatttcagtc cttttgatta   6540
```

```
gacaattgct cctaattggg aagagttatc aaaaacagat agaaatcatt ggtttctatc    6600
tgaggatgtg aatttattta cagagttttt ctaacatgac aagaagctgg atagcgctgt    6660
gtttgaaaag aatctgggtc tctggggact cagagacaga agatagtgaa aggataggag    6720
agtagtccca aaatacaaac ataaactttg taagactttt gggaatgtaa acccttcagg    6780
gttcattatt aaaagaaag agtgcactta cagtagttac agtgcaatcc cagggagatt    6840
aacctcccac agtgttgcct ccaagaagca aatagacatg gactaccatc aaggtttaca    6900
aaaatataca attacgtgca gtacatcata aaattccaac aatatgtaac tcttcgaact    6960
gtagtgcacc tctttacctg tatatgcctt ttcttatggg gatgttcaac ataaattcaa    7020
attgattaac accctggagt gttttcaga agcagtctat gatttcatca cccttgtttt    7080
gcactttcct aaagagtaat tgcaaaataa aaagtgaaa ggacgctata ctccaaaatg    7140
ctgttccact ttggttgtta cataagttca acttttgagg ttcttcctgt agtatctcca    7200
aaccaagatg tatttttaaa attattagaa attagtggtc cagtccattg aaaccccaca    7260
atcaaatgca atacgatata acatttagct cattcttatt tactgtcaaa tttagtttct    7320
tttaggtata tctttggact tcctcccctg atccttgttc tgttgccagt agcatcatct    7380
gattgtgata ttgaaggtaa agatggcaaa caatatgaga gtgttctaat ggtcagcatc    7440
gatcaattat tggtatgtga ttattttgtt ttactcacat tttcatgcat tgggaaaatt    7500
tgaacctttt tggtatgcag ttttataatc aagtattcat ctttcttgac aagaaagtga    7560
agtaactata gaataaaatt taatgagcta ctaactgtat atttttatag ctgacataat    7620
tatgtagctt aaaaataatt ctttcctcga ctctaagatt ctcacaacta ttcatttcag    7680
tcctatttcc cttttagtaa atttcttgta agcataattc agtatcactg cctaaatttc    7740
ctcacctccc atttaccatg ttagtccctg tagaagcatt acattaagag tgggaaaata    7800
acagagtaaa tagttaagac ttatggtgaa tagatgtgta ttttatttgg ctgtgtgtag    7860
atgcatagtt atttatatgt gtgtatttta tatctatgtg taatcaataa tttgttatga    7920
gttaaatttt ctatttttga tggttaaagc ttttctaatt aatagatttt ataccttaga    7980
gccaacttag gtttctagaa aattcgagca gaaagtagaa aattcccata tgctctctct    8040
ctctctgcac tgtttccctt attatcttac atcagtatgg cacatttatt acaattgatg    8100
agccagcatt gatacattac ataagtgcat agttaacatt aggattcatt ctttatgttt    8160
tatagtttta tgggttttga taaatgtata ccatcacata tccgtgatta catatcatac    8220
aaatcatatg gtaaaaatct cctatccacc gactcatcct tctctttctt ccctgaact    8280 cctagtaacc actgatttgt ttatgtctct gtagttttgc cttctttaga atgtcatata    8340
gttagaatca tgcggtctgt atgtggcctc tttagactgg attctttcac ttagcaatgt    8400
gaatcaaagc atcccccatg atttttttgtg gtttgatatt tcatttttc ttattgctgg    8460 ataacagtct attgaatgga tataccacaa cttgtttatt ttttcactga ttgaaaaatg    8520
tgtcacagtt gcttccaata tttggaaatt atgaataaaa cttctataaa catatacgtg    8580
cagggttttg tgtggacata agttttcaac tcaggtaaat acctacaagc atgactgctg    8640
gatcatatgg taagactgtg tttagctctg tacaaaactg ccaaactttc ttccaaagtg    8700
gctgtaatat tttgcattct taccagcaat gaatgagatc ctaatgcctt ccatcttcgc    8760
cagcctttgg tattatcagt tttgcagatt ttaaccattt taataggctt gtcatagtat    8820
ctcagtgttt tttcaatttt ccattccata atgcataca atgttgacca tcttttcaga    8880 tacttttgc catttgtata tctgcttgc tgaggtgtct gaactcacat ttttactgaa    8940
```

```
atcttaacaa tattgagtct tcttagccat tatcatgcac tatctctttt ttaattttt     9000
tcatcattta attgtattat ctggacagag aacaaatgag tattactgtg acaacatttg    9060
taaataatta tatgtgtgta aaactctgca aagaagatg caattgaaaa tgcaaacttt     9120
catcagagct ttgttctttt cagcatataa atcctgtaaa tattttatta gacttatacc   9180
taaatatttc atattttagt gctattttaa atggtgtgtt tctaatttca aattttagtt   9240
gtttattgct ggtacatagg aaagcaattg attttttgtat attaacctat gtcctgcaac  9300
cttactataa tcacttgttt gttctagaag tctgttgttg attattagga attttctaca   9360
tagacaatca tgtcatctgc aagagttaat tttttccaag gtttcagagc tgtatcaata   9420
caatgtgatt gatttattgt tttaacagat aattagtctc ttttcaatca gattgaaact   9480
gaatagcaaa ggaaaactct ctcaaatgtt cataagatgg gagaaattgt ctaatctgtc   9540
ccccgacttt tactccactg tctcttccac atactcatac tgaagtggca tgatgccttg   9600
aggaatttag tgttataccc ttgtaggaa tatggaaact aaaaagagat actgtgctac    9660
actgtacatt gtaatccaga ggttcctgat tttgcccatt gacaagaaaa aaaatagtgc   9720
acagtaaatg gcaattgctc catttagatt tcttgctaat ttggacattg catttgatga   9780
tgctactaaa ttaatctttt gagtcaagat aatatttctc atttaattt gttatctggg    9840
cagagaacaa actagtgcta gttcaacatt tataaataac tatatgtgta taaaagtgca   9900
aaataatatg ctattaaaaa ttcagtaaaa ggagagtttc atccaacaga ctcatgacac   9960
attttttggg tgggagaata tagaggagct tatctcatta acacacaaaa caagaacaag  10020
tacatcagca gcaataatta tattattttc aaaaaacaaa acatggctac tcttcttaag  10080
gaggttaatt cacaagacat ggaagagaac acagctaatc agtccaactg agtagttcca  10140
tagtaacctt aagaatgttt tctatacata gaaggtgata aatttgaggg aaggagaaag  10200
aaagtctcaa tgaattatta atgtcaacat gactggtaga gcagatttag ttactcattc  10260
attcagtgtg gactagatgc tttgcagaca ttactgtgtt taagtcttgg ggagaccata  10320
atactaatag ttatgaagtg cttgttatgt tctcagtgct ttccatgtgt taactaatt   10380
aatccttaca acagcccttg agaaagacac tcttactacc tccgtttcac aacagaagaa  10440
tctgaggccc agggttatcc agtttataag tgaccgagcc agaatctttg tccatgctct   10500
ctaccccact ctcctacctc ccaaggacaa tctctgtgat agtttattca atcagcaaac  10560
atttatttag ggcctgatat gtacaagtta ctatgaaaaa cccatttgtg taggtgatgt  10620
tgggtttggg tgtggataga atgatggacc aagtacagat ctttttttcaa gaagcttaca  10680
ttttggtgag tgttaaagat tggtggtgaa taatgcaagt tacagtttta aaagtaggaa  10740
gagtgacttc ctgtttgtta gatgtctgct tatcatctaa caaatagact ggttgtaaaa  10800
caagctcaga aacaaaaaga tgtaaatggt gttctggaag tagtaaagaa gcaattttgg  10860
cctgtgtaga agtttcagca agttatccag aaggtctagc taagatgatt ggtaaaagtg  10920
gctacactaa acaacagatt tcaatgtaga tgaaacatcc ttctactgga aacaggcgac  10980
atctagaact ttcatagcta aagaagagaa gtcaatgcct ggcttcaaag cttaaggaga  11040
caaactaact ctcttgttag ggacaaatgc agctggtgac tttaagtttt agcaaaatat   11100
tactgctcat tgacaatgca aaactagtca cccaagagtg ctgatggata ttaatgttt    11160
cataactgct aatataacat ctgttttttca gcccgtgaat caaagagtag tttcaacctt  11220
caagccttat tttttaagcc atgtattttt gaggctatgg ctgccagaga taatgattca  11280
```

```
tctaatagat ctgggcaaag aattgaaacc ttgtgaacag cattcattgt tctgtagtag   11340
atgtccttaa aaacatttgt gattcatggg aggaggtcaa aatatccaca ttaacaggag   11400
ttcggaagaa gttgattcca actgtcatag atgactttga ggggttcaag acttcaatag   11460
agaaagtaaa tgcagatatg gtagaaatag caagagaatt agaattagaa gtggagcctg   11520
aagatgtgac tgaaatgctg aaatctcagg ataaaactgg aatggatgat gagttgcttc   11580
tcaggcatga gcaaagaaag tggtttcttg aaatgatttt actttgagta agatgctgt    11640 gaacattgct gaaatgacaa gaaaaaattt aggatattac acaaaattag ttgttaaagc   11700
aatggaagga tttgagagga ttgcctctaa ttttaaaaga agttctactg tggataaaat   11760
gctttcaaac agtatcacat gctacagagg aatcttttat gaaagaaaga gttaatctat   11820
gtggcaaact tcattgttgc ctcattttaa aaattactac agccacccaa ccttcagcaa   11880
ccaccactct gatcagtcag catccactaa cgttgaagca aggccctcca ccagcaaaaa   11940 agttacaac accctgaagg ctcagatgat tgttagcatt tttcagcaaa aaattctttt     12000
taaattaaaa tgtatacatt gttattttag acataagact attgtacaca aatagacta    12060 cagtatagtg taaacataac ttttatatgc tgggaaacca aacaaaattg tatgactcac   12120
tgtattgtga tacttgcttt actgcagtgg aaccaaaccc acagtatctc tgaggtatgc   12180
ctgcaataaa ttatgcaatc attatcacta tctaattcta gaatattttc atcattgcca   12240
aaagaaatat tctacccatt agcagtaact ctttattccc catcactagc ctctggcagc   12300
cactattctg cattctgctt tctgtctcta ggaatttgcc tattctggac atttcacatc   12360
tgtcttgtat ataattcata tggatgtatat gcagcttttt gtattgatct tgtttgcctt   12420
agtataatgt ttttaaaatt aatccatatg ataacaggag ttagtatttc atttctcttc   12480
atggctcaat aaaattctgt tgtatggata tgccacattt tgtttatcca ttcatcaatt   12540
tctggacatt tgggttttcc attgtttggc tatgcaagtt tttatacaat tgtcttgata   12600 tgttccctagt agtcaaattg ttggattata tggtcactct gttaaacttt ttgagaaact   12660
gcaaactgtt tctaaagagg ctgcaccatt tgcgtttcta tcagcagtta aggctctgat   12720
ttttctactt tctcaccaaa gcttgttatc atctaacttt ttattctagc tatctctgtg   12780
ggtgtgaagt agtatctcat agtgatactg attggcattt ccttgatgac taatgatgtc   12840
aagcatcttt tcattattgg ctgttattat cagccatttt atatatcttc ttttggagaa   12900
ttgtttattc aaatctttca cccactttta aattggatta tttgtctttt catttttata   12960
gttgtaagag ttcttatat gctctggatc ttagaccttt atcagatatt atattttttc     13020
ctcccatcat ttgtattgtt ttttattttc ttgatagtgt cctttgaagg acattttaa    13080 cttttatgaa gtccaattca tttactcttg ttgcccatgt ttttgttttc atatcaaaga   13140
aactattgct taatccaaga caacaaagat ttacatctat gttttattct aagagcttta   13200
tagtttcagt ctcacatgtt ggtctttgat tcatattgag ttaatttatg tacgtggtgt   13260
gaggtagggg tccaacttca ttcttttttca tgtggctata cagttgttcc tgcatctgat   13320
attgaaaatt atattttccc tcattgaatg tctggacacc cttgttgaaa ataaattgaa    13380
ctcaaatgta tgggtttatt tctgacctct ccatggtaat ccattgatat ataatcccta    13440
tgccaggacc agacagtctc aattactgta gcttggtgtt tagttttgaa atcagttttg   13500
tctttcaatt atgttttttat tttcttaaaa tcatttatac tgatgaaatt gctgatattt    13560 atttttatgga ttgactacct tttttttaggg attagtatat taaatagctt tataatttaa   13620
atgcaatcta aatctctctg gtgatgtcat atctctgagc aattactaaa ccatgtgact   13680
```

```
ccatatacta gtaagtatgg tccagtgagt ggcatggaca gaagtaatga cagactgtag   13740
agaagtggtg gggagcttaa gagtattctc ttccttatag ctctcaagat ccgttttcat   13800
tctcccatta gattttgatg atatgctcat catttggtaa gagcacatga taatatatta   13860
agtataatgt tattgattta tttagagaca gagtctcact ccatcaccca ggctggagtg   13920
cactggtgtg ttcttagctc attgaaatct ccacctccca ggttcaagca attcttgtgc   13980
ttctgcctac caagtagcta ggattacagg catgtgccac cacacccagc taattttgt    14040 attttagta gagatgggtt tttgccatgt tggccaggct gttctcaaac tcctgacctc    14100
aagtgatctg cctgcttcag cctctcgaag tgctgggatt acaggcatga gtcactgtgc   14160
ttggcctaag tataactctg taattgtcct atctgtttaa aacatctttc cattcataat   14220
tcccttattt tcttactttt gatatataat tttatttta tgtagtgaca tctatataat    14280
aaaatttcag atggttcaat ttgggcacca aggtgggagg gatcagggac tggtgtgaaa   14340
ttgatacaga aatagttttc ctataaagcc acaaataagt gatacttgga gaagaaagaa   14400
cttgtctttc ccccttgaat aatcttggca tcctcatcaa acatcacttc accagagatg   14460
tatgggttta tttctggact ctccaattcc attttgttca tctgtatatc tgtcctgggt   14520
cagtaccaaa ctgtctttat tactctttct ttggataagt ttgaaatcgg gaaatatgaa   14580
tcattttact tttttttttt ttgagattgt tttggttcat gcataaacta atttgggacc   14640
atcattttcg taataatgtt taaaaatgct tgtggtccat gaacatggga tttttgttcc   14700 attatttgt atcttttaaa ttttctttta acaatatttt atagttttca gaatataggt    14760
tttacccttc ttttgttaaa tttattccta agtatcttat gtctctttaa tgctattgca   14820
aatggaattt tttctttatt ttaaaattat ctatgatttc taactctcca ctccttgtat   14880
acttacctaa gtatgtgtct tatttccccg tactagtcca tatgtatatt aaggacagat   14940
tttatgtttg agtcatcttt gtatctcaca gactattagc ccagcatctt acacgtagta   15000 gttttcaaa tgtttaatta ataatttatg gattgttaat caacaccata aattaatgaa    15060
aacccagagc taattttgaa taatctagga agcctgtttt tttaacatat gttctttgga   15120
aatttgttat gaattaaata tcaggtactt tttgatatca atatgaacta gttttggatg   15180
ttatacaata tttttatcc ataaaaaatt attttaccta aatataactc acatggttga    15240
actacataac tcttagtcac cacagcaaag gctgtttcaa aatataaagg ctgctagaaa   15300
tggccaaacg ctttctagga ataactcagt ctaattgtag gcaaatacag ggctatccct   15360
ttattttaag ttgtaaactt ataaatctaa tgactaatcg gttataatat actttcacaa   15420
cttccaatat ctttaactgt gactctattc cagaggcttt cacagattca acttctgtct   15480
ttgcactgac agctctcata tagcctgagg tctacatttc tcccattaac tctaggacca   15540
tttaattcaa atatctagta gatatctcta cccagatgta ctatggcacc tcatgcataa   15600
tagtcaacta attgccatca catttagcct gttcctgctt ctgtattctc tatcttaggt   15660
aattttagca ttttcctagt ctttcaattc tgaaagccta gaatcatctt tgatggcctt   15720
catctcatcc atcaccaaat tctatagttt aatatatcat cttaacaccct gtattatcca  15780 tctattctat agacttctac tactagtctt agttcaagta gttgtcagat ctcaccggga   15840
ccacttctgc agctgtcagt gggccctgac taaccttcct gcctcccctg tgcatctggc   15900 cttttttaatg atgcttgagt tatctgtccc gattcaaatc tgttaccatt tttcttcttt   15960
ttaaaaactc tttaatgaag tatctctccc ccagcaccta tcaggatttg gtcttgcatt   16020
```

```
tgattggttt gctaacagaa gtagccaaag aaggatcaaa ttctagccaa atattgcttc   16080
aaaaatatgt gtaaataaat ggacaatgtt taaataattg tagttaacaa ataaggaaaa   16140
tgtaaattga ttacaataaa aattagtttt ttaatatcaa tttatgctag agtaaaatat   16200
aaatttcctg tttatatgac tcagtagcat gactaatcag ttgcaattta acaagagaca   16260
ttgcttttta agaggcaagg cttttgtttt tatgaataac ttttttctag ttataaaaat   16320
taaagaaaaa tagactaatt aaaagataga gactgcctga gtagatttta aaaccctac    16380 tttacgttgc ctaaaagaaa cctactttaa atataaagat acatatagat tgaaagtaaa   16440
aggatgggga atgatacact atgttaacac taatcaaaat gggagtagct atattcattt   16500
cagtcaaagt caacttcaga gcaaggcgga ctatcatgga tataaagagg gtgcattaca   16560
taataataaa gggccaatta tccaagaaga cataagaatc cttgctctgt acatatctaa   16620
aaacagcatc aaactctgtg aagcaaaaac tgataaactg caagaaatac atgtatctat   16680
tattatagtt ggaaacttca cagccttctg tcagtaattg acagattcag cagggaggaa   16740
atcagtaagg ttacagatga acttgaaagc accataaatc aactggatct aattgacagt   16800
tataaaatac ttcatcaaac aacagcataa tacacatttt tctcagactc acatggaata   16860
ttccccaaaa ttgaacatgt actgagccgt aaaacacacc ttaacaaatt tttataaagt   16920
acaagtcatg cacaacatgc tctcaaccaa aatgtaattg aagtagaaat caataaaata   16980
agaaaaatag gtggaaaatt cccaaatatt tggaaattaa aaacacaatt tttgataaca   17040
tatgggtcaa acaaaatgtc tcaaagaaa ttttaaaata ttttgaatta aatgaaaaga    17100
aaatagatat ttgcatgata cagtgagagc agtgcttagg gtattaaatg catagaaaga   17160
aaagaaaaag atataaaatc aatagtctaa tcttccacct taggaaaaca gaatgagaa    17220 agaaaattaa aactaaatta atcagaagaa aataaataat gaaattagag atgaaattga   17280
gaacaagaaa ttagtagagg aaaatcaatg aaaccaaaac tggttctttg aaaagatcaa   17340
taaaattaat aagcctccag ccaggctgac cacgaaaata agaaacaaga cacaaactac   17400
tactatcaga agtgaaaaga gagccatcac tactgattcc atggatatta aaagataat    17460 gaggtaaaag tattttgatg gttaattta tgcattaact tatcttggcc aaggaacacc    17520
aaggattgcc agcagccacc aaaatctagg agaaagtcat gaagtggttt caccacagag   17580
cctccaaaag gaaccaaccc tgccaacact ttgatgtcag acttatggct tccagaactc   17640
tgagagacta aatttctgtt gttttaagcc accctgttca tggacatttg ttatagaagc   17700
cctaggaaac tcaaataaat ggtgacaaaa gtggacaaca tcctgaaaaa aaattcacta   17760
acactccact ttgaagagag gccgtggaaa tgtctactgg ggaaaagcaa gtgaattggg   17820
gaaatgaccc ctaaatatgg tagtctctat gaaaagcaaa acacctcttt ctcagttggg   17880
aggaaacttg aagaccaaat gagcactctt tcctcatgca ggccagctca ccatacacca   17940
tgatgcactt taacaaaagg taaattgtta aaaagagagc acagtgttaa taacagggaa   18000
ggctatgcat gtgtgggga c agagagtatc tgtgggaaaa aaacagtttt cttattctc    18060 tccctcaaca caatcaaca taggagactt ctatgaccaa atgtgtgaga gtttttttcc     18120
tcatattcta agcaaagaat caattctgca aggacacaa gctggctgtc aattcaatta     18180
tgacactatc tatctgaaga cagcaccaca tagcacaggt tgaggctgtc ttcatgactc   18240
ctccttcccc ctccacccccc atttcagatg ccaatcacaa accctaggat gtctaacctg   18300
tgcttctgac caactggctg tacaatgggg atcccacaac ctgctccttg ggtttaacta   18360
atttgctaga gcagctctca gaacttgggg aaatactaat atttatcatt tcttataaag   18420
```

```
gatattacaa aggtacagat gaagagattc atgggcaaga tatgggagaa caggtctgga   18480
gctttcttgc cttctctggg catgccaccc tccaaatacc tccacatgtt cagctatttg   18540
taagctctct ggagagttag gcatgactga ttaaatcatt ggccattggt gatcaacata   18600
accttcagcc cctctcctct ccccagaagc tgggggatgg ggccgaaagt cccaaccctc   18660
tatttatgcc ttgttatcct aggggctggg actggggctg gagctggggg ctgcctaggg   18720
gctgccagat accagtcatc tcattagcac agaaaaagac attcctttgg aggtttcaag   18780
gattttatgg gttgtgtgtc aggaatctgg gacaaagacc aaacatacag tcatacgaca   18840
caatgtttca gtcaatgagg gactgcatat accatgatgg ccccataaga ttataatgga   18900
gttgcaatat tcatattgcc tagtgacatc atatctgtgg taatgtctta gaatgcatta   18960
ctcacatgtt tgtgatgata ctgatgtaaa caaacccatt gcactgccag tcatataaag   19020
gtatagcaca gtagtgttca gtaatgtcct aggccttcac attcactcat ggctcactca   19080
ctgactcatc cagagcaact tgcagttctg caagctccat tcatggaagg tgccctatac   19140
aagtgtacta ttttaatat tttataccat atttttactg tacctgttct atatttagat   19200
atgtttagac acacaaatac ttaccattgt gttattatta tctatttagt gcatgctatg   19260
caggtttgta gcctgagagc aatagactat accttatagc ctaggtatgt aataggctat   19320
accatttagg tttgggttct atgatgtttg tgcgatgatg aaatcatcta atggcaccat   19380
tacaatgaca catttctcat aatatatccc ctatcattaa gtgacacata actgtatttc   19440
acagtatcac aatgtacatg aggaatctct ataccttctt ctcattttt tgtggaccta   19500
aaattgctct ataaaatagt ctttaataaa aagagagaaa gaggacagtc cctgtccacc   19560
aacaaaattg accacaggtt ttcccacttc tcagtgcact accattgcca cataccctt    19620
cgcatatagc tgtgttccca ggcttccaa gagcacacag agcagataat actgtggctt    19680
cacttagaaa ttcaacagag aagtgactgt gataagtgag aagaggatca tgagatatgg   19740
agtcaaataa atatcagcac agagtggtcc actttaaatt taagatgaaa ataacataca   19800
acgatacaga aatgccacag caaaataaaa agactaaaag aaacctagaa tataagcatc   19860
cattctggaa gggggcagac acgaagaaac agaataaaaa ctttcatttg tacttcacgc   19920
catagtttta aagtacacat gaattttaca acagaatatc aaagagtagt tgataaaaga   19980
atagaatgag atgaaaaaat attatacaac caaggaaata cattgaaatc caaaattatg   20040
cactccctcc atttagatg tgacaaaagt gttagcaaca acaagaagaa tgaacaaaaa    20100
atatgaaata gatttgttat aatcaccata aatgcacagt aaaatacaa ataccaaaca    20160
gttgctgaaa caataaaaga taagaagaga tgatagtgat ccattttatg aataattgtt   20220
cctaccaaag aaaattcatc gaatggaaga ataaacaac ctatgataga ggaaatttt     20280
tccacaaatt gaggcaaaat ggaatgaaca gtgctaggta gtatatcatg tactataaaa   20340
attgattcaa catgattgtt actaagttat atcttggaaa agtgactgaa tttcaagagc   20400
aaggaagaat aattctaaag gtggaaatgg caagtcagtt ggaggagaat cagagtggct   20460
tcagattttt cacatctaaa tgcaaaagat aatggaataa tgtctacaaa attctgagag   20520
ataaaaatgt ggctcagaat ttgatacctg gacaagatgt tgttcaaata taagtgcac    20580
aggcagaaat ttatgtatgt cagaatttag gcaatagaac actcatgagc cttttcaagg   20640
agaagatgga gggggagggg agctactgga tataaaatcc aaccaaccaa gagaaaagtg   20700
aagacactgt agtaaaaggt caattgatag cacaaaattc acttccttgt agaattagag   20760
```

```
tagcctcttc aaaatatatt atattctttt attttcctca tggttcttgc tactgtctca   20820
aattatcata tttttaggac agagactctc tgtcttgata atccttgtat ccccaccatc   20880
tagaatgtta cctggtacag acaagaccct tcataaatat ttattgactg actgagtgaa   20940
tgaacatagt ttacattaaa aaaaacttaa atgttatttt aaagttataa aattacagtg   21000
tagcataaaa ttatatgtta tatcgtgtat atagtataat tcaaaattat gttgtaaaga   21060
tgttgatata cataagtgac tgtgttagac acttctggct gccatatcaa agaaccatgg   21120
actttggtac tttggtggct tataaacaag agaaatttat tcctcacagt tctggaggct   21180
ggaagtccag gattgggtg gcatatggtt gggttctggt gaaggacctc ttccaggttg    21240
tggactacca gcttctcata tcttcacgtg gcagaatgtg aaattttcag atggctagag   21300
agctctctgg tgtttctta taaggcacta ccaccattca ttagaggttc accttcatga    21360
cttaattacc tcccgaaggc ctcactttct aacgacaaca cattgggggt taggatttca   21420
acatatgaat ttcgaggaga cacaaatgtt cagttcataa cagtgacatt ttaaaatcat   21480
tatatgactt atagtcttca ccatattggc tctatcagtg acttctcact attggtttat   21540
gtgctactca tatttact tgcagtttac ctaatggctc gcttatttt gcttaaccag      21600 gtggtgttta gagttatgct ctcaaaacag aacactctct tctgacagtt tggtttatca   21660
tacttggctg ctttgcttta catatttctt taataaatct ttatctttga tctgcctgtt   21720
accaccccac ttcagctcac tagaatcttc gaatatatcc atctcatact tcatctctca   21780
aattgtctca ttaatcacag gttatatagt tgaaattgat atttaaagtt caagtaaata   21840
gttataaagt acagcatata agcatttgtg attataaatt tacagttgcc acatatgtta   21900
attggtaatt agatcgctgc ttgtaggatg gtatataacc attactgcat attaacctta   21960
agactaatga gtgagagctg gccatgatg gctgactaga cacagttgca gttggaggcc    22020
tccaccgaga ataacaaaaa cagcaagtga atcctgtgct ggcaactaag gtatccaggt   22080
tctctcattt ggactgacta ggtggttggt gcaactgaca gaaagcaaag aaatcagagt   22140
ggagtaatgg cccacctgca gggggtaagt gggactccca tccccagcca agggaggcag   22200
tgagtgattg gccatcctgc ccaggaaacc atatttttcc gtggatgggt gcaacctgca   22260
aatcaggaga ttcccatcat aagcccacac caaaagggcc ttgggttcca agcacagagc   22320
agtgcatatt ctctcagtgg ccactgggct ggggtctgcc taagactaca gagttcctag   22380
agggaagggt agccaccatc gctatggcta cctgctgcct aagatgactg aacttagaaa   22440 agggggcagca accatcactg cagctccagt ctgccttttc ccctgctggt gccagagata   22500
ttgggtggtt cagatccagg aggaattctc cacagtgcaa cacagcagct gtggcagata   22560
atcaccagac tgcctcttta ggctgcaccc ggacccatcc atcttcactg catgtggcct   22620
ccctctggga atttcatcat ctccagccag gggtttacgg acagagctct gatacccctg    22680
ggatggagct tctgggggga ggagcggctg ttgtctctgt ggatcagcag acttagtctt   22740
ttccccgctg gctctgagga atccaggcag ttcagacgag tgggattcca gccagagtgc   22800
ttcattaagt gggtctttga tcctgttctc ctgactgggt gagaccaccc ccaacagggg   22860
tcaccagata ccttatatag agacattccc actaacatga agtcaataac cctctgggat   22920
ggagctccca gaggaaggag cagtaagcca tctttgctgt tgcgcagcct ccactggtga   22980 caccccagg ggtgggagag acccaggcaa atagggtctg gagtgaaccc ccagcaactg    23040
acaggagcct tatggaagag gggcctgact gttaaaagaa aagcaaacag aaagcaacaa   23100
caacaacagc atcaacaaaa aggcacccac agaaacccca tccaaaggtc agcagcctca   23160
```

```
aagatcaaag gtagataacc tcagcaagat gagaaacagt caatgaaaaa acactgacaa    23220
ctcaaaagcc agagtacctc ttcttgaaat gatcgcaaca cctttccaac aaggcacaga    23280
actgggctga ggctgagatg gataaactgg cagaagtagg cttcagaagg tgggtaataa    23340
tgaacttcac tgagccaaag gagcatgtcc taacccaatg caaagaagtt aagaaccatg    23400
ataaaacatt atagaagctg ttaaccagaa taatgtttag agagaaacat aaatgacctg    23460
atggagctga aaaatacaac acaagaactt cccaatgcaa ccacaggtat caatagctga    23520
atagatcaag tggaggaaag cacttcagaa cttgaggact atcttgctga aataagacac    23580
aaaattagag aaaaaaggca tgaaaagaaa tgaacagaac ctgtgagaac tatgggatta    23640
tgtaaaccca caaaacctac gcctgattgg ggtacgtgaa agagatgggg agaattgaac    23700
taacttggaa aacatgcttt aggatatcat ccaggagaac ttcctcaacc tagcaagaca    23760
gggcaacagt caaattcagg aagtacagag agccccagta agatacgcca tgagaagaac    23820
cactccaaga cacatgatca tcagattctc caaggttgaa atgaaggaaa aaatattaa     23880 gggcagccag agagaaaggc caggtcacct acaagggaaa gcccatcgga ataacagcaa    23940
acctctcagc agaaacccta caagccagaa gagattgggg gccaatattc aacactctta    24000
aaagaaaaat gtttctaacc agaatttcat atccagtgaa actaagcttc ataagcaaag    24060
gagaaataaa atcctttcca gacaggcaaa tgctgaggaa atttgtcatc accaggcctg    24120
ccatgcaaga gttactgaag gaagcactaa atatggaaag gaaaaatgat taccagccac    24180
tacaaaaaca cactgaagta cacagaccaa tgatactatg aagcaactac atcaacaagt    24240
ctgtaaaata accagctagc atcatggtga caagatcaac tgcacacata ggaatattaa    24300
ccttaaatgt aaatggccta aatgccccaa ttaaaaggca cagagtggca agctggataa    24360
agagtcaagg tccactagtg agctgtattt aagagacaca tctcatgtac aaagacacat    24420
ataggctcaa aatagtaaaa tctaccgagc aaatggaaaa cagaaaaaat caggggttgc    24480
aatcctagtt tctgacaaaa cagactttaa accaataaag atcaaaaaag ataaaggcat    24540
tacataattg taaagggttc aattcaacaa gaagagctaa catcctaaat atatatgcac    24600
ccaatacagg agcacctaga ttcataaaac atattcttag agacatacaa agagacttag    24660
actcccacag aataatagtg agagaattta acactgcact gtcaatatta gacagatcat    24720
tgaggcagaa aattaacaag gatattcagg aattgaactc agctctggat caagtggacc    24780
tgatagatat ctacagaact ctccacccca aaataacaga atatacattc ttcttggcac    24840
cacatggcac ttactgtaaa atcaaccaca taattggatg taaaacactc ctcagcaaat    24900
gccaaagaac tgaaatcaca acaaacagtc tcttagacca cagtgcaatc aaattagaac    24960
tcaattttaa ggaactcact caaaagcata caattcatg gaaattgaac aacccgatcc     25020
tgaatgactc ctcggtaaat aatgaactta aggcacaagt caggaagttc tttgaaatca    25080
atgaaaacaa agaggcagtg tgccagaatc tctggaatgc agctacagca gtgttaagcg    25140
agaaatttat aaaactaaat gtccacatta aaagctaga aagatctcta gtcaacatcc      25200
taacatcaca atgaaaagaa ctagagaacc aagggcaaac aaaccacaaa gctagcagaa    25260
gacaagaaat aaccaagatc agaaaagaat tgaagcagat gtagacataa aaacccttc      25320 aaaatattaa tgaatccaga agctggtttt tgaaaaaaat taataaaaca gactgctagt    25380
tagactaata aagaagaaaa gggagaagaa tcaatatac acaataaaac gataagataa       25440
atatcatcac tgaccccaca gaaatacaaa caaccatcag agaataccat aaacacctct    25500
```

```
atgcaaataa attagaaaat ctagaagaaa tggataaatt cctggacaga tatatactcc    25560
caagactgaa ccaggaagaa gttgaatcct tgaataggcg aataacaagt tctgaaattg    25620
aggcagtaat aaatagcctg ccaaccaaga aacccgcga ccagacagat ttagagctga     25680
attctaccag aggtacaaag aggagctggt accatttttt ctgaaattat tccaaacaat    25740
tgaaaaggag ggactcctca ctaactcatt ttatgaagcc agcatcattc tcacaccaaa    25800
acctggcaga gatactacaa aaaagaaaa cttcaggcca acatctctga tgaacgtcaa     25860
tacaaaaatc ttcggtaaaa tactgccaaa ccaaatccag gagcacatcg aaaagcttat    25920
ccaccatgat caagttggct tcatctctgg gatgtaaggc tggtgcaaca tacaaaaatc    25980
aataaatgta attcatcaca taaactgaac taaagacaaa aaccacttga ttatctcaat    26040
agatgtagaa aaggcctttg ataaaattca acatcccccc atgttaaaaa ctctcaataa    26100
actagatatt gatggaacat acctcaaaat aacaagagcc atttatgaca aacccacagc    26160
caatatcata ctgaatggac aaaagctgga agcattcctc tagaaaacta gcacaagaca    26220
aggatgccca ctctcaccac tcctgttcaa catagtattg gaagttctgg ccagggcaat    26280
caggcaaaag aaacaaataa aggtaggcaa ataggaagac aggaagtcaa actgtttgcc    26340
gatgatgtga ttttatatct agaaaacccc attgtctcag cccaaaagct tcttaagctg    26400
ataagcaact tcagcaaaat ctcagaatac aaaatcaatg tgcaaaaatc acaagcattc    26460
ctatacacca acaatacaca aggagaaagc aaaatcatga tgaactccc atttacaatt     26520 gctaaaaaga ggataaaata cttaggaata cagctaacaa gggcaagtga agacctctca    26580
gggagaaata caaccactg ctcaagtata tcagagagga cacaaacaaa tgaaaaaaca     26640
tgtcatgctc atggatagga agaatcaaca ttgtgaaaat ggccatactg cccaaagtaa    26700
tttatagatc caatgctact cccattaaat taccattaac attcttccca gaattagaaa    26760
aaactaccat aaaattcata tggacccaga aaagagccag tattgtcaag acaatcctaa    26820 gcaaaagaa caaagctgga ggcaccatgc tacccaactt caaactacat tctacaaggc     26880
tacagcaacc aaaatagcac agtactcata caaaaacaga cacgtagtcc aatggaaaag    26940
aatagagacc tcacaaagaa gaccacatat ctacagccat ccgatctttg acaaacctga    27000
caaaaacaag caatggggaa aggattccct atttaataaa tgtttcctta atattccatt    27060
attttaaaca tttattaagc atctgctaat agtaatctgt caactcaaat ctgaatgatg    27120
tattcccctc ttcaagaact ctagtgactc agagtggaat aacaatttta atgggacttt    27180
gaagaatgta tagttcttaa ggaggcaaaa atgaaaggga atgccatttc atcagagagg    27240
actatttgag tcaaagcttc gaatcctgcc tttccatgca attttgcatg catttatgaa    27300
atggctgtta aagattgtgt gcaagctgtt aaataatgag cacaggtata aaaaagacca    27360
gtttaccaga ctatgaggtt tagttttgaa agagagctag actcttaaat aaagaattgc    27420
aatgcaatgg gataatgctg ataattacag ttgaaaatgt ttagggatac caactaattt    27480
gacctggggg cttggtaatt agatttaagt caatggcccc atgtagctct agaggagatt    27540
tggatgtaga aaagttggaa ggtagggtat ggctagattt tgcaagacct tacataccag    27600
gccgaagaat gtgaacttga tctttaggac tatataataa ggagcgatca ggcttttaaa    27660
ctgcagcagt gtagaattaa atctgggatt tagaaagata attcatatgc gccatataaa    27720
ataaatttgt gatgaaaagc attcagaaag ataggttatt tcagcattcg tagttggcac    27780
tgttgagtat ggcatgtttc tttttaaaaa ccatagtaaa atttacagat ggcagctgat    27840
gtcctctgaa agtttgggag tatgtgattg atgatattgt cattcaatca gtaattttta    27900
```

```
ttacatgaaa atacaatgga aaactcaaag attgataaaa tatagttctt gcattaggaa  27960
caagcaaata aaaggcagta gtgaatgcat ggagtcctta aaggtagttt cccaaaagga  28020
agagtaaaac tgaaatggcc cccagcacct ggagagaaaa aggagaaact gcaagttgga  28080
gcaatgagat gaatgctaat gccacaacat aattacaaag tccgtcctag tgaagaagga  28140
aggcactttc agattgccct tttttatagg tgcctgttgt tgtcaaggcc tgttctcata  28200
cctggccaga cttccattaa gtctgtgcat tcaactttga ggacaatgat gcgtctaata  28260
ctcccaggcc tgaatagcta ttttatgaaa attactatat tggtattttt atttgttttg  28320
aacccacatc tatgcctgca ttagatatta taaactttat tatctagctt ctttaccatg  28380
tgcagataga ggtgaatctc aactagacaa ccgatgaaga cattgtcgat cacataatga  28440
taatatttgt gcttcagttg tttttctctt aatggtgctt attatgcagg ttattaattc  28500
aaagaccatc attggtattg aggaatgtga gagtaggaat gtcatttata gagatgaaaa  28560
gtttctattc accatgaaga tcacagatgt tttcatctgc cagggagtaa tttatactgc  28620
atctacttat gttatgaccc gtgtggaccc tgtgtcaata ttgaatctga atatgccact  28680
tgctagctat gtgacattgg ataaattact taatccttct gtgccttagt ttccttattt  28740
ctaaagtggg gataaaatta ggacccatac ttcatagggt tatttttaaat aaattaaatg  28800
ggctaatata tgtaaagctc atggaacagt gcctggaact taagcattca acaagtcata  28860
gttcttgtca tattattaat gttagaaata atgtctgcaa caatgctctc taaatttcct  28920
atctcacatc cttaagaaca gatgcaaata aaaacctgta atatttgaaa atggctagaa  28980
attgtgtgat ttatgagagc aaaattcaaa catacacaat atgattttgc attcacttta  29040
gtccctctt  atccaacatt tcagcttctg tggtttcagt tacccaaaaa tcaatgaagg  29100
ttcaaaaatc ttctatggaa acttccagaa ataattcgta aatttttaaat tgtgtgccgt  29160
tctgagtagc atgatgaaat cttgcactgt ctcactctat cccatccaag gggtgaatca  29220
tcccttttgtc tagcagaacc gggctgtgga tgctacctgc ccattagtct catagtagcc  29280
ttttagatta tcagattggc tgcagaggta tctcagtgct tatgttcaag tcattcttac  29340
tttacttcat aatggcccca aaaagcaaga gtagtgatgc tagaatattg tcataattgc  29400
tctatttcat tattaggtat tgttattaat ctcttactgt gcctaattta taaattaaag  29460
ttttatcatt ggtatgtatg cataggaaga aaagtaccgc atatataggg tctggtacca  29520
tgtatggtct caggcatcca ctggtggcct tggaaagtat cctccaagga taagggtac   29580
tactgtagag aatgtagaag tggctatta  ataaccacta aatatttatt tagcatgaa   29640
gtgtttgaag taaatcttaa cacagaggtc cagtgaagtc ccaagccctg actatcctgt  29700
atcatcctta cgcttacttc taagcgcccc cccagttacc ttatgaaatc ctaggactac  29760
atggaatatg atctatgaaa accactgccc tagtccaatg tactcatttt gcttatgaga  29820
aaattcaagg agaggttaca gtaagtcagt aaaacgctac aggaagaaaa aggactggaa  29880
atgaaatgct ttggtcagag tccccacttt gcccctttgg ctatgagatg ttggacaatt  29940
cagttaactg cttgaaagcc tgatttttcc aattagaatt ttgattttca taatctctga  30000
gatccattcc tgctgtaaaa ctattcaatg tcagaaatga acacagtcat ccacaaactc  30060
tagtttggtg ttcttttcat tgcactgatg tagaagtatc gactacttag gagaaccaaa  30120
gaatgaatgc cctggatgaa ttccataata acctttctgc acatccagag taggatatgt  30180
ataattttgt gacgtatggc actgtaccaa gtacaggtga atatgccgtc aggttttcaa  30240
```

```
tagttatgca gtgtgtgtat ttaacatgaa cactgatagc taggcaaatc tgccaattgt    30300
tgaatcatat agttcctgga acaccatttc ttatccccaa acttatataa ccacacctgg    30360
attaaagtaa attaataaaa tactacgttg tgtacctaag gtgtgttggt aaagctggaa    30420
aaggcaactc atgaataaaa aatatatatt acctccagaa aaataaatgt aatgcataca    30480
caactttaca caagttaaag aatgggttta acaactaaga tttgttcatt acccttcat    30540 gagacattct tttgttctgt attcattaca ttattagatt ttctagtgaa tttcaccaat    30600 tgattttct taagttgagc ttcatcagag aaattctgta gaggtatttt cacaaatgaa    30660
aactcacaat cacaagtttt ctaactcttt tgcataaaaa agcactgagg cactttcat    30720 gatgatatta ttctgaaaca ccatatttaa gaatatagtc atttttattc tttgtttgtt    30780
ctttatgtcc taatgttctc tacagtggat tccatcaata ttaattgtta aaatattaac    30840
tttctatttc tgccattgtt ttatgtacca cagagacatg tattagaaaa cacgctatgt    30900
tatgggtgta agttaaatga gaagcacagt gccaataaat tgcacgagaa ttgctttact    30960
tgggctattc ttggtcatag gaaggactgg gaaattaata tagtcacgtt tttatagatg    31020
cagagctttt attaattaac atacagttgt taattagtag tatatgttca cctttgttat    31080
taacataaaa tttagtacaa aacacttttg ggatattaaa ttttggtatt aaatatgtcc    31140
tatttcatac atgttagaat ataattaata tatacttatt gtcatcacaa agaatcaatg    31200
ctaaagtcaa aaaattccag gtacttttt tccttcttgt taacctagca atgttgggca    31260
ttagatgaag aagaggcaag gctacagggt tagataagga tctgcagtct tagtctttgc    31320
aaatacttgg tatctcttgc cttctcaaaa cttaggcatt gaaaattatt ataagtaatg    31380
aaatccaaaa tgttagatag ggtaaacaca gttgaactca caaatatatg tttttttttc    31440
ttttctctgc tcttttggta gaaaatgtag aacatgatta ataaggttgg agttttttct    31500
ttataatttt tttcacagtg gcgttccaaa ctaaagaatg cttgtttacc taatatggcc    31560
aaattggagc cagtaccttc attcagctag atttaccccca gttgcatatt tgcaatgagg    31620
cagaattcct acagacagcc ttccttctga ttttctgcc tttgttcctc ctcacactgt    31680
gtttctccca taattcacat ctaccctcta cctaattggc ttctccagtc aaagtggata    31740
agcatctcag tcagaaatac attatgagaa cttcccaaac atgtactaat cgccacaaac    31800
caaggctcag atcatgccat atcgctgctc aacaactttc cttaggttac cactcactgg    31860
ctattgcagg actaattcct tatgtgggca ttggagaagg aaaatctgtt ctttacatt    31920 ctagcctact tgccactctg tattgcccct tacacgccca gcaccacaac caaattggat    31980
tacttactgt ttccaaaata tgctccacat ttttgtacct cagtgccttt gctgttttct    32040
cattgtggaa ttttctactt cccctgtctt gctccacaaa tcttcccgca cccaaattta    32100
aagacagcag gaattgaata acatcctttg ttcaataccg ttcgttatga cattgatgag    32160
aaaaaagtcc atttctggcc ctggaccact gtctgtgtag agttagcaca ttctccccgt    32220
gtctgtgtgg gttttctctg ggtactttgg tttcctccca catcccaaag acgtgccac    32280 tgggtgaatg ggtatgtcga catggtccta gtctgagtgt aggtgtgtgt gaatgcaccc    32340
tgtgatcgag ggtgtcctat ccaggactgg tccgtgcttt gtaatctgag ctgctgagat    32400
agactccagc cacctgaact agaataagca gtttggaaag tgaccctgaa ctagaataag    32460
cagtttggaa aatgaacaaa tcaatcaatg taaattattg tcaaataaaa atttgttaag    32520
taaatggtca ttatacaaat acacaacaat aaatgatgca agacgaaggt gctcatccag    32580
ctgtgagtca gccttacttg tttgtgattc ttttttaact gtgtggtgga agtgctcctg    32640
```

```
acagttttag ctttgcaaac acttatttct tgacttaatc caccaccact atgaccatcg    32700
acactcactg atttacaaaa acatgggtaa ttatcttgtt tttgttaatc tttcttaaat    32760
gtatgtgtag ctcatattta attcagtgtt taatattaga aatgtttggg gtcttcattt    32820
agaaatttgg cgatgttttt gtgatgagaa atatgccaca ggatcttaac tcttttttat    32880
atcaattaac ctacggtaaa attggtttct ttgtacaaca gtttacttaa agtcgcagtt    32940
tccaagaacc tatccgtgat gttagatgag gacttactgt gccatttaag gtcaagttca    33000
ggttctactt tattcataac gcaagtcaaa agtagtctta ctgttgcact ttatcttgaa    33060
cactattaag gaaggtatca ttctatattt tatgcataaa atctgaatat gcatatacat    33120
tcaatatttt ttttaaagta gacatgtaaa tgactaagca aacaaaatgt attacaggct    33180
atgtcatgtg gtcagggctt aggattcaga aaataaatatg ttgtcttgaa ttttgctagc    33240
acttatattg tcaactcttc tattaaattc tgttgattga aaattttgaa tcaagctcac    33300
attacttata tgacaaattc gggtaataga aaaagcatgg gctttgtaac caggcaaacc    33360
agtatttgca tgctagccct gccaatcatt agttttttcca cttagtgttt ttgtgaatct    33420
ggtttctttg ggattgtgga gtgtaatgat agtgacagtt gttagatatt gcttgcactg    33480
tccattattc taggaagaaa gtttcctgga ataggaaata taactgattg ttttcccaca    33540
ggagaagaag gcacttcctc tcctctttgg ggctagaaat gacttacttt aaaaatctca    33600
gttaagagag gactaaagct gttccaatgt tatgattgta ttcccctaac tatgtgaagg    33660
tacagcagga gcaagccttt catttgtagc agtggctgca acagaaaggg gggcagtttt    33720
tagagcggcc tggcacaggg tattagtttt tgaatcctcc aggctgaaga atgtgtgctt    33780
cctcagcatg tgtaagtatt tgtgtcagta tgctttcatg tataattagt agaaaactga    33840
acataaatgg acttaaacat taaagagtta tttaatggcc tgtataactg aaaagacccc    33900
agttgaatgc tttcaactgt ggcttagaat ttcaacttaa tttctttgca attttttgac    33960
tctgcgtttc tccatgtggc attaatcttc atgttgtggc ttaccagtag ccaccagggt    34020
ttctttattc ttccatatcc agcagaatga taattccttt gcctataatt aactaagttc    34080
ttagatgtac tctgattgga ttatctatga aaaaatcctt atgtcagcgg aagacccagg    34140
tcttaactgc cttagacctt gtttaattga gcaagttgct ttggtcagag agatgggata    34200 accttttattt acttagtatc taagtcttag accaatcaaa actcaagcca gagctggaag    34260
tggtattaac tttcattaaa aaaattactg ctaaataatg gagagagaga aataggaatg    34320
atatgcaatg aaaaccacaa tgtctattgc gttgggaggt tttggagctc caacagccag    34380
gaaacagcta ggaaaacact ttctgacata ataagatctg tcccctctcc acaaatggag    34440
tgggaacatt agtgattccc actagagaag tagctttacc taggaaagtg gtgatttcat    34500
gaagttcgtc atttctatga cagcaagttg tggagaccaa ggagaagaac ctgaagagtt    34560
tattacagaa cacacattag ataacattat gggaattttc agaaattaca tggtgctttc    34620
agaggagttt atctccatca gataggaact taaaggctta aattataata atgtgtgtat    34680
aaaaaaagaa gagtgatttt attatataat cactggatag acaaaactgt aaagatctcc    34740
tataaagcaa aaggaaataa tttgtgtatc tgtctacata ctatcttcct acctatctca    34800
cttgtgtgcg tgtgcgtgtg tatgtgtgtg tgtgtgcgtg tctttgcata ttggtctgtg    34860
tatgcatatg tatatataat taagagaaga tgattgatac catagacaga gcagagagct    34920
aatctataaa taataagtgt ttctgaagag aaaatagccc atcaaaacag aagcaaaagt    34980
```

```
tcagaataaa agagagatat atttctgtat taaaatctta aacttgttga ttatgactca    35040
agggtaagag acaaacacta ggatatatca aggtgaattt tttcaaggaa gcatccttcc    35100
agtaagagag gggaaacatg tcgacaaaag gatacaatta ggttagcctc tatttttta    35160
ccaatgttta gctccaattg accaagctct actgaatttt gtgataacta ctaagttttg    35220
ttactgtggg ttcacagtct tagacccagg caaatttat tgaatgtacc aagaataata    35280
aagacacaga taggccagca agggtactgc ttctttattc aataaaaacc tgaccttaag    35340
attagtccat ttggcttttg ttgccactgc ttttggtgtt ttagacatga agctcttgcc    35400
catgcctatg tcctgaatgg taaagcctag gttttcttct agggttttta tggttttagg    35460
cctaacattt aagtctttaa tccatcttga attatttttt gtatcaggtg taaggaaggg    35520
atccagtttc agctttctac atatggctag ccagttttcc cagcaccatt tattaaatag    35580
ggaatccttt ccccattgct tgttttctc aggtttgtca aagatcagat tgttgtagat    35640
gtgtggcatt atttctgagg cctctgttct gttccattgg tctatatctc tgttttggta    35700
ccagtatcat gttgttttgg ttactgtagc cttgtagtat agtttgaagt caggtagtgt    35760
gatgcctcca gctttgttct tttggcttag gtttgacttg gcgatgtggg ctcttttttg    35820
gttccatatg aacttaaaag tagtttttc caattctgtg aagaaagtca ttggtagctt    35880
gatggggatg gcattgaatc tataaattac cttgggcagt atggccattt tcatgatatt    35940
gattcttcct acccatgagc atggattgtt cttccatttg tttgtatcct cttttatttc    36000
attgagcagt gatttgtagt tctccttgaa gaggtccttc acgtcccttg taagttggat    36060
tcctaggtat tttattctct tgaagcaat tgtgaatggg agttcactca tgatttggct    36120
ctctgtttgt ctgttattgg tgtataaaaa tgcttgtgat ttttgtacat tgatttttgta    36180
tcctgagact ttgctgaagt tgcctatcag cttaaggaga ttttgggctg agacaatggg    36240
gttttctaga tatacaatca tgtcatctgc aaacagggac aatttgactt cctcttttcc    36300
taattgaata ccctttattt ccttctcctg cctaattgcc ctggccagaa cttccaacac    36360
tgtgttgaat aggagtggtg agagagggca tccctgtctt gtgccagttt tcaaagggaa    36420
tgcttccagt ttttgcccat tcagtatgat attggctgtg ggtttgtcat agatagctct    36480
tatgattttg agatacgtcc catcaatacc taagttattg agagttttta gcatgaaggt    36540
tgttgaattt tgtcaaaggc cttttctgca tctattgaga taatcatgtg ttttttgtct    36600
ttggttctgt ttatatgctg gattacattt attgatttgc gtatattgaa ccagccttgc    36660
atcccaggga tgaagcccac ttgatcaagg tggataagct tcttgacgtg ctgctggatt    36720
cggtttgcca gtgacaaatg ggatctaatt aaactaaaga gcttctgcac agcaaaagaa    36780
actaccatca gagtgaacag gcaacataca aaatgggaga aaattttcgc aacctactca    36840
tctgacaaag ggctaatatc cagaatctac aatgaactca aacaaattta caagaaaaaa    36900
acaaacaccc ccatcaaaaa gtgggcaaag gacatgaaca gacacttctc aaaagaagac    36960
atttatgcag ccaaaaaaca catgaaaaaa tgctcaccat cactggccat cagagaaatg    37020
caaatcaaaa ccacaatgag ataccatctc acaccagtta gaatggcaat cattaaaaag    37080
tcaggaaaca acaggtgctg gagaggatgt ggagaaatag gaacactttt acactgttgg    37140
tgggactgta aactagttca accattgtgg aagtcagtgt ggcgattcct cagggatcta    37200
gaactagaaa taccatttta cccagccatc ccattactgg gtatataccc aaagaactat    37260
aaatcatgct gctataaaga cacatgcaca cgtatgttta ttgtggcact attcacaata    37320
gcaaagactt ggaaccaacc caaatgtccg tcaatgatag actggattaa gaaaatgtgg    37380
```

```
cacatataca ccatggaata ctatgcagcc atacaaaagg atgagttcat gtcctttgta   37440
gggacgtgga tgaaattgga aatcatcatt ctcagtaaac tatcacaaga acaaaaagcc   37500
aaacaccgca tattctcact cataggtggg aattgaacaa tgagaacaca gggacacagg   37560
aaggggaaca tcacactctg gggactgttg tgaggtgggg ggaggggag ggatagcttt    37620 aggagatata ccaaatgcta aatgatgagt taatgggtgc agcacaccag catggcacat   37680
gtatacttat gtaactaacc tgcacattgt gcacatgtac cctaaaactt aaagtataat   37740
aataataaaa taaaaagat tactccattt gaacaagata ttaataaata tcaataatag    37800
agaaatggtg atataaaaca atcactatta aatgctgcag tatttggtga tttctagata   37860
gctattgtaa atattaaaac acaaaaataa cttgtttcac ctaagcccta agaatataaa   37920
aagtgcgtgg ttatgggagg actgagaaag ctaaaaagat gataaatccc tcccttcat    37980 tagaatgatt agtggatatg tatactaatt agattggtag agaatataat tttaataatt   38040
attggaaaac actcttaaaa gaattatagt cttcaaatt acaagaaaa aggaaaatac     38100 aatgtagtca cttaaatacc aaaattatac caaaattata aaataaagga aaggaacaa    38160 aaagaaatag aatgactatc tgacaataaa tataaattat gttaaactcc aaaattaacc   38220
tgattgttca cactcacaca cacacactca cttgttcaca ctgtatgcac tatataagag   38280
ataaacacag acacacacac acactcactc acactgtatg cactatataa gagataaacc   38340
taaagtaaaa tatcaaaaat ttttttaatc ccttatataa aattatcaac tgatcattaa   38400
aagacaaaaa acttataaga aagtggataa gaacagacta ttcatagaaa agaagatgca   38460
aattgttaat taacatgaaa tgatgttcat cttcaagtag ttacaaaat gcaaatgtaa    38520 gctataatga ggcataattt ttacttctc aggattggta aaaatggtaa agactgatga    38580
catctgatcc aaataagaat gtaacagaat ggcctccttt atatgctggt agaagcacaa   38640
attattttaa aaatacatat accatttat tcagcaaatc tcacttttgg gaactaagtc    38700
tacagaaatg caagcattaa tataaaatga gataacaaac acatacagat acacatacaa   38760
agatgtctgt tacagaattg ttggtaggag caaatatttg actattcatc aataagtatt   38820
gaataatttg tggaacacac ttaatgtgga atattacgca gttataaaac aattgttcta   38880
gtatgtttga cctagaatga cagtcatgat ataaagtgag aatgatacaa aaatcaaagt   38940
gtaatgtata cactgtgatc ctattttta acaaaatgaa aaaggaaaat accctcataa    39000
aaccctatat atgcatgtat atatgtgtat tttctatgcc tgcagaccta acacgcatag   39060
gcataggatg ctgagctgaa agtatagagg tctcatatac tccttgtgcc cacagacaaa   39120
tttccccact atcaacagtt gctatcacag tggtacattt attatgatca atgactctac   39180
acatcattgt cacccaaagt ctatagttta gattaagatt cactcttggt gttgtacata   39240
ctatgggttt tgtcaaatgt cttcaatcca aattatatta cagaatagtt tcactctcct   39300
aacaacttca ctgttcattc tttgtgcctc tcctattcat ccacttgctc cctcttaaat   39360
cttgacaaac cacgaatctt tttactgtct ctagttttac cttttccaga atgttacata   39420
gttgcactca aactgtatat agcctttttc agtttggctt ctttcactta ataatatgca   39480
tttaagatcc ttccatgttt tcttgttgct ttatagctca tttcatttta gaactgaaaa   39540
aatattccat tgtctggaag caccacagtt tacttattca ttcacctact gaaggacata   39600
ttcattcctt ccaagttttg gtcattatga ataaagctgc tataattatt cacatggggg   39660
ttttgtgtgg ccacaaattt tcaaattctt tgggtatata gcaaggattg ctgcattatg   39720
```

```
tcgtaagaga ttgtttagtt ttgtagaaga ccaccaaact gtctttcaaa gtggctgtac    39780
tgtttacctt cccatcagca atgaatgaga attcttttg  ctttacatcc ttgccagcat    39840
ttactgtggt cagtgttttg ggttttggcc attctaatag ggtgtcatgg tatctcattg    39900
ttgttttaat ttgcattcc  ctgatggcat atgctgttga ataacgtttc atatgcttat    39960
ttgctatctg tgtatcttct ttgctgaggt gcttattcag gttttttgcc aattttttat    40020
tgggttgtaa attgtcttat tttagatttt taagagttct gtataatatt ttggataata    40080
ttattttacc agatatgtct tttgtaaata ttttttccag tctgtggctt gtaatctcat    40140
tctcctgatg ctgcttttg  caaagcagaa gttctgaatt ttaatggagc tcagcttatc    40200
aatcacctct ttcatagatc atgcctttgg tattttattt aaaatgtcat ctcaatgccc    40260
aagttcatca agaatttctc ctatgtcatt ctctaagatt tttataatct tgcattttac    40320
attgaagtct atgatccatt ttgagctaat ttttgtgaaa ggttcaaggt ctgtgtctag    40380
attaatgtta ggggtgtgga tgtgaatgtc cagttgtctt agcaccattt gttgaaaaga    40440
gactgctcca ttttattgcc tttgcccgtt tgtcaaaaat caatggatta tacttaggtg    40500
agtcgatttc tcagctcata ttctggtcca ttgatctatt tgtctgtttt ttcactaatg    40560
ctatagtgtc ttgattactg taagtttatg gtaggttttg aaattgagtg gtgtcagtcc    40620
tctaactttg ctcttttctt tcaatattga atttactctc ctgggtcttt ttcctcttca    40680
cataaacttt agaaccaatt tgtcaatttc tacaaaataa cttcctggga ttctgattgg    40740
aattgcattg agtctgtcca ttcatttgga aagaactgac atcatgacaa tattgagtct    40800
ttctacccat gacctggaat atctctccat ttatttttt  cttttttga  tattatttat    40860 cagagttttg tagttttcct catatgtatt ttggacatt  ttttttagat ttacacttaa    40920
gcattttatt tttagggctg ctaacataaa gtggcaatgg gttttaatt  tcaaatttca    40980 cttgttcatt gatggtacat agaaaagtga ttgacttatt tctcttgtat cctgcaactt    41040
ttatataatt gcttattagt tatcagagac ttttttacca atttaaaaaa attttctaca    41100
tagacaatta tatcatctgc aaacaaagac tgtattattt tgttcttacc aatctgtata    41160
cattttattt cctttttgt  cttactgcaa tagctaagtt ttgcagtaag atgttgaaag    41220
ctgaagtgaa gggagatagc tttttttta  ttatcaggaa acctacaaat ttcttattat    41280
taagtatgat attagctata ggacttttgt agatgtcctt taagttgagg aagtccctct    41340
ctattcctaa tgtgttaaaa ttttttatca tgaatgggtg ttgaatgttg tcaaatgctt    41400
tttctgcatc tattgatatg attgtgtgat ttttcttcat tggcctattg atgtgatgga    41460
ttagattaaa caatattcca atgttaaaac accttttgcat acctgaaatt aaatccactc    41520
aattgtggtg tagatgataa gtgctatccc caatagcaaa ttgaatccaa taatgtataa    41580
aagtatacag ttttatgtgg aggatttttg aatctatgtt catgagaggt acttgtctat    41640
agttttattt tcttgcagtg tctttgattt ttgatattag ggtaatgctg gccttataga    41700
atgagttgag aagtattcct cctgctcctg cttacacaca ctgtcagata gtgtggagca    41760
ttgatacaat attgtcctta actatttgat agaattcagc aataaactca tctgggatta    41820
gtattttttg ttttgtaaca tcattttta  tttattttct tgaatagata tagtcctatt    41880
cagagtttct atttcttttt gtgtgagttt tggtagattg tgccttttga gtaattgatg    41940
catttcatat aggttatcaa atttgtggat ttagagttgc tcataatatt tgtttattat    42000
ctgtttaatg tctattggat ctaaagtgat gtctctgtat catttttata tgaacaattt    42060
tcacttaata ccaatctaaa tctacttcca aataacatta taccacttta taggaggtac    42120
```

```
aagtaattta tggtaataaa atattactaa tttctccctc ctaacctttt atcactgcta   42180
tcattcattt cacttataaa taaacatata agcataattg aatacatggt tgctatcatt   42240
atttgaaggt attaactttt atatcaatta agaataagaa aaacaggctg ggggcgtgaa   42300
gattaaccac cccatgtgcc atcactggca ccaacaaatg ctgtccaggg ggctgcatat   42360
tggccaattc tactcaccac tgacagtgct tgtgtgcagc atctggtggc atgaggacag   42420
gtgcacctca ccataatttt cactaacaac cagagcctaa gccaatgaag aactctcaga   42480
caatgctgac attgatcgca tccaaataga acatacagag acgacactac tgtgctagcc   42540
cagaattaaa gccaaaacat cttccccaaa caatactata attacagcta caggaaaagt   42600
ctttctctat gaaagaagcc aatccatgaa attaaagag aaactgttaa aatagatgca   42660
cagataaggt aaggacatga gaaatatgaa aattcaagaa aaaaatgaca cctctgaagg   42720
aatacaatac ttcttcagta aaatatccca aagaaatgta aatatgttaa aaagcctgaa   42780
aaagaattca aaataatgtt cttaagaaaa tgcagcgaga tacaagagga cacagataca   42840
aatacaagag gacacaatag aaaaaaaaaa atgcattggg aaggcaattc atgtcttcaa   42900
tgagaatttc aagaaagaga gacagatata aaaagaacc cggcggcttc tagcccgccc   42960 gccctcccc cgcgcgtcgg ccctgccgag ccggccggcc ggcctggctc ccctccccgg   43020
ccccgacggg cgggcggact gccctgagga ggcggggagg ggagggctgg accggccggc   43080
gggcgggcga cgatgccgaa cttctgcgct gccgccaact gcacgcggaa gagcacgcag   43140
tccgacttga cttggccttc ttcagcttcc cgcgggaccc tgccagatgc cagaagtggg   43200
tggagaactg taggagagca gacttagaag ataaaacacc tgatcagcta aataaacatt   43260
atcgattatg tgccaaacat tttgagacct ctatgatctg tagaactggt ccttatagga   43320
cagttcttcg agataatgca ataccaacaa tatttgatct taacagtcat ttgaacaacc   43380
cacatagtag acacagaaaa cgaataaaag aactgagtga agatgaaatc aggcactga   43440 aacagaaaaa aattgatgaa acttctgagc aggaacaaaa acataaagaa accaacaata   43500
gcaatgctca gaaccccagc gaagaagagg gtgaagggca agatgaggac attttacctc   43560
taacccttga agagaaggaa aacaaagaat acctcaaata tctacttgaa atcttgattc   43620
tgatgggaag gcaaaacata cctctggacg gacatgaggc tgatgaaatc ccagaaggtc   43680
tctttactcc agataacttt caggcactac tggagtgtcg gataaattct ggtgaagagg   43740
ttctgagaaa gcggtttgag acaacagcag ttaacacgtt gttttgttca aaaacacagc   43800
agaggcagat gctagagatc tgtgagagct gtattcgaga agaaactctc agggaagtga   43860
gagactcaca cgtctttcc attatcactg acgatgtagt ggacatagca ggggaagagc   43920
acctacctgt gttggtgagg tttgttgatg aatctcataa cctaagagag gaatttatag   43980
gcttcctgcc ttatgaagct gatgcagaaa ttttggctgt gaaatttcac actatgataa   44040
ctgagaagtg gggattaaat atggagtatt gtcgtggcca ggcttacatt gtctctagtg   44100
gattttcttc caaaatgaaa gttgttgctt ctagactttt agagaaatat ccccaagcta   44160
tctacacact ctgctctttc tgtgccttaa atatgtggtt ggcaaaatca gtacctgtta   44220
tgggagtatc tgttgcatta ggaacaatcg aggaagtttg ttcttttttc catcgatcac   44280
cacaactgct tttagaactt gacaacgtaa tttctgttct ttttcagaac agtaaagaaa   44340
ggggtaaaga actgaaggaa atctgccatt ctcagtggac agggaggcat gatgcttttg   44400 aaatttagt ggaactcctg caagcacttg ttttatgttt agatggtata aatagtgaca   44460
```

```
caaatattag atggaataac tgtatagctg gccgagcatt tgtactctgc agtgcagtaa   44520
cagattttga tttcattgtt actattgttg ttcttaaaaa tgtcctatct tttacaagag   44580
cctttgggaa aaacctccag gggcaaacct ctgatgtctt ctttgcagcc ggtagcttga   44640
ctgcagtact gcattcactc aacgaagtga tggaaaatat tgaagtttat aatgaatttt   44700
ggtttgagga agccacaaat ttggcaacca aacttgatat tcaaatgaaa ctccctggga   44760
aattccgcag agctcaccag ggtaacttgg aatctcagct aaccttttgag agttactata   44820 aagaaaccct aagtgtccca acagtggagc acattattca ggaacttaaa gatatattct   44880
cagaacagca cctcaaagct cttaaatgct tatctctggt accctcagtc atgggacaac   44940
tcaaattcaa tactttggag gaacaccatg ctgacatgta tagaagtgac ttacccaatc   45000
ctgacacgct gtcagctgag cttcattgtt ggggaatcaa atggaaacac aggggggaaag   45060 atatagagct tccgtccacc atctatgaag ccctccaact gcctgacatc aagtttttc    45120 ctaatgtgta tgcattgctg aaggtcctgt gtattcttct gtgatgaagg ttgagaatga   45180
gcggtatgaa aatggatgaa agcgtcttaa agcatatttg aggaacactt tgacagacca   45240
aaggtcaagt aacttggctt tgcttaacat aaattttgat ataaaacacg acctggattt   45300
aatggtggac acatatatta aactctatac aagtaagtca gagcttccta cagataattc   45360
cgaaactgtg gaaaatacct aagagacttt taaaaacagg ctttcttata tttgatattt   45420
ggaagtaaaa gccgtaaggt gtatgtaggc cacttaatca ctaaatatct ttgcctatag   45480
gactccattg aatacattag ccattgataa tctacctgtt taaatggccc ctgtttgaac   45540
tctcaagctt tgaagaccta cctgttcttc cagaagagaa cgttgaaagt tccatgtttc   45600
cttttgcgtg atctctgttg acggcactct ggaattgttt cagttaagtc attttagaca   45660
tagcatttat tatcactgtg gatctctact tgttgggtgt tatgaattct ttgaaaaaat   45720
atattttgaa gaggtgtggg aggaaggaat acattttata aaatgttata gttaagccca   45780
caattgacct ttgactaata ggagttttaa gtatgttaaa aatctatact ggacagttgc   45840
aagaaattac cagagaaaag cttgtgagct caccaaacaa ggatttcagt gtagattttg   45900
tctttctcaa acttaaagaa acaaatgaca aagtttgaat ggaaaagcct gctgttgttc   45960
cacatctcat tgctgtttac attcctttgt ggagcctaca tcttcctaag ctttttagca   46020
ggtatatgtt gaacacttct gtttcatggt tgagacagaa tcagaggcca tggatactga   46080
caactgattt gtctggtttt tttttttctgt cttttttcca tgactcttat ctactgcctc   46140
atcttgattt ataagcaaaa cctggaaaac ctacaaaata agtgttgtgg tttatctaga   46200
aaaatatgga aaatattgct gttattttg gtgaagaaaa tcaattttgt atagtttatt    46260
tcaatctaaa taaatgtga gttttgttta aagctaaaaa aaaaaagaa cccagcagaa     46320 atcctggaaa taaataattc agtggatgaa attaaaatat atatatacaa tcaagagttc   46380
aacaatagac taaatcaagc agaagaattt ttgaacttgg tcttttaaaa taacaaagcc   46440
agattaaaaa aaaaggtggg gggggaata aaagaataaa agagaatgaa gaaagcctaa    46500
tgacatatag gacaccataa agcaaacaaa tatttgaatt ttataagttc cataagaata   46560
agaaaatgga aatgccatag acaacctatt tattgaaata atatctgaaa aattcttcct   46620
tcttgtgaag gatatagaca tctagatata gaaagctaaa atatctacta gtagattcaa   46680
taaaaatata agtgttctcc aaggcacatt aaagttacac tgtgaaaggt tgaagacaga   46740
gggagaattt taaaaatagc aagagaaaaa catcaagtca catgttgggg gaaatcccat   46800
cagactagca gcctattact cagtaaaaat cttgcaggcc aggagagcat gagaaactat   46860
```

```
attcaaagtg ctgagagaaa aatgccaatg aagaatacta tgcccaggaa agctatcctt   46920
taaaaaggat ggagaaataa catcttttc agacaagtaa aaactgaagg aaattcatca    46980
ctactagatc aaccatacaa taaatgcttc agggagtaca acatctataa gtaaaaggat   47040
gatgtctact atttagaaag cacaagaaag aattaaactc acgggtagag cagatacact   47100
aatgaaagca agaaagaaat caaagcttgt cactacagaa aatgaccaaa ctgtaaagat   47160
aaatattaaa agaggaaaga gaaacaaagg atatacagaa cattcagaaa acagctatca   47220
aaatgacagt agtaagttct cacctattat taacaacatt gaatgtaaat ggtttaaatt   47280
ctacaattat aaagtataga ctggctgaat gggtagaaaa gaaaacacaa aagacccaat   47340
tatatgctgc caacaagaaa ttcacatcat gggtaaagac actatattag tctgtcctca   47400
tgctgctaat aaagacatac ctgagactgg gtaacttata aaggaaagag gttaaatgga   47460
ctcacagttc cacatgtctg ggaaggtctc acagtcatgg tgtaaaacaa gggaagaaca   47520
aagggatatc ttacatgagg gctggcaata gaacttgtat aaggaaattc tcatttataa   47580
aaccatgaga tctcatgaga cttattcact atcacaagaa cagcatggga aagacccaca   47640
atcatgagtc aattacctcc tactgggtcc ctcccacaac acatgggaat tatgggagct   47700
acaattcaag atgagatttg ggtgaggaca cagccaaacc atatcagaca caaatagact   47760
gaaagtgaag tgacggaaac catatcccat gcatatgaaa gccaaaactt tgcaggagta   47820
gctatactta tatcggacaa agtagactta aagtcaaaga acataacaag agataaagag   47880
gtctagtatg taatgatgaa gggatcaatt cattaacagg atataacaat tgtaaatata   47940
tatggactca acactggagc actaagatat ataaagcaaa tattattaga gctaaagaga   48000
gagatagact ccaatacagt aagagttgga aatttcagca ccccacttc agcactgggg    48060 agatcatcta gagagaaaat caacaaagaa atattggact taatctgtgc tatagaccaa   48120
gtggacctag caggtattta cgtaatattt tatccaacag ctacagaata cacattcttt   48180
tcaccagcac atggaacgtt cttcaggata aaccatatgc tagtccacaa aacaagtctc   48240
aaaaattttt taaaaatcaa aatcatgttg agtaccttcc cagagtacaa tggaataaaa   48300
ctatagatca ataataagag aaattttgga aactgtacaa atacattgaa ataaagcaat   48360
aggcttcaaa gtgatcatta gattaatgaa aaaatgaaga tcaaaatgaa aaaaaatctg   48420
aaacaaatga aaatgtaaac acaacatacc caaacctatg gaatatagta aaagtagtgc   48480
taagagggaa tgttatagca atagccatct acatcaaaaa agtggaaaga tttcaaataa   48540
acatcctaac agtgcaccac aaggaactag aaaagcaaga gggatccaag cccaaaatta   48600
atacaaagaa ggcaaaaata aagagcagaa aaaaggaaa tagaaactaa aagctaaact    48660
aaactaaata ataaaactat taacaaaaca aaatttatt tcttgaaaag ataaacataa    48720
accacttgga aaataaaata aaaataaaat cctagaaaaa atttaaccaa ggagatgaaa   48780
agataaaaaa taaccacta gctggactaa ctaataaaga gagaagaccc aaataagtaa     48840
atcagaaaca aataaagcac acattacaac tgataccaca gaaatataaa ggactatcag   48900
agattatttt gagcaactat acactaacaa attggaaaac ctagcggaaa tgaatcaatt   48960
cctaaataca tctaccctgt caagacagaa ccagaaataa ataggaaaca tgaacagacc   49020
aataacgagt aacaagactg aatcaataat aaaattctcc caaaaagaa agcccagga    49080 ccagatggct ttatttctga gttctaccaa acttttaaag caagacaaat gccaattctt   49140
ctcaagctat tcttaaagaa aaaaacgaaa aggagagaat tcttcttaat tcattctaca   49200
```

```
aagccagcat taccctgata gcaataccag ataaagagac aaccaaaaag aaaactacaa    49260
gccaatatgc aaagtttctc aacaaaatac taacaaactg aatctaacaa cacatctaaa    49320
aaataataga acataataaa gtgggattta tcccaaggat gcaaagaagg ttcaacatac    49380
acaaatcaat aaatgtgata catcacttca aaagagtgaa gaacaaaaac catatgatta    49440
tctcaactag cacagaaaaa aagcatttga tataattcaa gaactcttta tgatgaaaac    49500
tcttaacaaa ttggcataga aacaaagtat tgcaactcaa taaaggccat atattattaa    49560
cccacagcta tcatcttaca gaatgaggaa aaactgaaag tctttcttat aataactgaa    49620
taagacaagg atgcccactt ttaccactcc tattcaacat ctcactggaa gccctagcca    49680
gagcaattag gcaagagaaa gaaataaaag atgtccaagt tagaaagaa gaagtcaatt     49740 gtccctcttt gcagatgaca tgattataca tagaaaaatc taaatactcc accaggaaac    49800
tcttagaact gataaatgaa ttcagtaaag ttgccagata caaaattaac atacgagaat    49860
cagtagcatt ttttatatc ataatgaact agctgaagga gaaatcaaga aagcaatctg     49920
atttacaatt tttgccagga aaataaaata aaaataaaaa cctagaaata aatttaacca    49980
aggaggtgaa gacctctaca atgaaaacta caaaacacta atgaaagact gaagagaata    50040
caaacaactg taaagatata atatgcctat ggattggaaa aattaatatt gttaaaatga    50100
ccatactaca caaagcaatc tacaaacttta atgcaatccc tatcataata ccaatgacat    50160
ttttcacaga aagagaaaaa acagtcctaa aatttgtatg gaaatacaaa ggacttgaat    50220
agcaaaagca atactgctca aaaagaacaa agctggaggt ctcatactat ataatttcaa    50280
aatatactac aaagctataa ccaaaacaac atagcactgg tataaaaaca gacacataga    50340
ccaagggaat ggaatagaga agccagaaat aaatcaatgt atttacagcc aacttatttt    50400
tggcaaatat gaaagaacat acatgggaaa atgatggtct ctttaataaa tagtgctagg    50460
aaaactggat gttcacaggc agaagaagga aactagaccc ctatctctca ccatatataa    50520
gaatcaactt gaaatggata aaagacttaa acatgaaacc cagaaatata aaaccactag    50580
aagagaatat aggagaaatg cttcagaaca ttttttaggga agatattgt ggctgagatt     50640 tcaaaagcac aagtagcaaa aacaaaaaga aacaaatgtg actgtattaa actaaaaact    50700
tctacacagc aatggaaata attaacagag tggagagaca acctatagaa tgagacaaaa    50760
tatgtgcaaa ttattcatcc aacaagggat taattttcag aatatataag gaattcatac    50820
agctcaacag caaaacaaaa caacaacaaa aacctgatta aaaagtgagc aaagccttgt    50880
agcatagttt gaagtcaggt agcgtgacgc ctccagcttt gttcttttg cttaggattg     50940 tcttggctat acgggctctt ttttggttct atgtgaaatt taaagtagct ttttctaact    51000
ctgtgaagaa tttcagtgat agcttgttgg gaatagcatt gaatctataa attgctttgg    51060
gcagtatggc cattttcacg acattgattc ttcttttccat gagcatggaa tgtttttcca    51120
tttgcttgtg tcctctctta tttccttgag cagtggtttg tagttctcct tcaagaggtc    51180
cttcacatcc cttgtaagtt gtattcctag ttatttatt ctctttgtag caattgtgaa     51240
ttggagtttt ctcatgattt ggctctctat tattggttta tagggatgct tgtgattttt    51300
gcacattgat tttgtatcct gagactttgc tgaagttgct tatcagctta aggagttttg    51360
gggctgagac gatgaggttt tctaaatata caatcacatc atctgcaaac agagataatt    51420
tcacatcctc tcttcctatt tgaatatcct ttatttcttt ctcttgcctg attgccctgg    51480
ccagaacttc caatactatg ttgaatagga gtggtgagag agggcatcct tgttttgtac    51540
cagttttcaa aggaaatgta accgaacagc atggtaatgg aaccaaaaca aatatataga    51600
```

```
ccaattgaac agaaccgagg cctcagaaat agcatcacac atctacagcc atctttgaca   51660
aacctgacaa aaacaggaaa tggggaaagg tttccctatt taataaatgg cgctgggaaa   51720
actggctagc catatgcaga aaactgaaac tggaccccct ccttatgcct tagaacaaaa   51780
attaactcaa gatggattaa agacttaaac atacgaccta aaaccataaa accctagaa    51840 gaaaacctag gcaataccat tcacgacata ggcatgggaa gacttcatga ctaaaacacc   51900
aaaagcaatg gcaacaaagg cccaaattga caaatggtat ctatttaaac taaagagctt   51960
ctgcacagca aagaaaacta taatcagagt gaacaggtta cctacagaat gggagaaaat   52020
gtttgcaatt tatccacctg acaaagacct aatatccaga atctacaagg aacttaaaca   52080
aatttataag aaaaaaataa acaaacccat caaaaagtgg gcaaaggata tgaacagaca   52140
cttttcaaat ttatgcggcc aacaaacata tcaaaaaaag ttcatcatca ctggtcatta   52200
gagaaatgca aatcaaaacc acaaagagat atcatctcac accagttaga atggcgatca   52260
ttaaaaagtc aggaaacaac agatgctgga gaggatgtgg agaaatagga acgttttgc    52320 actgtttgta ggagtgtaaa ttagttcaac cattgtggaa gacagtgtgg tgattcctca   52380
aggatctaga actataaata ccatttgacc caccaatccc atatacccag aggattttaa   52440
atcattctac tataaagaca cattcacata tatgtttatt gcagctattc acaatagcaa   52500
agacttggaa ccaacccaaa tgcccatcaa tgttagactg gataaagaaa acgtggcaca   52560
tatacaccat ggaatactat acagccataa aaataatga gttcatgtcc tttgcaggga    52620
catggatgaa gcaggaaacc atcattctca gcaaactaac acaggaacag aaaaccaaag   52680
accgcacgtt ctcactccta agtgggagtt gaacaatgag aacatattgg cacagggagg   52740
ggaacatcac acattggggc ctgtcgcagg gtgggggaca aggggagaga tagcattaag   52800
agagatacct aatgtagatg acgggttgac gggtgcaaca aaccaccatg gcacatgtat   52860
acctatgtta caagcctgca cgttctgtat cccagaactt caagtataat aataaaacaa   52920
aagtgagcaa aggatgtgaa tagacatta tgaaactaaa acatacaaat ggccaataag    52980
tatgagaaaa aatgctcaag atcactaatc actggaaaaa aatgcaaatc aataccacaa   53040
tgagctatca caccttgtcag aatggctatt atcaaaaaga caaaagataa gtgttgatga   53100
ggatgtggag aaaaggaaac cattggaatt gttggtggga atgtgaatta gtacagccat   53160
tattgaaaac agtatgaagt ttcctcacaa aattaaaaat ggaactagca tgtgctcctg   53220
caatctcact accaagcagt tatccaaagg aaaggaaatc agtctattaa agggacacct   53280
gtaacttaat gtttattgca gcagtattca caatggctaa gacatggaat taacttaggt   53340
gtccatcaac aaacaaatgg atgaagaaaa tgtagtatat atacactcaa tgaaataacc   53400
ttcaggtata aaaaaagtat gaatcctgt cactcacagc aacacagatg agcctggagg    53460
actttatatt aagccaaatc ggtcagtcac agaaagataa acaccacatg ctgtcattta   53520
tatgtgggag ctaaaacata attgagttca tggaagtaga gaataaaatt gtgggtatta   53580
aaggcacaaa agggtaggag ggaggggacg ataggagaa gttggttaac agatgcaaaa    53640
ttataactag ataggaggaa ttagccctgg cattctgcag cactgcaggg tgaacatagt   53700
ttaccataat ttattgtata tgctcagaaa gctagaatga aggatttgga ttgttcataa   53760
cagaaagaaa tgatgaatgt tagagggat ggatatgcta attccctga tttgatcatt     53820 acacattgta tatcacatat ggaaatatat cactgtgtca tccataaata tgtacgacta   53880
ttgtgtcaac taaaaataaa aggaaaaaaa gtaaaaataa gggaaagtat ttattttacc   53940
```

```
ttcacttatt ctctgatgtt gttccttcct ttatttagat ccatgtttct aacttatgta    54000
attttccttc ttcctgaata gcttctgcta agatttcttg caaggcaggt ttacttgtaa    54060
caaattctct caattttttgt ttgtctgaga aaggctttat tcctccttca cttttgaagg    54120
ctaaattcac agagtacata atttaaacac tggttttttta ctcttaacat tttgaatatt    54180
tcattcctct ctcttttttgc ttgcatgatt tctgtggtga atttggatgt aattcttatc    54240
tttgctcttc tataagtaag ttgtttcttt tctccacttt gcattctttt ctagatattt    54300
tcttcatccc ttgattttttc tttttctgtc tcttctcctt ttttatattc ccattacatg    54360
tatgctactc cttttgtagt tgtcccacag ttcttagata ttctgttctt tttttatcagt    54420 tttttttttt ttgaattttt gcttctcagt tttggaagtt tctgttgtcc tatcattaga    54480
ctccaagatt cttctcctcag ctatgtgaag tctactaatg agcccatcaa aggcatattt    54540
tctttctgtt tttgatcttt atcatttttaa aattatttcc tagaattttta atctctctgc    54600 ttaaatttcc tatctgttct tgtctgttgt ctaattttttt cattacagct ctgacagctc    54660
tgagcatatt aatcatagac tttatttatt ttcttttttt gagacggagt ctcgctctgt    54720
tgcccaggct ggagtgcagt ggcacgatct cggctcacag aaacctccac ctctcaggtt    54780
cacgccattc tcctgcctca gcctcctgag tagctgggac tacaggtgcc cgccaccatg    54840
tccagctaat ttttttggtat ttttagtaga cggggtttt caccgtgtta gccaggatgg    54900
tctcgatctc ctgacctcgt gatctgcctg ccttggcctc tcaaagtgct gggattacag    54960
gcgtgagcca ccacgcctgg cctcaatcat agacttttaa aaagatttct gttctgataa    55020
ttccaacctc atgccatag gtaagtctag tccttatgct tgctctggct cttcaaactg    55080
tgtgttttgc cttctagtat gccttgtaat ttttttttttc atagctgatt ataatgttct    55140
gagtaaaaga aactgtgata aacaggcctt tagtgatgtc acaatacggt gtggaaaaag    55200
gggatgtgtt ctataagcct gtgattaggt cttagtcttt tggcgagcct gtgacctgga    55260
ctgtgaactt tcagtgctgc tcttttttttt cccctcctta ggtggtacag ggcagccttc    55320
caacatgtga aaaactagag gacccttgag ctgggtattt ttttccccag gcagatcaga    55380
ctctgataaa acctcagaag gttaggctct ggtaaaatag tcacccttga gtttaggccc    55440
tttaaaggag aacagactat tcagcttttt agaaattagt atttttttttt tgagacaggg    55500 tcttactgtc acccaggctg gagtgcagtg atataaaatca tggctcactg cagccttgac    55560
ctcctgggtt caagtgatgc tcctatttca acctgagtag ctgggaccac cagcatgtgc    55620
caccatgcat ggctaatttt tttgtaattg tttgtaaaga taggatctca ctatgttgtc    55680
caggctggtc tcaaacttct gggctcaagt gatcctccca cctctggctt atttttataat    55740 agtttttttcc cctcctccta ccagaagcac aagaggactt tctcatctga tacttactgt    55800
gaggacctag tagttagagc tcctaaagat caaactcata aaagtatata gccccacaa    55860 ctatgactgg gtaccttgg agttttaat tctctaagtt gtttcacact gagccttcag    55920
caatttgcca attacagttt aatttttttct acccccacaa tggttgctat ggaggtttct    55980
gctcatggat ctctgcttca gtaagttgtg gttctatctg tttctctaat ttggggatcc    56040
tctctttctc tccaacttta gggcagtggt ttgccctgtg acctcacttc tctgatctaa    56100
gaagagttgt tgattttttttt ttaatgggtt tagcttttta cttttaagta tggattggca    56160
acttctaagc ttcttatatg ccaaatggaa aagtagaagt tctcaaaaca actattttat    56220
actaatattt tattgattta tatagtatta agtattataa ttaaatgcta agtataactt    56280
agtgttaagg aattgactta gtcaataagc aactgaaatg gtgggagaaa atatacacga    56340
```

```
gtacataaga aactaaacta ctagtttgga gtcttcattg ttctctgggc attagtgaat    56400
atgttttgac agaaggaata gaaactattg atcatccaga aagtcagtta aatgacagtt    56460
aaacttctgg tagataagtg tgttcaagtg tctacatatg cattcacatt taaatatagg    56520
cttctacata gtacctttt ctcttaatgt tttattatag atttaccact tgtttatgaa    56580
cattacctga aaacaaatat atctgcttaa tattttattt tattttccat catctatttt    56640
accattccat tattagcttt cttttctatt ttagctgttt tctttatgta gataaatttt    56700
gaacaagact caatttactt gacctttaa ttggcattta ctatggacca ccacttcctc    56760
aaaacaatcc attctcttgg ctttccttct aactctctgg ctttactatt tgtctatttg    56820
acatctgttc ctgaatcttt gaaagtcagc tcaaacgtca tctgtttaaa acctaacaca    56880
taatttatac actccacctc ttcttctatt tcctatctca atggcaacac aatactgatg    56940
gtaaccagct taccatagtt aggcttataa tttttgaatt tacaatgggc ttattggaat    57000
gtaaacccat tgtaagttaa ggagcatctg actcttttgt tgtactcacc agacaactca    57060
agaatgatcc ttgatatgtc catcttgctt aattttatt ttcaaatcac attaaatttg    57120
cttatttctc aaatctattc atgtatttct agattctctc ttactatcaa gtgcaataaa    57180
taattatgtt aagcactgac tatgtaatag cctcataaag attcacccat atactttctt    57240
gaatctctcc aaaccatctg gcatatggct gttaatatga ccattgaaaa aagtaaaacta    57300 gaaaaactgt tcccatgttt gtaagtacaa atacattaat tattgctttt aggattgata    57360
caaaacttct taaaatatcc ttaaggccac acataatttg gtctcttcca gctctggctt    57420
tatgtcaaac cagttctgtc tcttcctctc tcagccatat tcctactttc ccttgctctc    57480
ttctttctag ccacatacag gccatgatcc ctctctcttc aaagtagtca cctatactat    57540
ttgctactga atccccctt tccctaaggt acttatgatt gagatctctt gtgaagtatc    57600
cttctccggg aagtattcat tgaggttttt aagtaaaatc ttcttgtata ggcttcatgg    57660
cagcatatat cttgtattca taacagttct caagttggga attgattgct gttattggat    57720
taatgttttt gccaccaaat aataaacttc ttgagggaag gagccacgta tgattttgat    57780
ccctgttgta ttcctaatac taaatggcac atggtaaatg ctcaaatatt tgatcaaaga    57840
ataaatgact ttaatttaaa ctaagaatta actaataagt catactataa tctgctaagc    57900
tacctgacaa atggtaaaaa ttgtagcaat tgagataaga ttccaggaac aatatacacc    57960
tttttcaaat ttcatacaga gtagattttc taaaaaataa gcagcgcatt ttaaaaggcc    58020
ccctaaataa ggcttcagat ggcacaaggc catggatagg ttgtcatagt gatgatcaga    58080
aatgaaaaat atttctactt tacttgaggt aaggagtttg aggacagcct ggccaacatg    58140
gtgaaaccca gtgtctacta aaaatataaa cattagctgg ctttggtggt gcatgcctgg    58200
aatccagtta cttaggaagc tgaggcagga gaattgcttg aacccaggag gcagaggttg    58260
cagtgagccg agaccatgcc actgcactcc agcctgggca acagacccca tctcaaaaaa    58320
aaaaaaaaaa aaaagcaat gaagtatatt tctataggga ccaactttat ttatagcaag    58380
agacatgaga ctgaatatat tctatgccaa aactttccaa tccttagaat cagccctaca    58440 aaagaaaga aaaagaaca gaaaggaagc agcaatcagc tatgagcaat aattagacat    58500
tcgtttgcta gctctagcac atgtgaccat gaagagtaac tgtgaaccat attgactttc    58560
tctcctgaaa agaaaatat gaaaaaatt cagaagaaaa ctgtcctatc acaaagaata    58620
cagaaattgg gtaagaatga acagctgttt catttcatta cctttgccct tttccacctt    58680
```

```
tattttttgga caattagttg atctaaaaag caatagttct ctatcagtca gttttttgcta   58740
caaacacata cacacacaga aagagagaaa ggcatacagt aatatgcatt taccttaggt   58800
tcacaggtat gcagtttggc tgagttcgat tacctccatg tgtttcattc taagtcataa   58860
gatggaagga gcagctgtat gggagtttta acatatgcac aaagatactc caccttacaa   58920
gaggtacagc ttaaattccc tcctcttgag tgtggattag aattagtgac tcactgcaag   58980
caactgaata atgaggaaat ggcagtgtgt gacttccatg taataaaaga catggcttcc   59040
tccttgcttt ctcttacatt gatacttggg ggaaagtcag caactatctt ggaaggatat   59100
tgaagaaagc ctgtggagaa actcatgtgg tgagaaattg aggcattctg ccaatacctg   59160
catgaatagg tcatcttggg aatagatcct ctaatcctga tggagtccag atgactacag   59220
acatgaccaa catcttgact gcctcctcat gaaagatgaa ctagaagctc ccggttaggc   59280
agcttccaaa ttcttgatcc acagaaactg tactgaaagc atcaatttct taccacatgt   59340
cttttggaca aactcaacat taatggacag aggagcatac ttctctatag taggctaaat   59400
aatggccacc cagataaaaa aattctaatc tgaaaatgta taaggtaaag gaatctacag   59460
atgtgattga attaagaatg ttggtgtgat aagtttattt tggattatct tggtgggccc   59520
taaatgctat cacaagttcc ttctaagaga aaagcaggag aagacttgac acccacacaa   59580
agaaggtgat gtgaagatgg aggcagagac tggagccact aggccacaag ccaaggaaca   59640
ctaaggaatg ctggcagaca ccagaagata aagaggcaa acaatgcatg ctctcccaga   59700
gcctctagaa atgtgagata ataagttttt attgttttga gcctccaaat ttttggtaat   59760
ttgttacatc agccatatgg aatgaaaaca tcctctcatt tgttgagttt agatgttaaa   59820
tactggctga acaataatct actctacttt agcatctttt caaaaataat cacaaaattt   59880
aaaaggaaaa ttatgcactg gtactagcaa aataaatgaa caaatgaatt aacacaaaat   59940
aggcaaaagg aaaatgaagt atctagacca aagtttaatt atccatgaaa gcaatggaaa   60000
atgtgaagtc tctaagaaac caatgtaaaa agagctaaaa acaatatagt atgaaagaaa   60060
ccagaaagaa acaaatgttc tttggatttt ggagaaatac agagactaaa ataaaaacca   60120
gaaatgaata ctccattaaa acaggcatat gaaagacagg atgggtaaaa accacacaaa   60180
acgaaattgt gtgtttgtgt atatatacgt gtgtacacac atacacgaaa agaaaagtt   60240
caatagaaga ttcattttttt atgtaattag tgtttctaaa aagatacttt aaaatgtaat   60300
ttaaaaattc aaagatagaa gaaaactatg ctgaaattaa agaagatata attctacaaa   60360
tgtaaagaac attatgtatt ttaagaactt gaaagaaaag gagtgggaa gtggccaaga   60420
tggccaacta gaagcagctc gtgtgagtgg ctctcacaaa gagggacaaa agggcgagta   60480
aatacagcac cttccactga aacatccaag tactcgcact gggactaatc aaggaaacaa   60540
cttgacccat ggagaacata gaaaacaaag gcaggacgac agcccacctg ggcacgacac   60600
ccagccaggt gaacctcccc tgcccagaga atcggtgagt gaatgtgtga ccctggaaac   60660
cacactcttc ccacgaatct ttgcaacctc gagttgggag atcccctctt gaacccactc   60720
catcagggct ttcagtctaa tacacagaga tacgggagtc ttggcagaga agctgctcag   60780
gcacatgttg gagaaccagg aactgtagat attccacctt caggcttccc ggcaaaagta   60840
actgcaactc cagaaaagca ggagattaga tccttgtgca taccccttagg aaagaggctg   60900
aatccagtgg gccaagcagc gatggtctgt aggccctact tccatggtgc ctcaaaggat   60960
aagacacatt ggcttggaat tccagccagc caccagcagc agtgttgtgc ctacctggga   61020
cagagttccc agggagaggg gaaggccacc atcttcactg tttgggcaag tcacctttttt   61080
```

```
cagcctgcag actttgaaga gtccaaaccg atcgggcaga agggatcccc caacacagca   61140
caattgctct accaacacgt ggccagactg cttctttaag caggtccctg agccatccct   61200
ccttattggg caggacctcc caaccagggc ctccagccat ccccgctggt gttctctggc   61260
ctacagagat ttgaaaactc cctgggacag aggtctcaga ggggaggggtg ggctgacatc   61320 tctgctattt gggtactgaa cctgtccagc ctgtgggctt tggagagccc aagccaacag   61380
gcggtgaagc gttaccccag cactgcgcag ctgctctaca aaagcatggc cagactgctt   61440
ctataagtgg gtccccaatc ctcttcctcc tgactgggca agacctccca accaggatct   61500
ccagccacct cctgcaggtg cgttccacct ggcaacaggt tcatacctcc ctgggccaga   61560
gctcttagaa gaagtggcag gctgccatct ttgctgtttt gcagccttca ctggtgatac   61620
cttcagctac cggaaaatcc aaggcaacta gggactggag tagaccccca gcaaaccaca   61680
gcagccctat ggaaaattgg ccaaattgtg ccaggggaa aaaaaaggt aggcaacgtc   61740 gaacattgaa ggtagattag ataagctcac agaaatgaga aagaatcaga gcaagaatgc   61800
tgaaacctca aaaagcctga gtgccctctt tcctccagct gacctcatta cctctccagc   61860
aagggttcaa aatagccagt atagagaagt acttaatcct cctgataggg ctgaaaaaca   61920
cactacaaga atttcgtaat gcaatcacaa gtattaatag tagaatagac caaacagagg   61980
aaagaatttc agagcttaat gaaatatggc aggcagacaa atgtagagaa aaagaatga    62040 aaggaatga acaaaacctc cgagaaatat ggaataccat atcacaccag tcagaatggc   62100
tataattaaa aagtcaaaaa ataacatgct ggcaaggttg tgaagaaaaa ggaatgctta   62160
tacactgttg gtgggaatgt aaatcagttc agccattgtg gaagatggta tggcaatttc   62220
tcaaagacct aaagacagat atactattca acccagcagt cccattactg gcatataac    62280 caagggaata taaatcattc tgttataaag acacatgcac atgtatgttc attgcagcac   62340
tattcacaat ggcaaagaca tggaatcaaa ctaaatggcc atcaataatg gactggataa   62400
agaaaatgtg gtacgtatac accatggaac actatgcagc cacaaaaaag aatgagatca   62460
atgagatcat gtccttttgca gggacatgga tggagctgga ggccattatc cttagcaaac   62520
taatgcagga acagaaaacc aaataccaca tgttctcact tataagtggc agctaaatga   62580
tcagaacaca tggacacata caggggaaca atacacactg gggcttttttg gaggatggag   62640 ggtaggaaga gggagaggat caaaaaacaa ttaatggata ctaggcttaa tacctgggtg   62700
atgaaataat ctatacaaaa aaacccatg acacaagttt acctatgtaa caaacctgca   62760
cttgtacccc tggacttaaa ataaatgttt aaaaaataga gaaagaaaaa gacactaaaa   62820
acatgaaaag atatgaaagc ataaactca ctgtaaagat aaagcataaa attcaccata   62880
aagataaaat atagtcaaat tcagagggct gtaatgaatt tgtatgtaat taagtgtata   62940
ctgtaattat agtttataag ttacttttcc tctactataa gagttaaaag acaaaagtat   63000
taaaaaataa cttcacctaa aaaaagaac ttagccaatg tcatgttta tactagaaaa    63060 tactgcagtt cagtcttata atcctggctt ttctcttctg attttccata tttataaaat   63120
atttgaagaa atttgtttct tatgtacatc ttgacatatg tgatatatga tttgtttctt   63180
tttatttttt atttttttct gagacagagt cttgctctgt tgcccaggct ggagtgcagt   63240
ggcgtgatct cagctcactg caagctccgc ctcccaggtt caagcgattc tcctgcctca   63300
gcctcccaag cagctgagat tacaggcatg tgccaccaca cccggctaat tttttttttt   63360
ttttttgtat ttttagtaga gatggggttt caccatgttg gccaggctgg tctcgaacta   63420
```

```
ctgacctcac gatctaccca ctttggcctc ccaaagggct gggattacag gcataaggca    63480
ccatgcctag ctgtgatttg tttcttattt gcatctggac atatgtgaca tgtgaataag    63540
aaacaattat tgggactttg gtcaagtaat tctattcttt gttaaatcaa aagatggcca    63600
tctaagtttc ttttcaacac catgtatcta taattcttac tctgagccat tcttctgata    63660
gggcatgaat gaaagaatt ttagaaagca acagtaattg gcaatcatat agatctatat    63720
tagatgcatt aataaaatgt actaaggtcg atgaattaat aactgtgacc tctataggag    63780
tcaacctttt aagggtatag taacacattt acattccata tcaagcatta ggtaaaaaat    63840
aatcaactgg tataacatta tctttctgtg gatctgccaa aaataagttt tattaataac    63900
ctagaacagc cacctaacca atatggcttt ttaaatattc atgtgtcatg caatttgcta    63960
acatgttgca agaaattggc attcattatg tgacatattg tctcatacga tatttttggt    64020
gaattggaag ataacatata gagtagctac acgtttcacc ttcttttttg aaggatgaca    64080
tggtaaaaat taaatactct atgtttatc aaagaaaaaa ttatgtatga gttattgtcc    64140
ttggggtatg gggaagtcaa catgaaaatg acttaatagg caaatattaa ttatccacta    64200
aattttcagg aatatgtaca atggcaatgt gaagatagtt attgaaaatg tatcttttac    64260
acttgagatg tatgtattca gacacttctt gcagataaag ctgatagtat atacatttta    64320
aaatcagggt aaacccagac atcatcatgc ttttcacagg tgataagagt aatgaatact    64380
tttctgagag gcagatgagg attcaaagcc catgactaaa tcctgccatt gctccacttc    64440
ttatcctgtt tctctggaga cattacatag gctaagattg ctttcagtcc cagaagctct    64500
gatagcatgg agttgctagt ttgctggaca gagctagtcc aacccggtgc ataagaaaat    64560
ctgaaacctt aggaggtttt tcctaatatc aactaaatta ttgatttaga taatctctac    64620
cttcttctac tacattcctt gtaaatgaaa aaaaaatag cgcacatatc agtctgcttt    64680
ctcactccta tgtttataat acacacatat aattacactg tctcaggaaa attctacctc    64740
aaccatccca gaaaattgga ttgctaaaaa tgttgtgaac aaatttcaac cttaattctc    64800
actgtcaatt tcaaagtact aatgcagatg gttttatatt ccttgcacat ccaattaatt    64860
agttgtgact gttgaaaata ctatgttgat tataagcctg tagtctcagc tcaactgaaa    64920
agagtgtaaa acagacaact gatatgaagg ggtaaagggt ttaggtatgt tatacatttg    64980
tgattctttc tcttatgtgt tgagctttgt atggatccct tcattctaat ataaattcct    65040
tttcttgtta tttgttgatg gcaggaaatt tgactgaata acctcttaag ttcatctcaa    65100
cttaatgact tcacatttta taatactttg tctataaagc ataacttcta aaataggtac    65160
ttctatttcc ctagatgagc cagattctct tagagaattc tgggattcaa ttatgggatc    65220 tgggagggggc tctaaaatatg ggaggatttg tgtatacact tatttatcct tcaactatag    65280
aaaatgattc ctcatgctta gtcagctgag ccaggcaaaa cttattttcc ttaaaatgca    65340
catataaata tcagatatta taagattatt atttttata attacaagat attagaaaag    65400
tactcagttt taaccatatt attttatgtt atttattaca ggacagcatg aaagaaattg    65460
gtagcaattg cctgaataat gaatttaact ttttttaaaag acatatctgt gatgctaata    65520
aggtaatgat aattattttgg agtttgtcat tcaagcttga ttttatagaa gcttctattt    65580
tttgtgcctc tgttagacaa ttatatgaat actattaata tttgcagcct gatcacataa    65640
ttcccattga ttaaatcata ctatggccca atttttatatt tttgttttac aaatagtcct    65700
gtgcttatta aataacaagt ttttttttgtt tcaccattct attttttacc ttgaaaatac    65760
tagaattgtc gaattcaaag acacacctat ctcttatttt cttctttct ttctttcttt    65820
```

```
gttttttttt tggaggcag agtttcgctc tgtcaccagg ctggagtgta gtggcgcaat   65880
ctcagctcac tgcaaactcc gcctcctggt ttcaagcgat tctcctgcct cagtctcccg   65940
agtaactggg tctacaggca tgcaccacca cacccaacta attttgtat ttttagtgga    66000 gacgggttt caccatgctg gccaggatga tctcgatctc ctgacctcat gatccgcctg    66060
cctccgcctc ccaaagtgct gggattacag gcgtgagcca cggtgcctgg cctctaaatt    66120
tcttatacag aaaaatactt gttaatgtga atgcttgcac acatacaaat ataagtcatt    66180
ggtataattt agttggaagc gtcttgaaaa ttttcttc aatatttgct tatctctaaa      66240
tgattaccac atctagttgg tataatatta cactttaaaa aacctaaaaa gtttatatca    66300
tttctcccta cagaaacaag tgtgctattt catagtcttt taaaaactca cagtagctaa    66360
gttagcctca tggcatctca caaccataaa ttcttttttt taaatttctt aatttaaata    66420
tctgcaaaac ttatgtttta ggtgactaca gtcctttatt ttcttattat cagctattct    66480
tccatagctc aaaagatgca agaaatacta agaaaaaacc acacatacct cttataatac    66540
attgttgctt ccagaagtct tctccttcgg ttatcatgtt taaaattgaa taatcttcta    66600
atatgttcac ataagcga taagatcaca taagcataat agagaaaaca aactttaaaa      66660
gtcaagataa ttattaaacc aagttctaag aacttcatgc tgtcacctag gagccaaaca    66720
gttttagttc tgttacttgt caatcacatg attaactgga atagaaagct ggggtggagg    66780
cggggcatta cctagcaaca tagctcaagc tctaggctcc ttaagaaagc ttataatttc    66840
ttaatatttt atttgaacca tggcccttct gactttttcc tataatagga aggtatgttt    66900
ttattccgtg ctgctcgcaa gttgaggcaa tttcttaaaa tgaatagcac tggtgatttt    66960
gatctccact tattaaaagt ttcagaaggc acaacaatac tgttgaactg cactggccag    67020
gtaagctaag gactatttac tttgaataaa aatattaaat actcctgtgc caagatacca    67080
ctattctctg atgatcacat ccattatcat agaatcctaa gtgtttatta tcatctaaag    67140
ttgaagtatg tttactcaat cctagaagag gaaaggctca gtttggaaat acctatttat    67200
ctcttggcta gagtgaattg tttgtgaaag gggagtaaaa aataaataaa taaattcttc    67260
attgccataa taacttccaa ggatactagg gtgatatatt gggtggggaa tggtaaattt    67320
ctatatctaa aacttattaa tagctttaat ccatatatgt acacatttac aagaactcct    67380
agtcaataaa acaggaaatc aaatgtattt aacaaatatc tttataggct taaactagac    67440
ataaacatgt ccaacaattt tcccttcttt aaataatttt gatacaaata gggctaatat    67500
tttcctactt ttctactagt ggttatgaac taaaacaaca aaaccaaata tggaagacat    67560
catctagaga ctagacagca gtttccttat ctacaaaatg cagaaaaaca tatctacatt    67620
gtgggatttg aaaggattaa atggcataac acatgtaaag tgcttagtac taaaaagttt    67680
tcaatattta atacagtgct ttattttatt tgtattattt acctcttttt ggattttacc    67740
agctgccaca caaaaccaaa agtttatttt atggttttaa atattttctt aaataacatt    67800
tttatgactt aaaaaagaat tttgtttgt ttgagcacta gtagtttccc atagaaggta    67860
aaatggtaag attatctttg aatcctattg acagtgataa aaatgtagat tatctatat    67920 ataacttgga tagcctcatt tatcattgct ttatgtactt gatggaagca agtctcctct    67980
tagtgtgctg gatttgccaa acttatttcc aaacttgcgt ccttacgttt gtcccctaga    68040
gagcatttct acttttttt tctataaatt ggatctattt tgttctatgc cttcaaggct    68100
cggctcaaga ttcatgaaga cttcctactc tagtctacca tttcttcatt cctacttaac    68160
```

```
agcggtttca aagtactgtc taatgcagat aggttttatg ttgcttgcac atccaattaa    68220
ttagttgtga ctgttgaaaa tactgtgttg attataagcc tccactcttg gttcaactga    68280
aaagagtgta aaacggaaaa ctgatatcac ctcttggtct actaagaggt aaaggtctta    68340
ggtatgttat atatttgtga ttctttctct tatgtattga gctttatatg gatcatcatg    68400
ttccaaaatt aactgtagag aaagaaaata tgcaaataat ttaaatcttt gaaattaaat    68460
tatattacat tgattaactt gatacaagtc accttttcct tgaaataaca aggcaagatg    68520
ttaaagcagt cagctacact gaattttctt catgagccag gcacgctaca agcttttac    68580 tattgtttta tttcattttg tttctgataa gtgaagctta ataaaatgta tggccaggat    68640
ttaacaattt cttgttaact ttattttat attgattaaa attcaagttt tatctctgct    68700 actatacccct actatgttaa tttttcatac ctcacagtag ttaacacagt actaggcaga    68760
cctacaaaat tatggattct gggtattcag aagactgaac tatcttgctt cttcctttac    68820
cctgatattc catttctaaa tcatattaat attttacttt cttaacaata agaaatttaa    68880
agtagagtct caaatagatt agatgagctg aaggcaatat gaaaattagc aattacaaac    68940
aactggagga gcaatgaaga atattcaat attataaatg tgactttgtt tttaaggtta    69000
aaggaagaaa accagctgcc ctgggtgaag cccaaccaac aaagagtttg gtgagaataa    69060
ttgtataatt ttccttatgg ttcatcaggt ttttactcaa cttaattcct aattttttcat    69120 tttgaattgt ttccttctta tagctggttt tgaaataatt tattataaca ttgataaaag    69180
gagaagcgag gtgcccctca aaatttgat tcctttaaat tgcatttta aacccactat    69240 tttaaaatag aagctgttag ggcaaataca aagcatgat tttttttttt tttagaagaa    69300
gcagcattaa aatattgcag ctagcacgta aaagaaatga acaaataatt tatataggag    69360
aaaataaact agatgacaaa tacatgaaga aaaaagcca tccctgttag tttgtaaaga    69420
aataaaaatt aaacaataag gacttatctt atatataccct cttttattag tgtagattgt    69480
acagtataaa taatatataa tagtatataa acatatattt atacatatac tactagacat    69540
tattagataa attatacaat aatatggaaa atatttatga atgacttaat aaggcagaat    69600
acttaaatgg atctgactaa actttaaaat gatataggta ctaattaagt tgaggcatgg    69660
aaaaatgagc acacctggtt cataaaagtg atggattctt cttttatatt tccattattt    69720
gaccaatagc tacatggcaa catggaaatt ccttactctt ttcagaaaag caaagtgagc    69780
ctgtacactc tgagatttag gaaattctag ggattctatg caaagtggaa catctgaagt    69840
gaatacagaa gctaaaagca atataatcac cctgaaggct tttcactaag agaatttgga    69900
aagtttagaa aagaaaggtt gggtgcggtg gctcacgcct gtaatcccag cactttgggg    69960
gtccgaggtg gcggatcac aaggtggaaa gatcaagacc atcctggcca acatggtgaa    70020
accccgtctc tactaaaaat acaaaaatta gctgggcgtg gtgcacgcct gtagtcccag    70080
ctactcagga ggctgaggca ggagaatcac ttgaacccag gaggtggagg ttgcagtgag    70140
ccgagatcgc gccactacac tctagcctgg gcaacagagt gggactccgt ctcaaaacaa    70200
aaaacaaaaa acagagcaaa aaaaaaaaa caaaaaaaa aaaaaagaa aagaaaagat    70260 aactattttc ccaggatgca gggggtaaaac caagattctc tgttttttac tttttagtga    70320
atgcttattc tcggtgtgca aggaaaagta tgaaatttc acatctgtat atttcaaatc    70380
tgcttaggca aatcaacttc aacttgtact taaaaaaatt gtccaggacc ccctattgaa    70440
aacaatatga aagtttgcc tttatattc cctttgagat ctgttgttta atctttgaaa    70500
tgtattcttt aaaaagtatg tgctagtgtt actaaataca tgacaaaaag agatctgaat    70560
```

```
ttgtggccaa attaaaaata ggacagagga gctcaagatt cagtcattat atttacttga   70620
catatattta tttacttgac cttagcagct tatttatctt ctttgcggat cagtttcttc   70680
atctgtgaaa tgagttcaaa tcatcaagtt catatgatga ttaagcaaat aaaatgaagt   70740
aaattatgtt aaacactgag cacaatatat gactgagaga atacccaata acttgttatc   70800
taaattatct agttacccaa taactagtta taatagtttt tatattgctt gcacatccat   70860
ttacttgcta gtgattgttg aaaacactat gttgatttta accctgaagt ctgggctcaa   70920
ctgtgaagag tgtaaaacaa acaactgata tcacctcctg gtctaggaag gggtaaaagt   70980
cactggtatg ctttatattt gtgatcaact agttgttatc taagtgaaga attactctac   71040
cctgcactat tcccattctc acaggtcaga ggactcagag aaatataact gagtctatac   71100
agagttactc ctttatatgt ctgttcatgc caagtatctc tttcttccta caggttgtac   71160
aggtagccct ttttaagatt cttgtcaggt gctaaaacct agcttatgag gcaggcatct   71220
gacatactct ggtgaaggtt agttgttgga ggagacctta gggtacaagt tccatcagct   71280
atatccttat tatctttggc aaaataatct gagtattttc aatgttgatt attcttccca   71340
ctaaaaatac attttctac attaaagaaa ctcaactgag taacctacaa ttacctttct   71400
catgaaattc caaacagtgt tattatgtcc actgttaaac tgtgaaaatg gcggtcagct   71460
gatatagctc tttggagaat cctaagtctt taatcacacc aaccttgaat tttctacatg   71520
tcagttatca caaagatagt tagaaatcat cgtctttaaa atgtcacaca ggattctacc   71580
ttttcattgc accagttttt cagtataaag taatatgatg aaaaatagta ttttaaaata   71640
tatattttg taaaaatgtg aagtttaaac ttttaaaact ctattctcta ggaagaaaat   71700
aaatctttaa aggaacagaa aaaactgaat gacttgtgtt tcctaaagag actattacaa   71760
gagataaaaa cttgttggaa taaaattttg atgggcacta aagaacactg aaaaatatgg   71820
agtggcaata tagaaacacg aactttagct gcatcctcca agaatctatc tgcttatgca   71880
gtttttcaga gtggaatgct tcctagaagt tactgaatgc accatggtca aaacggatta   71940
gggcatttga gaaatgcata ttgtattact agaagatgaa tacaaacaat ggaaactgaa   72000
tgctccagtc aacaaactat ttcttatata tgtgaacatt tatcaatcag tataattctg   72060
tactgatttt tgtaagacaa tccatgtaag gtatcagttg caataatact tctcaaacct   72120
gtttaaatat ttcaagacat taaatctatg aagtatataa tggtttcaaa gattcaaaat   72180
tgacattgct ttactgtcaa aataatttta tggctcacta tgaatctatt atactgtatt   72240
aagagtgaaa attgtcttct tctgtgctgg agatgtttta gagttaacaa tgatatatgg   72300
ataatgccgg tgagaataag agagtcataa accttaagta agcaacagca taacaaggtc   72360
caagatacct aaaagagatt tcaagagatt taattaatca tgaatgtgta acacagtgcc   72420
ttcaataaat ggtatagcaa atgttttgac atgaaaaaag gacaatttca aaaaaataaa   72480
ataaaataaa aataaattca cctagtctaa ggatgctaaa ccttagtact gagttacatt   72540
gtcatttata tagattataa cttgtctaaa taagtttgca atttgggaga tatatttta    72600
agataataat atatgtttac cttttaatta atgaaatatc tgtatttaat tttgacacta   72660
tatctgtata taaaatattt tcatacagca ttacaaattg cttactttgg aatacatttc   72720
tcctttgata aaataaatga gctatgtatt aa                                 72752
```

<210> SEQ ID NO 4
<211> LENGTH: 78
<212> TYPE: DNA

```
<213> ORGANISM: Unknown
<220> FEATURE:
<223> OTHER INFORMATION: Mammal

<400> SEQUENCE: 4
tgcaagcacc aaaaaggtga ccacacttca cattggcgat cgcgggtttc tatctgagga    60
tgtgaattta tttacaga                                                  78

<210> SEQ ID NO 5
<211> LENGTH: 152
<212> TYPE: DNA
<213> ORGANISM: Unknown
<220> FEATURE:
<223> OTHER INFORMATION: Mammal

<400> SEQUENCE: 5
gttatgtgct gatgggcttt atttgatcta cagaagatgc tctggtgaca ccctcagtgt    60
gtgttggtaa caccttcctg cctcgagata acttcgtata atgtatgcta tacgaagtta   120
tatgcatggc ctccgcgccg ggttttggcg cc                                 152

<210> SEQ ID NO 6
<211> LENGTH: 153
<212> TYPE: DNA
<213> ORGANISM: Unknown
<220> FEATURE:
<223> OTHER INFORMATION: Mammal

<400> SEQUENCE: 6
gtatgctata cgaagttatg ctagtaacta taacggtcct aaggtagcga gctagcccaa    60
ttgcgtactt tggatagtgt ctcttttttaa cctaaatgac ctttattaac actgtcaggt   120
tcccttactc tcgagagtgt tcattgctgc act                                153

<210> SEQ ID NO 7
<211> LENGTH: 24
<212> TYPE: DNA
<213> ORGANISM: Unknown
<220> FEATURE:
<223> OTHER INFORMATION: Mammal

<400> SEQUENCE: 7
ttgcattctt ttccaaataa gtgg                                           24

<210> SEQ ID NO 8
<211> LENGTH: 25
<212> TYPE: DNA
<213> ORGANISM: Unknown
<220> FEATURE:
<223> OTHER INFORMATION: Mammal

<400> SEQUENCE: 8
ttccaggatg aataggataa acagg                                          25

<210> SEQ ID NO 9
<211> LENGTH: 30
<212> TYPE: DNA
<213> ORGANISM: Unknown
<220> FEATURE:
<223> OTHER INFORMATION: Mammal

<400> SEQUENCE: 9
atccatcatc actccctgtg tttgtttccc                                     30
```

-continued

```
<210> SEQ ID NO 10
<211> LENGTH: 19
<212> TYPE: DNA
<213> ORGANISM: Unknown
<220> FEATURE:
<223> OTHER INFORMATION: Mammal

<400> SEQUENCE: 10
agctgactgc tgccgtcag                                                19

<210> SEQ ID NO 11
<211> LENGTH: 31
<212> TYPE: DNA
<213> ORGANISM: Unknown
<220> FEATURE:
<223> OTHER INFORMATION: Mammal

<400> SEQUENCE: 11
tagactttgt agtgttagaa acatttggaa c                                  31

<210> SEQ ID NO 12
<211> LENGTH: 33
<212> TYPE: DNA
<213> ORGANISM: Unknown
<220> FEATURE:
<223> OTHER INFORMATION: Mammal

<400> SEQUENCE: 12
atttttgtaa tgcaatcatg tcaactgcaa tgc                                33

<210> SEQ ID NO 13
<211> LENGTH: 22
<212> TYPE: DNA
<213> ORGANISM: Unknown
<220> FEATURE:
<223> OTHER INFORMATION: Mammal

<400> SEQUENCE: 13
ctcactctat cccatccaag gg                                            22

<210> SEQ ID NO 14
<211> LENGTH: 21
<212> TYPE: DNA
<213> ORGANISM: Unknown
<220> FEATURE:
<223> OTHER INFORMATION: Mammal

<400> SEQUENCE: 14
atgggcaggt agcatccaca g                                             21

<210> SEQ ID NO 15
<211> LENGTH: 29
<212> TYPE: DNA
<213> ORGANISM: Unknown
<220> FEATURE:
<223> OTHER INFORMATION: Mammal

<400> SEQUENCE: 15
tgaatcatcc ctttgtctag cagaaccgg                                     29
```